(12) United States Patent
Orhan et al.

(10) Patent No.: US 9,320,842 B2
(45) Date of Patent: Apr. 26, 2016

(54) MULTIMODAL DIALYSIS SYSTEM

(75) Inventors: Soykan Orhan, Shoreview, MN (US);
Bryant J. Pudil, Plymouth, MN (US);
Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 745 days.

(21) Appl. No.: 13/451,395

(22) Filed: Apr. 19, 2012

(65) Prior Publication Data

US 2012/0273354 A1    Nov. 1, 2012

Related U.S. Application Data

(63) Continuation-in-part of application No. 13/424,454, filed on Mar. 20, 2012, now Pat. No. 8,951,219, which is a continuation-in-part of application No. 13/424,467, filed on Mar. 20, 2012, now Pat. No.
(Continued)

(51) Int. Cl.
*B01D 61/26* (2006.01)
*B01D 61/32* (2006.01)
(Continued)

(52) U.S. Cl.
CPC ............. *A61M 1/1696* (2013.01); *A61M 1/14* (2013.01); *A61M 1/16* (2013.01); *A61M 1/1601* (2014.02);
(Continued)

(58) Field of Classification Search
CPC ....... A61M 1/1696; A61M 1/28; A61M 1/16; A61M 1/14; A61M 1/1601; A61M 1/1609; A61M 1/287; A61M 2205/3317; A61M 2205/3334; A61M 1/1605; A61M 1/1654; B01D 61/422; B01D 61/445; B01D 61/46; B01D 61/02

USPC ........... 210/645, 646, 647, 739, 745, 746, 85, 210/86, 96.1, 97, 134, 143, 194, 195.2, 252, 210/257.1, 258, 321.71, 502.1; 204/519, 204/520, 522, 627, 628, 630, 633; 604/4.01, 5.01, 6.11, 28, 29
See application file for complete search history.

(56) References Cited

U.S. PATENT DOCUMENTS 4,374,382 A     2/1983   Markowitz
4,508,622 A *   4/1985   Polaschegg et al. ......... 210/96.2
(Continued)

OTHER PUBLICATIONS

Lima, et. al., An electrochemical sensor based on nanostructure hollandite-type manganese oxide for detection of potassium ion, Sensors, 2009, 6613-6625, 9.

(Continued)

*Primary Examiner* — John Kim
(74) *Attorney, Agent, or Firm* — Hahn & Voight PLLC; Roger C. Hahn; Kenneth J. Collier

(57) ABSTRACT

A dialysis device for operation in multiple modes and for maintaining a known gradient of potassium ion or other electrolyte between the blood of a patient and a dialysate fluid is described. The dialysis device is capable of being used for hemodialysis or peritoneal dialysis, and the dialysis device is capable of operation with a dialysate purification unit outside of a clinical setting or with a supply of water that can be supplied in a clinical setting. The dialysis device has a composition sensor containing a potassium-sensitive electrode for measuring a potassium ion concentration in one or more of the patient's blood and the dialysate fluid and an infusate pump operated to adjust a potassium ion concentration in the dialysate fluid based at least in part on data from the composition sensor.

16 Claims, 43 Drawing Sheets

Related U.S. Application Data 8,926,542, application No. 13/451,395, which is a continuation-in-part of application No. 13/424,479, filed on Mar. 20, 2012, now Pat. No. 9,192,707, application No. 13/451,395, which is a continuation-in-part of application No. 13/424,490, filed on Mar. 20, 2012, now Pat. No. 9,061,099, application No. 13/451,395, which is a continuation-in-part of application No. 13/424,517, filed on Mar. 20, 2012, application No. 13/451,395, which is a continuation-in-part of application No. 13/424,533, filed on Mar. 20, 2012.

(60) Provisional application No. 61/480,528, filed on Apr. 29, 2011, provisional application No. 61/480,530, filed on Apr. 29, 2011, provisional application No. 61/480,532, filed on Apr. 29, 2011, provisional application No. 61/480,535, filed on Apr. 29, 2011, provisional application No. 61/480,541, filed on Apr. 29, 2011, provisional application No. 61/480,539, filed on Apr. 29, 2011.

(51) Int. Cl.
*B01D 61/42* (2006.01)
*B01D 61/44* (2006.01)
*B01D 61/46* (2006.01)
*A61M 1/14* (2006.01)
*A61M 1/28* (2006.01)
*A61M 1/16* (2006.01)
*B01D 61/02* (2006.01)

(52) U.S. Cl.
CPC ........... *A61M 1/1605* (2014.02); *A61M 1/1609* (2014.02); *A61M 1/1654* (2013.01); *A61M 1/28* (2013.01); *A61M 1/287* (2013.01); *B01D 61/02* (2013.01); *B01D 61/422* (2013.01); *B01D 61/445* (2013.01); *B01D 61/46* (2013.01); *A61M 2205/3317* (2013.01); *A61M 2205/3334* (2013.01)

(56) References Cited

U.S. PATENT DOCUMENTS

| | | | |
|---|---|---|---|
| 4,556,063 | A | 12/1985 | Thompson et al. |
| 5,127,404 | A | 7/1992 | Wyborny et al. |
| 5,683,432 | A | 11/1997 | Goedeke et al. |
| 7,674,231 | B2 | 3/2010 | McCombie et al. |
| 7,867,214 | B2* | 1/2011 | Childers ............. A61M 1/1656 210/644 |
| 8,404,091 | B2* | 3/2013 | Ding et al. .................... 204/527 |
| 8,858,792 | B2* | 10/2014 | Ding et al. ................. 210/195.2 |
| 2007/0066928 | A1* | 3/2007 | Lannoy ........................ 604/6.07 |
| 2007/0135750 | A1* | 6/2007 | Kraemer ...................... 604/6.09 |
| 2010/0051552 | A1* | 3/2010 | Rohde ................. A61M 1/1656 210/647 |

OTHER PUBLICATIONS

Hemametrics, Crit-Line Hematocrit Accuracy, 2003, 1-5, vol. 1, Tech Note No. 11 (Rev. D).

Siegenthalar, et. al., Pulmonary fluid status monitoring with intrathoracic impedance, Journal of Clinical Monitoring and Computing, 2010. 449-451 : 24.

Wang, Fundamentals of intrathoracic impedance monitoring in heart failure, Am, J. Cardiology, 2007, 3G-310 : Suppl.

Zhong, et. al., Miniture urea sensor based on H(+)-ion sensitive field effect transistor and its application in clinical analysis, Chin. J. Biotechnol., 1992, 57-65, 8(1).

Brynda, et. al.,The deecton of human β2-micogobulin by grating coupler immunosensor with thee dimensonal antibody networks, Biosensors & Bioelectronics, 1999, 363-368 14(4).

Nedelkov, et. al., Design of buffer exchange surfaces and sensor chips for biosensor chip mass spectrometry, Proteomics, 2002, 441-446, 2(4).

\* cited by examiner

MULTIMODAL DIALYSIS SYSTEM

The present application is a continuation in part of each of the following U.S. utility applications filed on Mar. 20, 2012: Ser. Nos. 13/424,454, 13/424,467, 13/424,479, 13/424,490, 13/424,517, and 13/424,533, which claim priority respectively to the following provisional applications filed on Apr. 29, 2011: Ser. Nos. 61/480,528, 61/480,530, 61/480,532, 61/480,535, 61/480,541, and 61/480,539. Each of the above-mentioned applications is hereby incorporated by reference in its entirety.

FIELD OF THE INVENTION

The invention relates to medical devices and systems that can provide dialysis treatment for a mammal as a stand-alone system or as part of a medical facility. The devices and systems can perform hemodialysis, hemofiltration, hemodiafiltration or peritoneal dialysis. The devices and systems include an electrodialyzer, chemical sorbents, electronic sensors, an electronic controller and a flow control apparatus. The invention further relates to methods for performing dialysis using the described devices and systems to remove toxins from body fluids.

BACKGROUND

During operation of typical dialysis machines performing hemodialysis, blood is passed through a dialysis chamber on one side of a dialysis membrane and a dialysate is passed on the other side of the dialysis membrane. In addition to diffusion of solutes across the dialysis membrane, a difference in pressure between the blood-side and the dialysate-side of the dialysis membrane drives the bulk movement of water from higher pressure to lower pressure. The pressure generated on a particular side of the dialysis membrane depends on several factors including flow rate, viscosity of the fluid, geometry of the dialyzer and physiological condition of the patient. The diffusion of impurities from the blood, across the dialysis membrane and into the dialysate is thermodynamically driven by the concentration gradient difference between the concentration of impurities in the blood and the concentration of those species in the dialysate. In most dialysis systems, large volumes of water are required to form the dialysate thereby requiring patients to regularly travel to a dialysis center to receive treatment for a chronic disease. In effect, dialysis patients are tethered to their dialysis center.

Moreover, dialysis treatments performed at dialysis centers are administered intermittently and fail to replicate the continuous waste removal aspect of a natural and functioning kidney. Once a dialysis session is completed, fluid and other substances such as sodium and potassium salts immediately begin to accumulate in the tissues of the patient. Notwithstanding the benefits of dialysis, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles continuous kidney function. However, the requirement for patients to travel to the dialysis centers and the costs associated with the hemodialysis procedure itself pose an upper limit on the frequency of dialysis procedures.

Known attempts to make portable dialysis systems usually rely upon the regeneration of spent dialysate (i.e. dialysate having urea and/or other impurities therein) to form refreshed dialysate that can be reused to perform dialysis. However, large quantities of water are required to reuse spent dialysate thereby limiting portability. Accumulated waste products and impurities must be removed from the spent dialysate, and the composition and pH of the regenerated dialysate must be regulated for physiological compatibility. Generally, regeneration of spent dialysate requires use of a sorbent cartridge through which spent dialysate is recirculated and regenerated. However, regenerated dialysate produced by known systems is subject to variations in pH and sodium concentrations non-conducive to physiological norms. Further, zirconium-based exchange materials used in many known sorbent systems are expensive and can release ions into the dialysate that affect conductivity and/or the pH of the dialysate, which necessitates the addition of further reagents to the dialysate to maintain the composition of the dialysate.

Hence, there is a need for a convenient dialysis system that can regenerate dialysate in a cost-effective manner. The system should remove impurities from spent dialysate solution. The system should have a weight and volume that is sufficiently light and small to be practicably carried by the patient while ambulatory. There is a need for a system that would allow a patient to travel wherein the system is no larger than about the size of luggage suitable for storage in an overhead bin of an airplane. Further, to facilitate regular usage, the system should be conducive to operation by a patient without the assistance of a medical professional.

There is also a need for a system that can be quickly set up in a new location without requiring specific sources of water or new water lines or pipes. The system must be patient-friendly and capable of operating on a small volume of dialysate and suitable for daily use, continuous use, short-term use, or use in a home-setting. There is also a need for a modular system that can provide any one or combination of hemodialysis, hemofiltration, hemodiafiltration and peritoneal dialysis.

SUMMARY OF THE INVENTION

The invention is directed to a semi-portable, multimodal medical device for dialysis. Related medical systems and methods for dialysate regeneration are provided herein.

In certain embodiments, a multimodal dialysis apparatus has a blood circuit for transporting blood extracorporeally to a hemodialysis unit, a dialysate circuit for transporting a fluid to contact the hemodialysis unit, wherein the fluid increases in concentration with at least one waste species during operation, and an infusate pump for adding a potassium salt to the fluid in the dialysis circuit. A composition sensor comprising a potassium-sensitive electrode for measuring a potassium ion concentration in one or more of blood in the blood circuit and fluid in the dialysate circuit is present. The infusate pump is controlled to adjust a potassium ion concentration in the fluid in the dialysate circuit based at least in part on data from the composition sensor.

In some embodiments, a multimodal dialysis apparatus has a dialysate circuit for conveying fluid to and from the peritoneal cavity of the patient, an infusion pump for adding a potassium salt to the fluid in the dialysis circuit, and a composition sensor comprising a potassium-sensitive electrode for measuring a potassium ion concentration in the fluid in the dialysate circuit. The infusate pump is controlled to adjust a potassium ion concentration in the fluid in the dialysate circuit based at least in part on data from the composition sensor.

In certain embodiments, dialysis is performed by contacting a dialysate fluid with a patient or a medical device such that at least one waste species is transferred from the patient to the dialysate fluid, measuring a potassium ion concentration of the contacted dialysate fluid, and controlling a potassium ion concentration in a dialysate fluid being conveyed to the patient or the medical device based upon the measured potassium ion concentration in the contacted dialysate fluid.

In one embodiment, a medical device acts as an extracorporeal dialysis device where the dialysate fluid is regenerated by first effectively removing the solutes therein, including the salts and the urea using an electrodialysis unit. Then, a physiological compatible amount of salts and other solutes are then added to reconstitute the dialysate.

In another embodiment, a medical device is used for peritoneal dialysis, where dialysate is regenerated by removal of the solutes, including the salts and the urea, therein using an electrodialysis unit. Then, a physiological compatible amount of salts and other solutes are then added to reconstitute the dialysate.

In another embodiment, a medical device functions by the removal of only part of the salts and other solutes from a dialysate using an electrodialysis unit or chemical sorbents. Then, a physiological compatible amount of salts and other solutes are added to reconstitute the dialysate.

In another embodiment, an amount of potassium ions in the dialysate going into the dialysate is adjusted based on the potassium concentration in the blood of the patient.

In another embodiment, a constant potassium gradient between the patient and a dialysate is maintained and thereby an overall rate of mass transfer is maintained.

In some embodiments, a medical system operates as a stand-alone, hence can be used as a portable dialyzer at home.

In other embodiments, a medical system operates in a location where there is a fresh water supply, such as at a dialysis center or properly equipped residential units.

In some embodiments, a medical system operates as a hemodialyzer, where the blood is circulated in an extracorporeal circuit for hemodialysis using the system.

In other embodiments, the system operates as a dialysate regeneration unit for the performance of peritoneal dialysis.

In certain embodiments, a method includes the steps of: (i) initiating a blood fluid removal session of a patient; (ii) monitoring an indicator of tissue fluid volume of the patient, or a portion thereof, during the blood fluid removal session; (iii) monitoring an indicator of blood fluid volume of the patient during the blood fluid removal session; (iv) determining whether a ratio of the indicator of tissue fluid volume to indicator of blood fluid volume is outside of a predetermined range; and (iv) altering the rate of fluid removal during the blood fluid removal session if the ratio is determined to be outside of the predetermined range.

In certain embodiments, a predetermined range is based on measurements of the indicator of tissue fluid volume and the indicator of blood fluid volume obtained prior to initiating the blood fluid removal session.

In certain embodiments, if a ratio the indicator of tissue fluid volume to the indicator of blood fluid volume is outside the predetermined range and is indicative of exceeding a threshold of tissue fluid volume to blood fluid volume, then the rate of fluid removal is decreased.

In certain embodiments, if a ratio the indicator of tissue fluid volume to the indicator of blood fluid volume is outside the predetermined range and is indicative of a falling below a threshold of tissue fluid volume to blood fluid volume, then the rate of fluid removal is increased.

In certain embodiments, a method has the steps of: monitoring the indicator of tissue fluid volume of the patient prior to initiating the blood fluid removal session or monitoring the indicator of blood fluid volume of the patient prior to initiating the blood fluid removal session; setting an initial fluid volume removal prescription for the blood fluid removal session based on the indicator of tissue fluid volume monitored prior to initiating the blood fluid removal session or the indicator of blood fluid volume monitored prior to initiating the blood fluid removal session.

In certain embodiments, monitoring an indicator of tissue fluid volume of the patient prior to initiating the blood fluid removal session or monitoring the indicator of blood fluid volume of the patient prior to initiating the blood fluid removal session has chronically monitoring the indicator of tissue fluid volume.

In certain embodiments, a method has the steps of (i) determining whether the indicator of tissue fluid volume or the indicator of blood fluid volume monitored prior to initiating the blood fluid removal session crosses a predetermined threshold value, and (ii) scheduling the blood fluid removal session or providing an alert if the indicator crosses the threshold value.

In certain embodiments, a method has the steps of: (i) determining whether the indicator of tissue fluid volume is outside of a predetermined range or determining whether the indicator of blood fluid volume is outside of a predetermined range; and (ii) altering the rate of fluid removal if the indicator of tissue fluid volume is determined to be outside of a predetermined range or if the indicator of blood fluid volume is determined to be outside of a predetermined range.

In certain embodiments, a predetermined range of the indicator of tissue fluid volume or the predetermined range of blood fluid volume is determined based on the ratio of the indicator of tissue fluid volume to blood fluid volume.

In certain embodiments, a determination as to whether the indicator of tissue fluid volume is outside of a predetermined range is made.

In certain embodiments, an indicator of tissue fluid volume is impedance of flow of electricity through tissue of the patient.

In certain embodiments, impedance is measured between two electrodes placed in contact with the patient's skin.

In certain embodiments, monitoring the indicator of blood fluid volume includes measuring a hematocrit level, or an indicator thereof.

In certain embodiments, measuring a hematocrit level or the indicator thereof includes measuring oxygenated hemoglobin concentration.

In certain embodiments, a method has the steps of: (i) initiating a blood fluid removal session of a patient; (ii) monitoring an indicator of tissue fluid volume of the patient, or a portion thereof, during the blood fluid removal session; (iii) calculating a value indicative of tissue fluid volume based on the monitored indicator of tissue fluid volume; (iv) monitoring an indicator of blood fluid volume of the patient during the blood fluid removal session; (v) calculating a value indicative of blood fluid volume based on the monitored indicator of blood fluid volume; (vi) determining whether a ratio of the value indicative of tissue fluid volume to the value indicative of blood fluid volume is outside of a predetermined range; and (vii) altering the rate of fluid removal during the blood fluid removal session if the ratio is determined to be outside of the predetermined range.

In certain embodiments, a system has: (a) a blood fluid removal device comprising (i) an inlet for receiving blood from a patient, (ii) an first outlet for returning blood from the patient, (iii) a medium for removing fluid and contaminants from the blood, the medium being positioned between the inlet and the first outlet, (iv) a fluid rate removal controller; and (v) a second outlet for flow of the removed fluid and contaminants; (b) a first sensor for monitoring an indicator of tissue fluid volume; (c) a second sensor for monitoring an indicator of blood fluid volume; (d) control electronics in operable communication with the sensor for monitoring an indicator of tissue fluid volume, the sensor for monitoring an indicator of blood fluid volume; and the fluid rate removal controller, wherein the control electronics are configured to adjust the rate at which fluid is removed based on data obtained from the first sensor and the second sensor.

In certain embodiments, a system has a computer readable medium, wherein the computer readable medium comprises instructions that cause the control electronics to adjust the rate at which fluid is removed based on data obtained from the first sensor and the second sensor.

In certain embodiments, a computer readable medium has instructions that cause control electronics to (i) calculate a ratio of the indicator of tissue fluid volume to the indicator of blood fluid volume based on data obtained from the first and second sensors, respectively; (ii) determine whether the calculated ratio is outside of a predetermined range; and (iii) alter the rate of fluid removal if the ratio is determined to be outside of the predetermined range.

In certain embodiments, a computer readable medium has instructions that cause control electronics to (i) calculate a value indicative of tissue fluid volume based data obtained from the first sensor; (ii) calculate a value indicative of blood fluid volume based on data obtained from the second sensor; (iii) determine whether a ratio of the value indicative of tissue fluid volume to the value indicative of blood fluid volume is outside of a predetermined range; and (iv) alter the rate of fluid removal if the ratio is determined to be outside of the predetermined range.

In certain embodiments, a fluid rate removal controller has one or more of a blood flow control component, a negative pressure control component, a dialysis flow control component, and a fresh fluid flow control component.

In certain embodiments, a medium for removal of fluid and contaminants from the blood has a filtration membrane.

In certain embodiments, one or more components of a first sensor, a second sensor and control electronics are housed within the blood fluid removal or dialysis device.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

In certain embodiments, a method has the steps of: (i) monitoring an indicator of fluid volume of a patient via an implantable sensor device; and setting an initial fluid volume removal prescription for a blood fluid removal session based on the monitored indicator of fluid volume.

In certain embodiments, a method has the steps of transmitting data regarding the indicator of fluid volume from the implantable sensor device to fluid removal device.

In certain embodiments, setting an initial fluid volume removal prescription includes calculating the fluid volume prescription by the fluid removal device based on the data received from the implantable sensor.

In certain embodiments, an indicator of fluid volume is an indicator of tissue fluid volume or an indicator of blood fluid volume.

In certain embodiments, an indicator of fluid volume is tissue impedance or blood hematocrit.

In certain embodiments, an indicator of fluid volume is tissue impedance.

In certain embodiments, a method has the steps of determining whether the indicator of fluid volume crosses a predetermined threshold value, and providing an alert to the patient if the indicator of fluid volume is determined to cross the threshold value.

In certain embodiments, a method has the steps of automatically scheduling a blood fluid removal or dialysis session if the indicator crosses the threshold value by transmitting a signal from the sensor to a healthcare provider via an intermediary device.

In certain embodiments, monitoring an indicator of fluid volume includes monitoring an indicator of tissue fluid volume, wherein the method further comprises monitoring an indicator of blood fluid volume, and wherein setting the initial fluid volume removal prescription for the blood fluid removal session based on the monitored indicator of fluid volume comprises setting the initial fluid volume removal prescription based on the ratio of the monitored indicators of tissue fluid volume and blood fluid volume.

In certain embodiments, monitoring an indicator of fluid volume includes monitoring an indicator of blood fluid volume, wherein the method further comprises monitoring an indicator of tissue fluid volume, and wherein setting the initial fluid volume removal prescription for the blood fluid removal session comprises setting the initial fluid volume removal prescription based on the ratio of the monitored indicators of tissue fluid volume and blood fluid volume.

In certain embodiments, a system has (a) a sensor configured to monitor an indicator of fluid volume; and (b) a blood fluid removal device comprising (i) an inlet for receiving blood from a patient, (ii) an first outlet for returning blood from the patient, (iii) a medium for removing fluid from the blood, the medium being positioned between the inlet and the first outlet, (iv) a fluid rate removal controller, (v) a second outlet for flow of the removed fluid, and (vi) electronics coupled to the fluid rate removal controller and the sensor, wherein the electronics are configured to set an initial fluid rate removal prescription based on data received from the sensor and to control the fluid rate removal controller based on the set initial fluid rate removal prescription.

In certain embodiments, a sensor is implantable. In certain embodiments, a sensor is wearable. In certain embodiments, electronics include a computer readable medium that, when implemented, cause the electronics to calculate the initial fluid rate removal prescription based on data received from the sensor and instruct the fluid rate removal controller to operate according to the initial fluid rate removal prescription.

In certain embodiments, a sensor and the fluid removal device are implantable. In certain embodiments, a sensor and the fluid removal device are wearable. In certain embodiments, control electronics are disposed in a housing of the blood fluid removal device In certain embodiments, a method carried out by an implantable device has the steps of: (i) monitoring indicator of fluid volume in a patient suffering from chronic kidney disease, wherein the monitoring is performed, at least in part, by an implantable sensor device; (ii) determining whether the monitored indicator of fluid volume crosses a predetermined threshold; and (iii) providing a sensory cue to the patient if the monitored indicator is determined to cross the threshold.

In certain embodiments, a method has the steps of automatically scheduling a blood fluid removal session if the monitored indicator is determined to cross the threshold.

In certain embodiments, a system has: (a) an implantable sensor device configured to monitor impedance of tissue of a patient, the device comprising (i) a first electrode, (ii) a second electrode, (iii) electronics operably coupled to the first and second electrodes for monitoring impedance of current flow between the two electrodes, and (iv) a first communication circuit configured to transmit data regarding the monitored impedance; (b) a fluid removal device for removing fluid from a patient, the device comprising (i) an inlet for receiving blood from a patient, (ii) a medium in for removing fluid from the blood, the medium being in communication with the inlet, (iii) an outlet in communication with the medium for returning blood to the patient; (iv) a flow controller in communication with the inlet, outlet or medium configured to control the rate at which the fluid is removed from the medium; (c) a second communication circuit configured to wirelessly receive the data regarding the impedance from the implantable device; and (d) electronics in communication with the second communication circuit and the flow controller wherein the electronics are configured to set an initial fluid removal prescription for a fluid removal session based on the impedance data received prior to the start of the session and to control the flow controller regarding the rate of fluid removal based on the received impedance data.

In certain embodiments, electronics of a fluid removal or dialysis device are configured to alter the initial fluid removal rate or profile during a fluid removal session based on the on the impedance data received during the session.

In certain embodiments, a fluid removal device is implantable, and wherein the first communication circuit of the sensor device and the second communication circuit of the fluid removal device are the same circuit.

In certain embodiments, control electronics are disposed in a housing of the blood fluid removal device.

In certain embodiments, a sensor device has: (i) a detector circuit and components configured to acquire sensed data regarding an indicator of fluid volume; (ii) control electronic configured to receive the acquired sensed data from the detector circuit and to calculate a fluid volume removal prescription based on the acquired sensed data.

In certain embodiments, a system has: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, the fluid selected from dialysate and replacement fluid, wherein if the fluid is dialysate the fluid source carries the fluid to the medium, and wherein if the fluid is replacement fluid the fluid source carries the fluid to the blood after the blood exits the medium; (b) a concentrate source for housing a concentrate solution comprising concentrated electrolyte or pH buffer; (c) a concentrate flow control element for controlling the rate that the concentrate solution enters the fluid source; (d) a first sensor configured to monitor an indicator of blood electrolyte concentration or blood pH; and (e) control electronics in operable communication with the sensor and the concentrate flow control element, wherein the control electronics are configured, via the concentrate flow control element, to adjust the rate at which the concentrate solution enters the fluid source based on data obtained from the sensor.

In certain embodiments, a first sensor is configured to monitor blood before the blood enters the medium.

In certain embodiments, a system has a second sensor configured to monitor an indicator of blood electrolyte concentration or blood pH, the second sensor being configured to monitor blood after the blood exits the medium.

In certain embodiments, control electronics are in operable communication with the second sensor and are configured to compare data acquired from the first sensor to data acquired from the second sensor, and wherein the control electronics are configured to adjust the rate at which the concentrate solution enters the fluid source based on the comparison of the data acquired from the first sensor and the second sensor.

In certain embodiments, a first sensor is configured to monitor the indicator in fluid removed from the blood after the fluid removed from the blood exits the medium In certain embodiments, control electronics are configured to derive the blood pH or blood electrolyte concentration based on data acquired from the first sensor.

In certain embodiments, a system has a second sensor configured to monitor the indicator in dialysate in the fluid source before the dialysate enters the medium, wherein the control electronics are control electronics are in operable communication with the second sensor and are configured to compare data acquired from the first sensor to data acquired from the second sensor, and wherein the control electronics are configured to adjust the rate at which the concentrate solution enters the fluid source based on the comparison of the data acquired from the first sensor and the second sensor.

In certain embodiments, a first sensor is configured to monitor the indicator in the blood after the blood exits the medium and before replacement fluid is added to the blood.

In certain embodiments, a system has a second sensor configured to monitor the indicator in the blood after the replacement fluid has been added to the blood.

In certain embodiments, control electronics, or components thereof, are housed within a housing of the blood fluid removal device.

In certain embodiments, a system has a computer readable medium, wherein the computer readable medium comprises instructions that cause the control electronics to control the concentrate flow control element to adjust the rate at which the concentrate solution enters the fluid source based on data obtained from the sensor.

In certain embodiments, a method has the steps of: (i) initiating blood fluid removal procedure for a patient in need thereof, wherein the procedure comprise use of a fluid selected from a dialysate fluid or a replacement fluid, and wherein the fluid has an initial pH buffer composition or electrolyte composition; (ii) monitoring an indicator of blood electrolyte concentration or blood pH of the patient during the blood fluid removal session; and (iii) adjusting the pH buffer composition or the electrolyte composition of the fluid based on a value of the monitored indicator.

In certain embodiments, monitoring the indicator includes monitoring the indicator in blood before passing the blood through a blood fluid removal medium and after passing the blood through the blood fluid removal medium In certain embodiments, a method has the steps of comparing a value of the indicator monitored before the blood is passed through the medium to a value of the indicator monitored after passing the blood through the medium, wherein adjusting the pH buffer composition or the electrolyte composition comprises adjusting the composition based on the comparison.

In certain embodiments, adjusting the composition has the steps of adding a concentrated electrolyte solution or buffer solution to the fluid.

In certain embodiments, a method has the steps of (i) determining whether a value of the monitored indicator crosses a threshold; and (ii) providing an alert if the value of the monitored indicator is determined to cross the threshold.

In certain embodiments, monitoring an indicator has the steps of monitoring the indicator in fluid removed from the blood.

In certain embodiments, a method has the steps of determining a blood electrolyte concentration or pH from a value of the monitored indicator of the fluid removed from the blood.

In certain embodiments, the fluid for use in a blood fluid removal or dialysis procedure is dialysate, and wherein monitoring the indicator further comprises monitoring the indicator in the dialysate prior to the dialysate entering a blood fluid removal medium, and wherein the method further comprises comparing a value of the monitored indicator in fluid removed from the blood to a value of the monitored indicator in the dialysate prior to entering the blood fluid removal medium.

In certain embodiments, the fluid for use in a blood fluid removal or dialysis procedure is replacement fluid, and wherein monitoring the indicator comprises monitoring the indicator in blood downstream of a blood fluid removal medium and upstream of addition of the replacement fluid to the blood.

In certain embodiments, monitoring an indicator further has the steps of monitoring the indicator in the blood downstream of the addition of the replacement fluid, wherein the method further comprises comparing a value of the monitored indicator obtained upstream of the addition of replacement fluid to a value of the monitored indicator obtained downstream of the addition of replacement fluid.

In certain embodiments, a system has: (i) a medium housing defining a major chamber; (ii) a blood flow removal membrane disposed in the housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber through the first outlet; (iv) a second inlet and a second outlet in fluid communication with the second minor chamber, wherein the system is configured such that dialysate enters the second minor chamber through the second inlet and exits the second minor chamber through the second outlet; (v) a dialysate regeneration medium in fluid communication with and disposed in a dialysate flow path between the second inlet and the second outlet; (vi) a concentrate source for housing a concentrate solution comprising concentrated electrolyte or pH buffer; (vii) a concentrate flow control element for controlling the rate that the concentrate solution enters the dialysate flow path downstream of the dialysate regeneration medium and upstream of the second inlet; (viii) a sensor configured to monitor an indicator of electrolyte concentration or pH of dialysate in the dialysate flow path downstream of the dialysate regeneration medium and upstream of the second inlet; and (ix) control electronics in operable communication with the sensor and the concentrate flow control element, wherein the control electronics are configured, via the concentrate flow control element, to adjust the rate at which the concentrate solution enters the dialysate flow path based on data obtained from the sensor.

In certain embodiments, a method carried out by a blood fluid removal or dialysis device or system, has the steps of: (i) initiating blood fluid removal procedure for a patient in need thereof, wherein the procedure comprises use of a dialysate fluid and a dialysate membrane, as at least a part of a blood fluid removal medium, across which electrolytes may be exchanged between blood and the dialysate fluid; (ii) monitoring an indicator of blood electrolyte concentration or blood pH during the blood fluid removal session; and (iii) adjusting the flow rate of the dialysate fluid or blood based on a value of the monitored indicator.

In certain embodiments, monitoring an indicator has the steps of monitoring the indicator in blood before passing the blood through the blood fluid removal medium and after passing the blood through the blood fluid removal medium.

In certain embodiments, a method has the steps of comparing a value of the indicator monitored before the blood is passed through the medium to a value of the indicator monitored after passing the blood through the medium, wherein adjusting the flow rate of the dialysate fluid or the blood comprises adjusting the composition based on the comparison.

In certain embodiments, monitoring the indicator has the step of monitoring the indicator in fluid removed from the blood.

In certain embodiments, a method has the steps of determining a blood electrolyte concentration or pH from a value of the monitored indicator of the fluid removed from the blood.

In certain embodiments, a method has the steps of (i) initiating a blood fluid removal session for a patient in need thereof; (ii) monitoring a cardiovascular parameter of the patient; (iii) determining whether the indicator of the cardiovascular state crosses a predetermined threshold; and (iv) altering a parameter of the blood fluid removal session if the indicator is determined have crossed the threshold.

In certain embodiments, a predetermined threshold is based on measurements of the cardiovascular parameter obtained prior to initiating the blood fluid removal session.

In certain embodiments, a method has the steps of monitoring a cardiovascular parameter of the patient prior to initiating the blood fluid removal session, and setting an initial prescription for the blood fluid removal session based on the cardiovascular parameter monitored prior to initiating the blood fluid removal session.

In certain embodiments, the setting of an initial prescription for the blood fluid removal session has the steps of setting a fluid removal prescription or setting a dialysate composition prescription.

In certain embodiments, monitoring a cardiovascular parameter of the patient prior to initiating the blood fluid removal session has the step of chronically monitoring the cardiovascular parameter.

In certain embodiments, a method has the steps of (i) determining whether the cardiovascular parameter crosses a predetermined threshold, and (ii) scheduling the blood fluid removal session or providing an alert if the parameter crosses the threshold.

In certain embodiments, monitoring a cardiovascular parameter has the step of monitoring one or more of heart rate, heart rhythm or blood pressure.

In certain embodiments, altering a parameter of the blood fluid removal session has the step of altering the rate of removal of fluid from the patient's blood.

In certain embodiments, altering a parameter of the blood fluid removal session has the step of altering a concentration of a component of a fluid selected from dialysate or replacement fluid.

In certain embodiments, a method has the steps of: (i) receiving data regarding a monitored cardiovascular parameter to a blood fluid removal device or system; and (ii) setting a parameter for a blood fluid removal session based on the received data regarding the monitored cardiovascular parameter, wherein the parameter is set by control electronics of a blood fluid removal device or system.

In certain embodiments, setting an initial prescription for the blood fluid removal session has the steps of setting a fluid volume removal prescription.

In certain embodiments, setting an initial prescription for the blood fluid removal session has the steps of setting a dialysate composition or a replacement fluid composition.

In certain embodiments, a cardiovascular parameter has one or more of heart rate, heart rhythm and blood pressure.

In certain embodiments, a system has: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a control element for controlling the rate at which fluid is removed from the blood by the medium; (b) a sensor for monitoring a cardiovascular parameter of the patient; and (c) control electronics in operable communication with the sensor and the control element, wherein the control electronics are configured, via the control element, to adjust the rate at which the fluid is removed from the blood.

In certain embodiments, the blood fluid removal or dialysis device further has a fluid source for carrying a system fluid, the system fluid selected from dialysate and replacement fluid, wherein if the fluid is dialysate the fluid source carries the fluid to the medium, and wherein if the fluid is replacement fluid the fluid source carries the fluid to the blood after the blood exits the medium; wherein the system further comprises (i) a concentrate source for housing a concentrate solution comprising a concentrated component for the system fluid; and (ii) a concentrate flow control element for controlling the rate that the concentrate solution enters the fluid source, wherein the sensor is operably coupled to the control electronics and the control electronics are further configured, via the concentrate flow control element, to adjust the rate at which the concentrate solution enters the fluid source based on data obtained from the sensor.

In certain embodiments, control electronics are housed within the blood fluid removal device.

In certain embodiments, a system has: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, the fluid selected from dialysate and replacement fluid, wherein if the fluid is dialysate the fluid source carries the fluid to the medium, and wherein if the fluid is replacement fluid the fluid source carries the fluid to the blood after the blood exits the medium; (b) a concentrate source for housing a concentrate solution comprising a concentrated component for the fluid; (c) a concentrate flow control element for controlling the rate that the concentrate solution enters the fluid source; (d) a first sensor for monitoring a cardiovascular parameter of the patient; and (e) control electronics in operable communication with the sensor and the concentrate flow control element, wherein the control electronics are configured, via the concentrate flow control element, to adjust the rate at which the concentrate solution enters the fluid source based on data obtained from the sensor.

In certain embodiments, control electronics are housed within the blood fluid removal device.

In certain embodiments, a system has a computer readable medium, wherein the computer readable medium comprises instructions that cause the control electronics to control the concentrate flow control element to adjust the rate at which the concentrate solution enters the fluid source based on data obtained from the sensor.

In certain embodiments, a method carried out by a blood fluid removal or dialysis device or system, has the steps of: (i) receiving data regarding a monitored cardiovascular parameter to a blood fluid removal device or system; and (ii) aborting a blood fluid removal session based on the received data regarding the monitored cardiovascular parameter.

In certain embodiments, a blood fluid removal or dialysis session is aborted before the beginning of the session.

In certain embodiments, an ultrafiltration system has (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of fluid flow at or downstream of the second outlet; and control electronics configured to acquire data from the first sensor and configured to determine whether the membrane is functioning within predetermined parameters based on the acquired data.

In certain embodiments, a system has a control element configured to adjust the pressure differential between the first minor chamber and the second minor chamber, and wherein the control electronics are further configured to cause the control element to adjust the pressure differential based on the data acquired from the sensor.

In certain embodiments, a system has an alert circuit configured to alert a patient or a healthcare provider, wherein the control electronics are configured to activate the alert circuit if the control electronics determine that membrane is not functioning within the predetermined parameters.

In certain embodiments, a system has a second sensor configured to detect an indicator of flow rate at or upstream of the first inlet or at or downstream of the first outlet, wherein the control electronics are configured to acquire data from the second sensor, and wherein the control electronics are configured to determine whether the membrane is functioning within predetermined parameters based on the data acquired from the first and second sensors.

In certain embodiments, a blood fluid removal or dialysis system has: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of a blood waste product or fluid flow at or downstream of the second outlet; and (vi) control electronics configured to acquire data from the sensor and configured to determine whether the membrane is functioning within predetermined parameters based on the acquired data.

In certain embodiments, a system has a control element configured to adjust the pressure differential between the first minor chamber and the second minor chamber, and wherein the control electronics are further configured to cause the control element to adjust the pressure differential based on the data acquired from the first sensor.

In certain embodiments, a system has an alert circuit configured to alert a patient or a healthcare provider, wherein the control electronics are configured to activate the alert circuit if the control electronics determine that membrane is not functioning within the predetermined parameters.

In certain embodiments, a system has a second sensor configured to detect the indicator of a blood waste product or fluid flow at or upstream of the first inlet, wherein the control electronics are configured to acquire data from the second sensor, and wherein the control electronics are configured to compare data acquired from the first sensor to data acquired from the second sensor in determining whether the membrane is functioning within predetermined parameters.

In certain embodiments, a system has (i) a second inlet in communication with the second minor chamber, wherein dialysate is configured to flow through the second inlet and the second outlet; and (ii) a dialysate flow controller operably coupled to the control electronics, wherein control electronics are configured to increase dialysate flow rate, via the dialysate flow controller, through the second minor chamber if the membrane is determined not to be functioning within predetermined limits.

In certain embodiments, a blood fluid removal system has: (i) a medium housing defining a major chamber; (ii) a blood fluid removal membrane disposed into the media housing and sealing dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second outlet in fluid communication with the second minor chamber, wherein the system is configured such that fluid removed from the blood exits the second minor chamber through the second outlet; (v) a first sensor configured to detect an indicator of a blood waste product at or upstream of the first inlet; (vi) a second sensor configured to detect the indicator of the blood waste product at or downstream of the first outlet; and control electronics configured to acquire data from the sensor and configured to determine whether the membrane is functioning within predetermined parameters based on the acquired data.

In certain embodiments, a system has a control element configured to adjust the pressure differential between the first minor chamber and the second minor chamber, and wherein the control electronics are further configured to cause the control element to adjust the pressure differential based on the data acquired from the first sensor.

In certain embodiments, a system has an alert circuit configured to alert a patient or a healthcare provider, wherein the control electronics are configured to activate the alert circuit if the control electronics determine that membrane is not functioning within the predetermined parameters.

In certain embodiments, a system has (i) a second inlet in communication with the second minor chamber, wherein dialysate is configured to flow through the second inlet and the second outlet; and (ii) a dialysate flow controller operably coupled to the control electronics, wherein control electronics are configured to increase dialysate flow rate, via the dialysate flow controller, through the second minor chamber if the membrane is determined not to be functioning within predetermined limits.

In certain embodiments, a blood fluid removal system has: (i) a medium housing having an inlet and an outlet; (ii) a sorbent configured to adsorb one or more components of blood disposed into the media housing, wherein the system is configured such that a patient's enters the media housing through the inlet and exits the housing via the outlet; (iii) a sensor configured to detect an indicator of fluid flow at or downstream of the outlet; and (iv) control electronics configured to acquire data from the sensor and configured to determine whether the sorbent is functioning within predetermined parameters based on the acquired data.

In certain embodiments, a system has an alert circuit configured to alert a patient or a healthcare provider, wherein the control electronics are configured to activate the alert circuit if the control electronics determine that the sorbent is not functioning within the predetermined parameters.

In certain embodiments, a blood fluid removal or dialysis system has: (i) a medium housing having an inlet and an outlet; (ii) a sorbent configured to adsorb one or more components of blood disposed into the media housing, wherein the system is configured such that a patient's enters the media housing through the inlet and exits the housing via the outlet; (iii)_a first sensor configured to detect an indicator of a blood waste product at or downstream of the outlet; and (iv) control electronics configured to acquire data from the first sensor and configured to determine whether the sorbent is functioning within predetermined parameters based on the acquired data.

In certain embodiments, a system has an alert circuit configured to alert a patient or a healthcare provider, wherein the control electronics are configured to activate the alert circuit if the control electronics determine that sorbent is not functioning within the predetermined parameters.

In certain embodiments, a system has a second sensor configured to detect the indicator of the blood waste product at or upstream of the inlet, wherein the control electronics are configured to acquire data from the second sensor, and wherein the control electronics are configured to compare data acquired from the first sensor to data acquired from the second sensor in determining whether the sorbent is functioning within predetermined parameters.

In certain embodiments, a method has the steps of: (i) monitoring an indicator of a level of a compound in removed fluid or treated blood downstream of the medium; and (ii) determining whether the medium is performing within predetermined parameters based a value of the monitored indicator.

In certain embodiments, a method has the steps of monitoring an indicator of a level of the compound in untreated blood upstream of the medium.

In certain embodiments, determining whether the medium is performing within predetermined parameters has the steps of comparing a value of the monitored indicator obtained upstream of the medium to the value of the monitored indicator obtained downstream of the medium In certain embodiments, a method of determining whether the medium is performing within predetermined parameters has the steps of comparing a value of the monitored indicator obtained upstream of the medium to the value of the monitored indicator obtained downstream of the medium based on the value of the monitored indicator obtained upstream of the medium.

In certain embodiments, a system has: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; and (iii) control electronics in communication with the first sensor, wherein the control electronics are configured to carry out the methods described herein.

In certain embodiments, a system has a computer readable medium that, when executed by the control electronics, cause the control electronics to carry out the methods described herein.

In certain embodiments, a system has: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; (iii) a second sensor upstream of the medium and configured to monitor an indicator of a level of the compound in the untreated blood; (iv) control electronics in communication with the first and second sensors, wherein the control electronics are configured to carry out the methods described herein.

In certain embodiments, a method for monitoring blood fluid removal medium or membrane performance of a blood fluid removal system, the system configured such that untreated blood enters the medium and removed fluid and treated blood exit the medium, has the steps of: (i) monitoring an indicator of a flow rate of removed fluid downstream of the medium; and (ii) determining whether the medium is performing within predetermined parameters based a value of the monitored indicator.

In certain embodiments, a method has the steps of monitoring an indicator of a flow rate of untreated blood upstream of the medium.

In certain embodiments, a method of determining whether a medium or membrane is performing within predetermined parameters has the steps of comparing a value of the monitored indicator obtained upstream of the medium to the value of the monitored indicator obtained downstream of the medium.

In certain embodiments, a method of determining whether a medium or membrane is performing within predetermined parameters has the steps of comparing a value of the monitored indicator obtained upstream of the medium to the value of the monitored indicator obtained downstream of the medium based on the value of the monitored indicator obtained upstream of the medium.

In certain embodiments, a system has: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring a flow rate of removed fluid; (iii) and control electronics in communication with the first sensor, wherein the control electronics are configured to carry out the methods disclosed herein.

In certain embodiments, a system has a computer readable medium that, when executed by the control electronics, cause the control electronics to carry out the methods disclosed herein.

In certain embodiments, a system has: (i) a blood fluid removal medium having an inlet for receiving untreated blood, an outlet through which treated blood is configured to exit, and an outlet through which fluid removed from the blood is configured to exit; (ii) a first sensor downstream of the medium and configured to monitoring an indicator of a level of a compound in removed fluid or treated blood; (iii) a second sensor upstream of the medium and configured to monitor an indicator of a level of the compound in the untreated blood; and (iv) control electronics in communication with the first and second sensors, wherein the control electronics are configured to carry out the methods disclosed herein.

In certain embodiments, a system has a computer readable medium that, when executed by the control electronics, cause the control electronics to carry out the methods disclosed herein.

In certain embodiments, a blood fluid removal or dialysis system has: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) control electronics configured to acquire data from the one or more sensors and configured to determine whether the membrane is functioning within a first predefined range of parameters based on the acquired data; and (vii) a dialysate flow controller operably coupled to the control electronics, wherein the control electronics are configured to increase dialysate flow rate through the second minor chamber, via control of the dialysate flow controller, if the membrane is determined to not be function within the first range.

In certain embodiments, control electronics are further configured to acquire data from the one or more sensors and to determine whether the membrane is functioning within a first predefined range of parameters based on the acquired data at a predetermined amount of time after the dialysate flow rate is increased.

In certain embodiments, control electronics configured (i) to reduce the rate of the dialysate through the second minor chamber at a predetermined time after the flow rate is increased, and (ii) to acquire data from the one or more sensors after the dialysate rate has been reduced and to determine whether the membrane is functioning within a first predefined range of parameters based on the acquired data after the flow rate has been reduced.

In certain embodiments, a blood fluid removal system has: (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) a dialysate flow controller configured to control the rate of dialysate flow rate through the second minor chamber; (vii) control electronics operably coupled to the one or more sensors and to the dialysate flow controller; and (viii) a computer-readable medium comprising instructions that, when implemented, cause the control electronics (i) to acquire data from the one or more sensors, (ii) determine whether the membrane is functioning within a first predefined range of parameters based on the acquired data; and (iii) increase dialysate flow rate through the second minor chamber, via control of the dialysate flow controller, if the membrane is determined to not be function within the first range.

In certain embodiments, a computer readable medium further has the instructions that, when implemented, cause the control electronics (i) to acquire data from the one or more sensors, (ii) and to determine whether the membrane is functioning within a first predefined range of parameters based on the acquired data at a predetermined amount of time after the dialysate flow rate is increased.

In certain embodiments, a computer readable medium has the instructions that, when implemented, cause the control electronics (i) to reduce the rate of the dialysate through the second minor chamber at a predetermined time after the flow rate is increased, (ii) to acquire data from the one or more sensors after the dialysate rate has been reduced, and (iii) to determine whether the membrane is functioning within a first predefined range of parameters based on the acquired data after the flow rate has been reduced.

In certain embodiments, a system has (i) a medium housing defining a major chamber; (ii) a blood fluid removal membrane disposed into the media housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber though the first outlet; (iv) a second inlet and a second outlet in fluid communication with the second minor chamber, wherein the system is configured such that fluid removed from the blood exits the second minor chamber through the second outlet and such that dialysate flows through the second minor chamber from the second inlet to the second outlet; (v) one or more sensors configured to measure a pressure differential across the membrane; (vi) a dialysate flow controller configured to control the rate of dialysate flow rate through the second minor chamber; and (vii) control electronics operably coupled to the one or more sensors and to the dialysate flow controller, the method carried out by the control electronics of the system and comprising: (i) acquiring data from the one or more sensors; (ii) determining whether the membrane is functioning within a first predefined range of parameters based on the acquired data; and (iii) increasing dialysate flow rate through the second minor chamber, via control of the dialysate flow controller, if the membrane is determined to not be function within the first range.

In certain embodiments, a method has the steps of: (i) acquiring data from the one or more sensors; and (ii) determining whether the membrane is functioning within a first predefined range of parameters based on the acquired data at a predetermined amount of time after the dialysate flow rate is increased.

In certain embodiments, a method has the steps of: (i) reducing the rate of the dialysate through the second minor chamber at a predetermined time after the flow rate is increased; (ii) acquiring data from the one or more sensors after the dialysate rate has been reduced; and (iii) determining whether the membrane is functioning within a first predefined range of parameters based on the acquired data after the flow rate has been reduced.

In certain embodiments, a method has the steps of (i) monitoring rate of flow of blood, or an indicator thereof, entering a blood fluid removal device; (ii) determining whether the monitored flow rate or indicator is within a predetermined range; and (iii) adjusting a system parameter of the blood fluid removal device or a blood fluid removal session parameter if the monitored flow rate or indicator is not within the predetermined range.

In certain embodiments, a blood fluid removal or dialysis device comprises a blood flow control element configured to control the rate of flow of blood through the device and wherein adjusting a system parameter comprises adjusting a parameter of a blood flow control element to adjust the rate of flow of blood through the device.

In certain embodiments, a method has the steps of (i) monitoring rate of flow of blood, or an indicator thereof, through the blood fluid removal device; and (ii) determining whether the monitored flow rate or indicator is within a predetermined range.

In certain embodiments, a method of adjusting a system parameter has the steps of adjusting a parameter configured to control rate of fluid removal from the blood.

In certain embodiments, a method of adjusting the parameter configured to control rate of fluid removal from the blood has the step of adjusting the rate of flow of dialysate.

In certain embodiments, a method of adjusting the parameter configured to control rate of fluid removal from the blood has the step of adjusting a pressure differential across a medium configured to remove fluid from the blood.

In certain embodiments, a method of adjusting the session parameter has the step of adjusting the length of time of the session.

In certain embodiments, a method has the steps of (a) initiating a blood fluid removal or dialysis session with initial system parameters; (b) acquiring a first set of data regarding one or more patient physiological parameters; (c) storing the first data set in a most effective to date data set memory; (d) associating the initial system parameters in an increased effectiveness lookup table with the first data set; (e) adjusting at least one parameter of the blood fluid removal session to arrive at adjusted system parameters; (f) acquiring a second set of data regarding the one or more patient physiological parameters after the at least one parameter of the blood fluid removal session has been adjusted; and if at least one value of the second data set is closer to the target value than a corresponding at least one value of the first data set: replacing the first data set in the most effective to date data set memory with the second data set; storing in the increased effectiveness lookup table data regarding the second data set; and associating data regarding the adjusted system parameters with the second data set.

In certain embodiments, a method has the steps of (a) storing the first data set in a least effective to date data set memory; (b) associating the initial system parameters in a decreased effectiveness lookup table with the first data set prior to adjusting the at least one parameter of the blood fluid removal session; and (c) if the at least one value of the second data set is not closer to the target value than the corresponding at least one value of the first data set: replacing the first data set in the least effective to date data set memory with the second data set; storing in the decreased effectiveness lookup table data regarding the second data set; and associating data regarding the adjusted system parameters with the second data set.

In certain embodiments, a method has the steps of (a) further adjusting at least one parameter of the blood fluid removal session to arrive at further adjusted system parameters; (b) acquiring a third set of data regarding the one or more patient physiological parameters after the at least one parameter of the blood fluid removal session has been further adjusted; and (c) if at least one value of the third data set is closer to the target value than a corresponding at least one value stored in the most effective to date data set memory: replacing the data set in the most effective to date data set memory with the third data set; and storing in the increased effectiveness lookup table data regarding the third data set and associating data regarding the further adjusted system parameters with the third data set.

In certain embodiments, a method has the steps of (a) further adjusting at least one parameter of the blood fluid removal session to arrive at further adjusted system parameters; (b) acquiring a fourth set of data regarding the one or more patient physiological parameters after the at least one parameter of the blood fluid removal session has been further adjusted; and (c) if at least one value of the fourth data set is not closer to the target value than a corresponding at least one value stored in the least effective to date data set memory: replacing the data set in the least effective to date data set memory with the fourth data set; and storing in the decreased effectiveness lookup table data regarding the fourth data set and associating data regarding the further adjusted system parameters with the fourth data set.

In certain embodiments, a method has the steps of (a) acquiring a fifth set of data regarding one or more patient physiological parameters; (b) comparing the fifth data set to the increased effectiveness lookup table; and (c) adjusting the system parameters the system parameters associated with the data set stored in the increased effectiveness lookup table if at least one parameter of a data set stored in the increased effectiveness lookup table is within a predetermined range of the fifth data set.

In certain embodiments, a method has the steps of (a) stopping the blood fluid removal session; (b) acquiring a sixth set of data regarding one or more patient physiological parameters; (c) comparing the sixth data set to the increased effectiveness lookup table; and (d) initiating a second blood fluid removal session with the system parameters associated with the data set stored in the increased effectiveness lookup table if at least one parameter of a data set stored in the increased effectiveness lookup table is within a predetermined range of at least one parameter of the sixth data set.

In certain embodiments, the at least one of the one or more patient parameters are selected from the group consisting of blood pressure, heart rate, pH and concentration of an electrolyte.

In certain embodiments, the electrolyte is potassium.

In certain embodiments, the system parameters are one or more of fluid removal rate and concentration of one or more electrolyte.

In certain embodiments, a blood fluid removal system, has (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (e) control electronics comprising memory and a processor, wherein the control electronics are in operable communication with the one or more sensors and are operably coupled to the one or more control elements, wherein the control electronics are configured to carry out a method described herein.

In certain embodiments, the blood fluid removal medium and the control electronics are housed within a blood fluid removal device.

In certain embodiments, a system has a computer readable, wherein the computer readable medium comprises instructions that cause the control electronics to carry out the methods described herein.

In certain embodiments, a blood fluid removal or dialysis system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) initiate a blood fluid removal session with initial system parameters; (ii) acquire a first set of data regarding one or more patient physiological parameters; (iii) store the first data set in a most effective to date data set memory; (iv) associate the initial system parameters in an increased effectiveness lookup table with the first data set; (v) adjust at least one parameter of the blood fluid removal session to arrive at adjusted system parameters; (vi) acquire a second set of data regarding the one or more patient physiological parameters after the at least one parameter of the blood fluid removal session has been adjusted; and (vii) if at least one value of the second data set is closer to the target value than a corresponding at least one value of the first data set: replace the first data set in the most effective to date data set memory with the second data set; store in the increased effectiveness lookup table data regarding the second data set; and associate data regarding the adjusted system parameters with the second data set.

In certain embodiments, a computer-readable medium has the instructions that, when executed by a blood fluid removal or dialysis device, cause the device to (a) initiate a blood fluid removal session with initial system parameters; (b) acquire a first set of data regarding one or more patient physiological parameters; store the first data set in a most effective to date data set memory; (c) associate the initial system parameters in an increased effectiveness lookup table with the first data set; (d) adjust at least one parameter of the blood fluid removal session to arrive at adjusted system parameters; (e) acquire a second set of data regarding the one or more patient physiological parameters after the at least one parameter of the blood fluid removal session has been adjusted; and (f) if a at least one value of the second data set is closer to the target value than a corresponding at least one value of the first data set: replace the first data set in the most effective to date data set memory with the second data set; store in the increased effectiveness lookup table data regarding the second data set; and associate data regarding the adjusted system parameters with the second data set.

In certain embodiments, a method carried out by a blood fluid removal or dialysis system, has the steps of: (a) acquiring data regarding one or more of: (i) one or more patient physiological parameters; and (ii) time since last blood fluid removal session; (b) acquiring data regarding one or more target outcomes of a blood fluid removal session; (c) determining whether at least one of the one or more target outcomes is within a predetermined range of a at least one corresponding prior target outcome stored in a lookup table, wherein the lookup table comprises data regarding system parameters used in one or more prior blood fluid removal sessions of the patient; (d) determining whether the at least one target outcome was achieved with the system parameters used in the prior blood fluid removal session; (e) if the at least one target outcome is determined to have been achieved, determining whether at least one of the patient parameters or time since last blood fluid removal session is within a predetermined range of at least one corresponding parameter stored in the lookup table; and (f) initiating a blood fluid removal session employing the system parameters used the prior blood fluid removal session if the at least one patient parameter or time since last blood fluid removal session is determined to be within a predetermined range.

In certain embodiments, at least one of the one or more patient parameters are selected from the group consisting of blood pressure, heart rate, pH and concentration of an electrolyte.

In certain embodiments, the system parameters have one or more of fluid removal rate and concentration of one or more electrolyte.

In certain embodiments, a blood fluid removal or dialysis system, has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a methods disclosed herein.

In certain embodiments, the blood fluid removal medium and the control electronics are housed within a blood fluid removal device.

In certain embodiments, a system has a computer readable, wherein the computer readable medium comprises instructions that cause the control electronics to carry out the methods described herein.

In certain embodiments, a blood fluid removal or dialysis system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) acquire data regarding one or more of: one or more patient physiological parameters; and time since last blood fluid removal session; (ii) acquire data regarding one or more target outcomes of a blood fluid removal session; (iii) determine whether at least one of the one or more target outcomes is within a predetermined range of a at least one corresponding prior target outcome stored in a lookup table, wherein the lookup table comprises data regarding system parameters used in one or more prior blood fluid removal sessions of the patient; (iv) determine whether the at least one target outcome was achieved with the system parameters used in the prior blood fluid removal session; (v) if the at least one target outcome is determined to have been achieved, determine whether at least one of the patient parameters or time since last blood fluid removal session is within a predetermined range of at least one corresponding parameter stored in the lookup table; and (vi) initiate a blood fluid removal session employing the system parameters used the prior blood fluid removal session if the at least one patient parameter or time since last blood fluid removal session is determined to be within a predetermined range.

In certain embodiments, a computer-readable medium has the instructions that, when executed by a blood fluid removal device, cause the device to (a) acquire data regarding one or more of: one or more patient physiological parameters; and time since last blood fluid removal session; (b) acquire data regarding one or more target outcomes of a blood fluid removal session; (c) determine whether at least one of the one or more target outcomes is within a predetermined range of a at least one corresponding prior target outcome stored in a lookup table, wherein the lookup table comprises data regarding system parameters used in one or more prior blood fluid removal sessions of the patient; (d) determine whether the at least one target outcome was achieved with the system parameters used in the prior blood fluid removal session; (e) if the at least one target outcome is determined to have been achieved, determine whether at least one of the patient parameters or time since last blood fluid removal session is within a predetermined range of at least one corresponding parameter stored in the lookup table; and (f) initiate a blood fluid removal session employing the system parameters used the prior blood fluid removal session if the at least one patient parameter or time since last blood fluid removal session is determined to be within a predetermined range.

In certain embodiments, a method carried out by a blood fluid removal or dialysis system, has the steps of: (a) collecting first data regarding a patient, the data including one or more of a physiological parameter and time since last blood fluid removal session; (b) collecting second data regarding system parameters employed in blood fluid removal sessions of the patient; (c) determining, based on the first and second collected data, whether at least one physiological parameter of the patient improved as a result of the system parameters employed; (d) determining whether a value of current patient data is within a predetermined range of a corresponding value of first collected data; and (e) employing the system parameters that resulted in improvement, if such parameters are determined to exist and if the current patient data is determined to be within the predetermined range.

In certain embodiments, a blood fluid removal or dialysis system, has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a methods disclosed herein.

In certain embodiments, the blood fluid removal medium and the control electronics are housed within a blood fluid removal device.

In certain embodiments, a system has a computer readable, wherein the computer readable medium comprises instructions that cause the control electronics to carry out the methods disclosed herein.

In certain embodiments, a blood fluid removal system has: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient improved as a result of the system parameters employed; (iv) determine whether a value of current patient data is within a predetermined range of a corresponding value of first collected data; and (v) employ the system parameters that resulted in improvement, if such parameters are determined to exist and if the current patient data is determined to be within the predetermined range.

In certain embodiments, a computer-readable medium has the instructions that, when executed by a blood fluid removal device, cause the device to (a) collect first data regarding a patient, the data including one or more of a physiological parameter and time since last blood fluid removal session; (b) collect second data regarding system parameters employed in blood fluid removal sessions of the patient; (c) determine, based on the first and second collected data, whether at least one physiological parameter of the patient improved as a result of the system parameters employed; (d) determine whether a value of current patient data is within a predetermined range of a corresponding value of first collected data; and (e) employ the system parameters that resulted in improvement, if such parameters are determined to exist and if the current patient data is determined to be within the predetermined range.

DETAILED DESCRIPTION OF THE INVENTION

Figure 1:
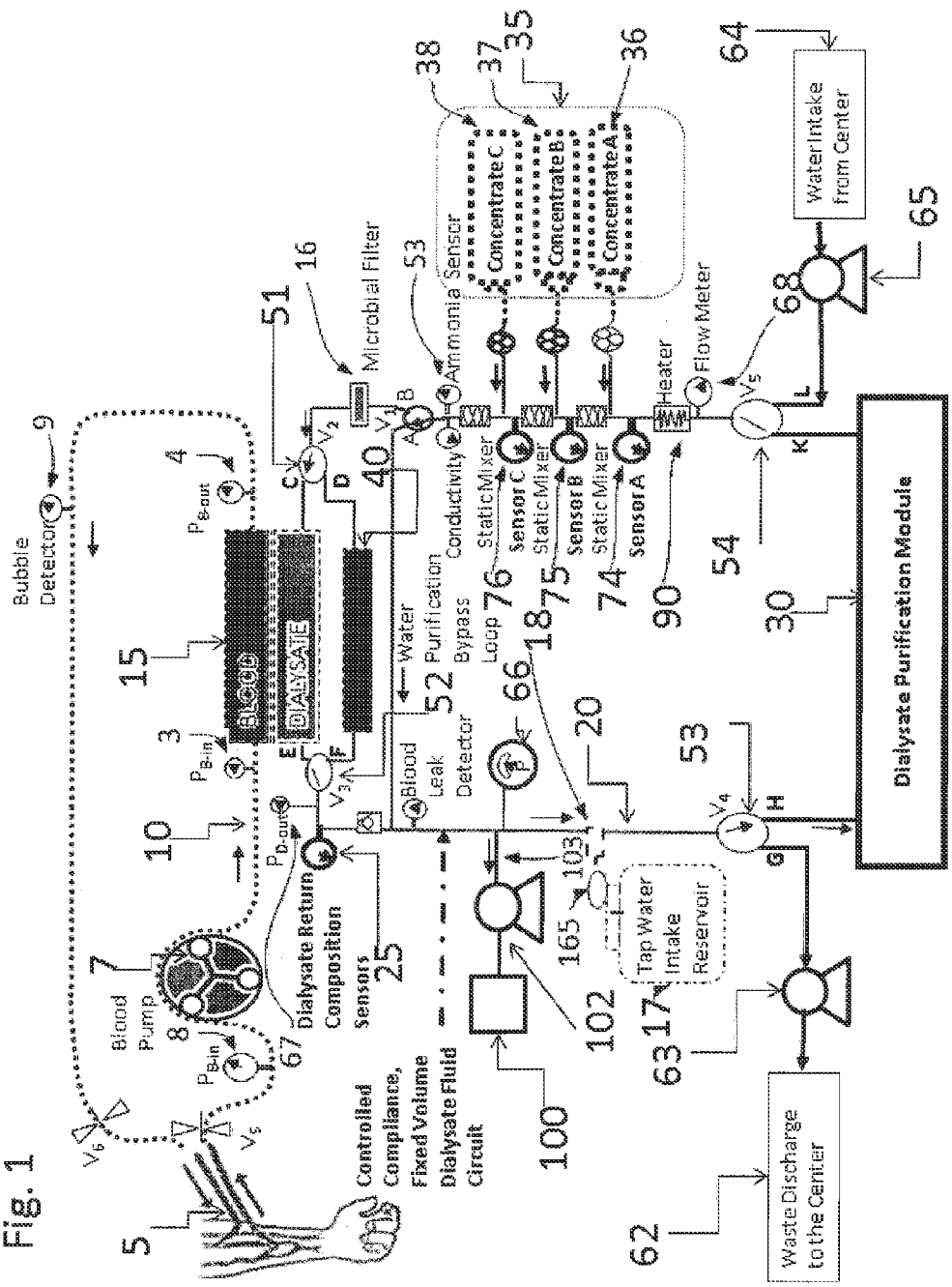
FIG. 1 shows an exemplary embodiment of the invention employed for hemodialysis treatment.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail completely.

The terms "communicate" and "communication" include but are not limited to, the connection of system electrical elements, either directly or remotely, for data transmission among and between said elements. The terms also include, but are not limited, to the connection of system fluid elements enabling fluid interface among and between said elements.

The term "anode" refers to the positively charged electrode.

The term "cathode" refers to the negatively charged electrode.

The term "anion" refers to negatively charged particles that are attracted toward the positive electrode, i.e. anode.

The term "cation" refers to positively charged particles that are attracted toward the negatively charged electrode, i.e. cathode.

The term "electrodialysis" refers to the process of selectively moving electrically charged particles in a solution using externally applied electrical fields and ion selective membranes.

The term "reverse osmosis" refers to the process of selective removal of solutes from a solution with the application of external forces and the use of special membranes.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

A "control system" consists of combinations of components that act together to maintain a system to a desired set of performance specifications. The performance specifications can include sensors and monitoring components, processors, memory and computer components configured to interoperate.

A "controller" or "control unit" is a device which monitors and affects the operational conditions of a given system. The operational conditions are typically referred to as output variables of the system, which can be affected by adjusting certain input variables.

The term "dialysate" describes a fluid into which solutes from a fluid to be dialyzed diffuse through a membrane.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed.

A "dialysis chamber," "hemodialyzer" and "hemodialysis chamber" as used herein is a chamber in which hemodialysis is performed. If no dialysate is present, the dialysis chamber can be used for the bulk transfer of water using a pressure gradient. In that case, the chamber can function as a "hemofiltration chamber." Similarly, if both hemodialysis and hemofiltration, the chamber can function as a "hemodiafiltration chamber."

An "electrodialysis unit" as used herein is a fluid processing unit that removes waste components from effluent dialysate by altering the ionic composition of a fluid. Such units may include electrically conductive plates separated by ion-exchange membranes. Fluid flowing between the plates is exposed to an electrical field. The electrical field induces a rate of ion movement within the fluid corresponding to the magnitude of the voltage potential formed between the electrically conductive plates.

A "dialysate cleansing unit" as used herein is a fluid processing unit that removes waste components from effluent dialysate via sorbent adsorption, electrodialysis, reverse osmosis or similar techniques.

The term "hyperosmotic" pertains to a solution that has a higher solute concentration than another solution. In the human body, a hyperosmotic state refers to a condition caused by the accumulation in the body of significant quantities of osmotically active solutes.

The term "hypoosmotic" pertains to a solution containing a lower concentration of osmotically active components than a standard solution. In the human body, a hypoosmotic state describes a cell that has a lower concentration of solutes than its surroundings.

Osmolarity is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "patient" is a member of any animal species, preferably a mammalian species, optionally a human. The subject can be an apparently healthy individual, an individual suffering from a disease, or an individual being treated for a disease.

The term "programmable" as used herein refers to a device using computer hardware architecture and being capable of carrying out a set of commands, automatically.

The term "sensory unit" refers to an electronic component capable of measuring a property of interest.

The terms "treating" and "treatment" refer to the management and care of a patient having a pathology or condition. Treating includes administering one or more embodiments of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "waste components" as used herein describe waste organic and inorganic components, such as urea, uric acid, creatinine, chlorides, inorganic sulfate and phosphate. Specific "waste components" can vary between individual depending on diet and environmental factors. Hence, the term is intended to encompass any waste component that is normally removed by a kidney or by dialysis without restriction on the specific type of waste substance.

A "portable dialyzer" is a portable artificial dialysis device through which blood is circulated, the dialyzing fluid being regenerated by a system of filters and make-up solids continuously fed to the dialysis fluid. The device may be a continuously operable and externally regenerable dialysis device that is capable of concurrently dialyzing the bodily fluids and regenerating the dialysis fluid outside the body.

Dialysate Regeneration

Dialysate fluid used for hemodialysis contains many of the solutes that are found in body fluids as shown in Table 1. Dialysate fluid used for peritoneal dialysis is similar except $HCO_3^-$ is replaced with lactate at similar concentrations and dextrose is used at much higher concentrations around 2000 mg/dl.

TABLE 1

Typical solute concentrations in dialysate for hemodialysis

| Solute | Concentration |
|---|---|
| Na | 137 mEq/L |
| Cl | 105 mEq/L |
| Ca | 3.0 mEq/L |
| Acetate | 4.0 mEq/L |
| K | 2.0 mEq/L |
| HCO3 | 33 mEq/L |
| Mg | 0.75 mEq/L |
| Dextrose | 200 mg/dl |

The concentrations of the solutes to be removed from the body are lower in the dialysate than in the bodily fluid. For example, the concentration of potassium ion ($K^+$) is typically about 2 mM in the dialysate, while the concentration in the bodily fluid, such as blood, is usually higher, perhaps at about 5 mM. Hence, the mass transfer from the body fluids to the dialysate causes the concentrations of these molecules to increase in the dialysate during a treatment session. The present system removes impurities from dialysate.

Impurities in the fluid dialysate come in two forms: ionic substances and non-charged substances. Ions readily dissolve in water due to the polar nature of water wherein the separation of the ions from the water requires special processes. In particular, removal of ions in the present invention may be accomplished by ion exchange columns, sorbents, electrodialysis, distillation, reverse-osmosis as well as other means known to those of ordinary skill. In particular, electrodialysis and sorbents can be used for the removal of charged ions from the used dialysate in the present invention. However, non-charged or neutral molecules such as urea are generally ineffectively removed from water using electrodialysis unless such non-charged substances are first converted into a charged ionic substance. In certain embodiments, the systems and devices of the present invention remove at least a portion of the daily build-up of 20 grams of urea, 2 grams of creatinine, 4 grams of sodium, 2 grams of potassium and 1 gram of phosphorus, in addition to a few liters of water due to fluid build-up caused by CKD.

In certain embodiments, the present invention employs an electrodialysis unit to remove waste species from the dialysate after treatment. After initial contact between the dialysate and the patient to remove one or more waste species from the patient, the generated spent dialysate is regenerated to remove waste species and/or rebalance dialysate to maintain a composition to allow for proper mass transfer between the patient and the dialysate. In particular, the electrodialysis unit is used as part of a system in certain embodiments to regenerate dialysate for reuse without the primary use of sorbent materials for absorbing urea, ammonia or ammonium ions, such as zirconium phosphate and other zirconium-containing sorbents. In some embodiments, a sorbent material containing zirconium or zirconium can be present, however the use and/or amount of the consumable sorbent material is substantially reduced due to the presence of the electrodialysis unit. The fluid generated by the electrodialysis unit or a purification unit is substantially free from ionic material wherein a dialysate can be regenerated through the addition of buffers, salts and osmotic agents. An activated carbon sorbent can optionally be used to remove common non-ionic waste species such as creatinine. A urease-containing material can be used to convert neutral urea to ammonium ions that are removed by the electrodialysis unit.

The electrodialysis unit can be used in a multimodal fashion for hemodialysis, hemodiafiltration, or peritoneal dialysis. In some embodiments, an extracorporeal or blood circuit passes blood from a patient through a hemodialyzer while a dialysis circuit passes a dialysate through the same hemodialyzer such that waste species pass from the blood to the dialysate to generate spent dialysate. The spent dialysate can then be regenerated for reuse and reentry into the dialysate circuit after treatment with the electrodialysis unit for use in hemodialysis. In other embodiments, a spent dialysate that has been contacted with the peritoneal membrane of a patient is regenerated though use of the electrodialysis unit to remove waste components from the dialysate. Then, the regenerated dialysate can be re-contacted with the peritoneal membrane of the patient to continue peritoneal dialysis.

The invention also provides for an easily portable dialysis system that can be transported to a clinical dialysis center, herein referred to as in-center use or mode. The embodiments of the invention are adaptable to operate with a substantially fixed volume of dialysate wherein the dialysate is continually cleaned by a purification unit and reconstituted to form dialysate and can also operate in a mode wherein dialysate can be generated from purified water provided from a clinical dialysis center (in-clinic mode) without the need for a purification module to clean the dialysate.

Hemodialysis

FIG. 1 shows an exemplary embodiment employing the electrodialysis unit 30 of the invention. A vascular access 5 provides an access to the blood of a patient for extracorporeal processing and return to the patient. The vascular access 5 can be a fistula, a shunt, a catheter or any device or method that allows the transfer of blood between the patient and an extracorporeal system.

The extracorporeal system has a blood loop or circuit 10 consisting of tubing, a blood pump 7 as well as connectors to connect the tubing to the vascular access 5 and to a dialyzer 15. Dialyzer 15 is generally an exchange chamber where fluids and solutes can readily cross a membrane separating the extracorporeal blood and the dialysate. During hemofiltration operation, dialysate is not present on the dialysate side wherein bulk transfer of water takes place under a pressure gradient across a membrane. In certain embodiments, the membrane of dialyzer 15 can be any of a number of hollow fiber-type structures known in the art.

Blood pump 7 can be a peristaltic pump or any other suitable pump known to those of ordinary skill. Sensors in the blood loop or circuit 10 can be used to measure the blood flow rate and the pressure of the blood at various points along the blood loop or circuit 10. One or more pressure sensors can be present to ascertain the pressure within the tubing at different points. In particular, pressure sensors can be present near the vascular access 5 and at the inlet 3 and outlet 4 of the dialyzer 15.

A dialysate loop 20 consists of tubing to carry the dialysate, and valves 51, 52, 53 and 54 direct the dialysate flow. Connectors to water intake 64 and connectors to a waste discharge 62 direct flow via pumps 63 and 65. Connections to a dialysate purification module 30 can also be present along with connectors to the dialyzer 15 and to a flow balance module 40 for diverting dialysate flow away from the dialyzer 15. One or more reservoirs containing an infusate concentrate as well as mixers and sensors 35 (collectively, infusion set) mixes an infusate concentrate with fluid present in the dialysate loop 20.

During hemodialysis operation, dialysate having a physiological compatible composition enters the dialyzer 15 wherein at least one waste component transfers from the blood in the blood circuit 10 to the dialysate circuit 20. The direction of dialysate flow through dialysate circuit 20 is indicated by arrows and the locomotive force for directing the dialysate is provided by pumps present in the electrodialysis unit 30. Valves 51, 52 and 53, located pre- and post-dialyzer 15 can control flow balance through the dialyzer 15. For example, if directing all of the circulation of the dialysis circuit 20 creates an undesirably large pressure within the dialyzer 15, part of the dialysate flow can be diverted through a flow balance unit 40 or a bypass loop 54. One or more sensors can be present along the dialysate circuit 20 to measure pressure and flow rates. FIG. 1 shows pressure sensors 66 and 67 for measuring pressure in the dialysate circuit 20 and flow meter 68 for measuring flow through the dialysate circuit 20.

The dialysate exiting the dialysis unit 15 contains at least one waste species and can be referred to as spent dialysate. The spent dialysate requires purification before being returned to the dialyzer 15. The dialysate purification module 30, which contains an electrodialysis unit, removes ionic species, urea and other uremeic impurities from the dialysate. The fluid emerging from the purification module 30 is substantially deionized and debuffered. Before returning to the dialyzer 15, the fluid is treated by infusion set 35 to add necessary buffer, salts and osmotic control solutes to regenerate a physiologically compatible dialysate. Part of the fluid from the dialysis circuit 20 entering the purification module 30 can be used for the purpose of removing ionic waste species from the purification module 30 and is not returned to the dialysis circuit 20. Water intake 64 and water intake pump 65 can replenish the volume within the dialysis circuit as required. However, a substantial amount of the fluid entering the purification module 30 is returned to the dialysis circuit 20.

In some embodiments, at least about 50% of the fluid entering the purification module 30 is purified for regeneration as dialysate. In other embodiments, at least about 55%, about 58%, about 60%, about 67%, about 70% about 75%, about 77%, about 83%, about 85%, about 89%, or about 95% of the fluid entering the purification module 30 is purified for regeneration as dialysate. In still other embodiments, at least about 97% of the fluid entering the purification module 30 is purified for regeneration as dialysate. In additional embodiments, at least about 99% of the fluid entering the purification module 30 is purified for regeneration as dialysate.

The infusate set 35 can regenerate an appropriate dialysate having a physiologically acceptable concentration of ionic solutes, buffering species as osmolarity. Infusate concentrate reservoirs 36, 37, and 38 can contain solutions for cation salts of $Ca^{2+}$, $Mg^{2+}$ and $K^+$ (typically chloride salts), a biocarbonate buffer and dextrose or other osmotic agent. In certain embodiments, a mixture of cation salts, buffer solution and dextrose are maintained in separate reservoirs, although in other embodiments the concentrates can be combined into fewer reservoirs. As will be further explained below, in some embodiments one of infusate concentrate reservoirs contains a potassium salt in one of reservoirs 37, 37 and 38 not combined with other salts or solutes. The rate of addition of concentrate from reservoirs 36, 37 and 38 can be controlled by pumps 71, 72 and 73. Since the fluid entering the dialysis circuit 20 is substantially solute-free water, in certain embodiments the concentrate solutions are added at a rate that depends upon the concentration of the infusate concentrates and the rate of flow of fluid through the dialysis circuit 20. In certain embodiments, the rate of addition of a potassium salt to the dialysis circuit 20 is adjusted to maintain a constant concentration gradient or rate of mass transfer from the extracorporeal circuit 10 to the dialysis circuit during treatment. Sensors, such as pH, conductivity and ion-selective sensors can be placed along the dialysate circuit 20 to verify that the dialysate has the proper final concentration. Static mixers 74, 75 and 76 can be present to ensure complete mixing of the infusate concentrates.

In certain embodiments, the dialysis circuit 20 can be a controlled compliance dialysis circuit. In addition to diffusion of solutes across the dialysis membrane, a difference in pressure between the blood-side and the dialysate-side of the dialyzer 15 can drive the bulk movement of water from higher pressure to lower pressure. The pressure generated on a particular side of the hemodialyzer depends on several factors including flow rate, viscosity of the fluid, geometry of the dialyzer and the physiological condition of the patient. Control of pressure and the subsequent net movement of water across the dialyzer 15, in general, requires large and expensive equipment to control with a high degree of accuracy. The controlled compliance dialysis circuit embodiment of the present invention provides a means to control the movement of water between the patient and the dialysis circuit 20 and vice versa. In particular, the total void volume of the conduits forming the dialysis circuit have a substantially inflexible volume that prevents the passive inflow and outflow of fluid volume due to pressure changes in the dialyzer 15 that can occur over the course of treatment. This results in a benefit because not all of the pressure changes during treatment are under precise control by a user or operator. That is, under conditions where there is higher pressure on the blood-side of the dialyzer 15, fluid is prevented from uncontrollably migrating into the dialysis circuit due to the controlled compliance volume of the dialysis circuit and water's nature as an uncompressible fluid. Likewise, under conditions where there is a higher pressure on the dialysis circuit 20 side of the dialyzer 15, water cannot uncontrollably migrate to the blood circuit 10 due to the vacuum within the dialysis circuit 20 that would otherwise be created.

Using the controlled compliance dialysis circuit 20 described herein, net movement of water across the dialyzer 15 occurs under active control rather than passively due to pressure differences that develop across the dialysis membrane due to normal operations. In the embodiment shown in FIG. 1, water supplied from intake 64 and pump 65 can be provided to maintain the primed state of the dialysis circuit 20 in the event that less than 100% of the fluid volume exits the purification unit 30 as compared to the fluid entering the purification unit 30. A control pump 102 can be present to access the controlled compliance dialysis circuit 20 through a conduit 103. The control pump 102 can be operated in a manner for controlling the compliance of the dialysis circuit for volume entering the dialysis circuit from the dialyzer 15, where such volume originates from the patient's blood and bodily fluids. The control pump 102 can be operated in an efflux direction that moves fluid from blood side of the dialyzer 15 to the dialysis circuit. That is, operation of the control pump 102 increases the compliance of the dialysis circuit to receive an influx of fluid volume that is moved to a reservoir or drain 100. Through such controlled compliance by control pump 102, net fluid can be removed from the patient to affect ultrafiltration. Due to fluid build-up that occurs in patients having KD, net removal of fluid by ultrafiltration is often desirable.

Similarly, a water intake pump 160 can be operated at a rate to provide an amount of fluid from a water intake 165 that replaces any loss of fluid occurring in the purification module 30. Any additional fluid beyond replacement added to the dialysis circuit 20 can cause a net movement of fluid volume from the control circuit 20 into the blood circuit 10 through the dialyzer 15. As such, the patient can be infused with fluid as need to address hypovolemia or other conditions.

In certain other embodiments, the control pump 102 can be operated at a rate from 0 to about 100 mL/min or 0 to 50 mL/min. Any range from about 0 to about 200 mL/min is contemplated by the invention such as about 15 to about 185 mL/min, about 25 to about 175 mL/min, about 5 to about 75 mL/min, about 61 to about 183 mL/min, about 156 to about 193 mL/min, about 32 to about 63 mL/min, about 145 to about 199 mL/min, about 16 to about 93 mL/min or, about 29 to about 124 mL/min.

All pumps and valves of the system can be under the control of an electronic controller to accurately control the net movement of fluids into and out of the dialysis circuit 20. For example, the electronic controller can control and monitor any pumping rate difference between the control pump 102 and the water intake pump 165 to calculate the net flow of fluid from the blood circuit 10 to the dialysis circuit 20 or from the dialysis circuit 20 to the blood circuit 10 via the dialyzer 15. The electronic controller can also exploit the controlled compliance properties of the dialysis circuit 20 to calculate the amount of fluid removed from the patient by ultrafiltration or infused into the patient during a treatment session. In this light, the electronic controller can also account for the volume added by the infusate set 35 or from the operation of pumps 63 and 65 when the system is operated without the benefit of the purification unit 30, as described herein.

Stand Alone Operation

For stand-alone operation outside of a clinical facility, dialysate flows through the dialysate purification unit 30 using the valves V4 (53) and V5 (54) because large volumes of fresh water or dialysate may not be available outside a clinical facility. In other embodiments, the dialysis circuit 20 can be used at a clinical facility where a supply of fresh dialysate or purified water is available. In such settings, water or dialysate can be introduced through valve 54 through use of pump 65, and after passing through the dialysis unit 15, the dialysate can be discarded at discharge 62 through the operation of pump 63. Furthermore, since the total dialysate volume is fixed during a stand-alone operation, flow balance unit 40 is not needed for standalone operation as may be needed for operation at a clinical center. Therefore, valves V2 [51] and V3 [52] are used to continuously force the dialysate flow over the dialysis unit 15. Table 2 below shows the settings of the valves for the stand-alone operation.

TABLE 2

Positions of valves for stand-alone operation

| Valve | Position |
|-------|----------|
| V2    | C        |
| V3    | E        |
| V4    | H        |
| V5    | K        |

In stand-alone operation, valves 51 and 52 are used to direct the dialysate flow through the dialysis unit 15. As explained in more detail below, during stand alone operation the control pump 102 and the drain/reservoir 100 may be located within the purification module 30 as shown in FIGS. 5-8.

Stand alone operation can also be performed for peritoneal dialysis, wherein the dialysis circuit 20 transports dialysate to and from the peritoneal cavity of a patient rather than a hemodialyzer. That is, the operative set-up for use in peritoneal dialysis mode is substantially the same as in FIG. 1, except the peritoneal cavity of the patient replaces the dialyzer 15 and the blood circuit 10 is not required.

Operation at a Dialysis Center

For operation at a dialysis center, water intake (or dialysate) from the clinical center 64, water intake pump 65, water discharge to the center 62 and the water discharge pump 63 can be present. Hence, there is no requirement for dialysate flow to go through the purification module 30 wherein valves V4 [63] and V5 [54] can be set to bypass the purification module 30.

Once the dialysate is pumped through one circuit of the dialysate circuit 20 by the pumps 63 and 65, there is a possibility that the total volume of dialysate may not be fixed due to a differential in flow rate between pumps 63 and 65. Specifically, any difference in the flow rates of the pumps 63 and 65 can result in the changes in the dialysate volume. Due to the controlled compliance properties of the dialysate circuit 20 described above for some embodiments, a change in dialysate volume will cause a net flow from the blood circuit 10, and hence fluid removal from the patient across the dialyzer 15 or vice versa. For example, if the pump 65 has a slightly higher rate of flow than the pump 63, then there will be surplus of fluid in the dialysate loop 20. This fluid will flow into the patient across the dialyzer 15 increasing the fluid content in the body of the patient. As such, hypovolemia of the patient can be directly addressed; however, fluid infusion of the patient is an undesirable in many scenarios since patients with kidney failure cannot effectively eliminate fluid. When the pump 65 has a flow rate lower than the pump 63, ultrafiltration and fluid removal from the patient can be achieved. However, care must be taken to avoid the removal of too much fluid from the patient.

In lieu of modification of the pump rates of pumps 65 and 63 to address fluid movement across the dialyzer 15, the above-described problem can be addressed using a flow balance module, where the dialysate flow is periodically shunted away from the hemodialysis unit 15 and instead forced to flow over a flow balance unit 40. With valves 51 and 52 actuated to allow access to the flow balance unit 40, no net flow from the dialysate loop 20 to blood loop 10 or vice versa occurs.

In particular, any difference in the flow rates of the pumps 63 and pump 65 would manifest itself as a change in the pressure as a function of time, which can be detected by the pressure sensor 66 when dialysate is flowing through flow balance unit 40. Dialysate can periodically be diverted through the flow balance unit 40 to verify that no difference in flow rates between pumps 63 and 65 is present and/or to make adjustments to the flow rates of pumps 63 and 65. In response to a measured change in pressure at pressure sensor 66, the electronic controller can adjust the power to the motors driving the pumps 63 and 65 to rectify any flow mismatch. For example, if the pressure measured by the pressure sensor 66 shows a trend upwards during the period when the dialysate is flowing over the flow balance unit 40, electronic controller can either reduce the power to the motor driving the pump 65 or increase the power to the motor driving the pump 63. Similarly, if a negative pressure trend is observed during the period when the dialysate is flowing over the flow balance unit 40, the electronic controller can be adjusted by either increasing the power to the motor driving the pump 65 or by decreasing the power to the motor driving the pump 63. In either case, the dialysate flow can be returned back to the dialyzer 15 from the flow balance unit 40 after periodic adjustment. Control pump 102 and drain/reservoir 100 can be present to perform ultrafiltration and fluid removal from the patient in the state where no flow rate difference exists between pump 63 and 65.

Therefore, valves V2 [51] and V3 [52] can be used to switch the dialysate flow between the dialyzer 15 and the flow balance unit 40, while valves V4 [53] and V5 [54] can maintain the dialysate flow bypassing the purification unit 30 for in-clinic operation. Furthermore, since the purification module 30 is not utilized, the control pump 100 and the reservoir/drain 102 can be employed as depicted in FIG. 1. Table 3 below shows the settings of the valves during in-clinic operation.

TABLE 3

Positions of valves for operation at a clinical center

| Valve | Position for dialysis | Position for flow balance |
|---|---|---|
| V2 | C | D |
| V3 | E | F |
| V4 | G | G |
| V5 | L | L |

Potassium Control

In certain embodiments, the concentration of potassium ions is actively controlled to maintain a steady gradient between the serum potassium concentration of the patient's blood and the potassium concentration of the dialysate introduced to the dialyzer 15. Due to the action of the sodium-potassium pump, the vast majority of potassium in the body is present intracellularly. However, dialysis, whether hemodialysis or peritoneal dialysis, can only access or remove potassium that is located extracellularly in the interstitial fluid between cells, which equilibrates with the blood serum. As dialysis functions to remove potassium ions from the blood serum as a result of a concentration gradient between the patient's blood serum and the dialysate, additional potassium ions are drawn out from cells into the intracellular fluids to provide for further removal of potassium ions.

Since potassium ion can readily diffuse across a dialysis membrane, the removal of potassium that occurs during a dialysis session is dependent upon the movement of potassium ions from the intracellular space to extracellular fluids. However, the movement of potassium ions from inside cells to the extracellular fluids is not consistent in all patients. In particular, acid-base balance can affect the influx and efflux of potassium ions from cells. Tonicity, glucose and insulin concentrations and catecholamine activity also affect the balance of potassium between cells and the extracellular fluid.

Figure 2:
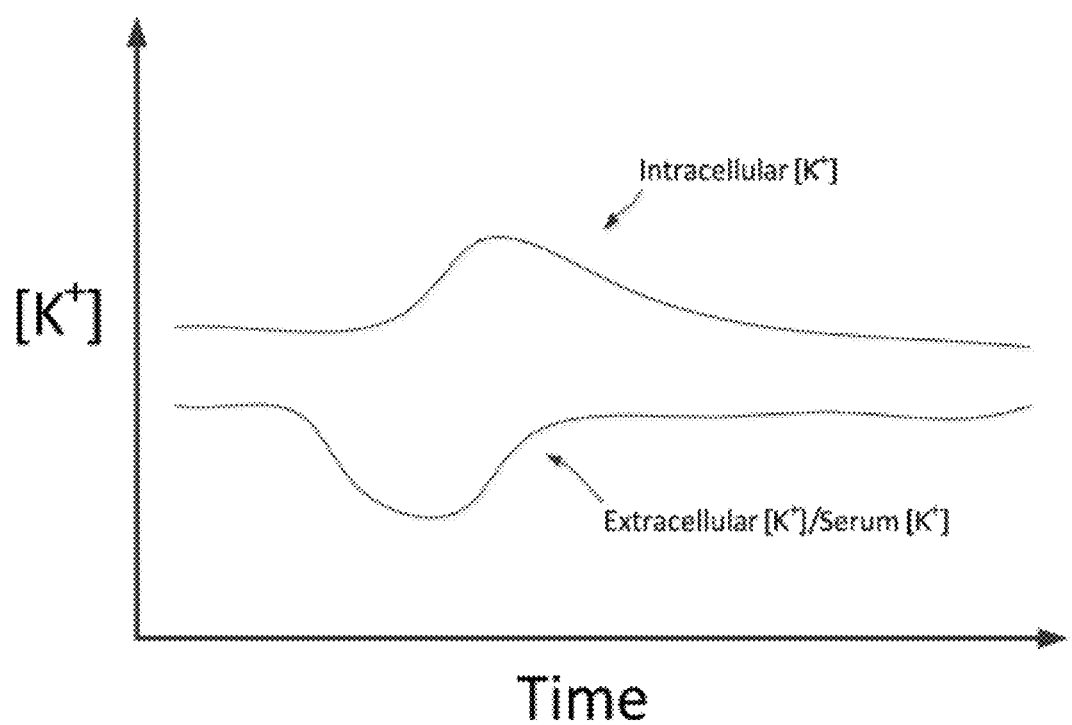
FIG. 2 shows a shift in intracellular and extracellular potassium ion concentrations at the beginning of a dialysis treatment.

Patients can experience slight alkalosis during the beginning of dialysis treatment, which can persist during a multi-hour dialysis treatment. Alkalosis is caused by bicarbonate present in the dialysate to act as a pH buffer. As shown in FIG. 2, a typical patient can experience a drop in serum potassium ion concentration at the beginning of dialysis due to a shift of potassium ions into the cells. Serum potassium ion concentration decreases readily at the beginning of dialysis during typical treatment regimens where the potassium ion concentration in the dialysate remains constant during treatment. After the conclusion of a dialysis treatment, potassium ions can efflux from the cells into the extracellular fluid. The changes that can occur in serum potassium concentrations during and after dialysis treatment can contribute to arrhythmias and other undesirable outcomes.

The rate of potassium removal is not uniform during dialysis wherein a constant concentration of sodium ion in the dialysate is maintained during treatment. Rather, the rate of potassium removal is dependent upon bicarbonate uptake of the patient, the particular time-point during treatment, and several other factors that make the removal of potassium ion unpredictable. As such, the amount of potassium ion removed during dialysis is often limited, which can affect the treatment of hyperkalemia by dialysis. As described herein, in some embodiments the concentration of potassium ion in the dialysate is modified during treatment to maintain one or more of: 1) a substantially constant concentration gradient during dialysis between the patient's blood and the dialysate, and 2) a substantially constant rate of mass transfer of potassium ions between the patient's blood and the dialysate during treatment. As such, the rate of potassium removal will become predictable based upon the length of dialysis regardless of carbonate uptake or other parameters that can affect the distribution of potassium ions between the extracellular space and intracellular cellular space.

In some embodiments, an electronic controller can calculate the amount of potassium ions removed from a patient during treatment. The concentration of potassium ions in the dialysate can be adjusted during treatment to slow or stop the removal of potassium ions during treatment if desired.

With reference to FIG. 1, fluid entering the dialysate loop 20 from the purification unit 30 or the water intake 64 is substantially free from dissolved ions and has a low conductivity. As such, the reconstitution of the dialysate by infusion set 35 can be readily controlled by the electronic controller. In some embodiments, the rate of addition of a potassium-containing salt can be controlled separately from other components of the dialysate such as sodium ions, calcium ions or bicarbonate buffer. As such, in one embodiment, a potassium salt, such as potassium chloride, can be present in concentrate infusion reservoir 36 and added to the dialysate circuit 20 through use of infusion pump 31, which is controlled by the electronic controller.

A property of the fluid entering dialysis circuit 20 can be measured by a sensor 74. The sensor 74 can be a conductivity sensor or a potassium-sensitive electrode. The structure of a potassium-sensitive membrane is not particularly limited; however, in some embodiments the potassium-sensitive electrode contains an ion-exchange polymer membrane impregnated with valinomycin or another macrocylic compound selective for transporting potassium ions. Sensor 76 further can be a conductivity or a potassium-sensitive electrode and can measure the dialysate after addition of a potassium salt. Suitable potassium-sensitive electrodes include model 9319BN (Thermo Scientific Inc.) and amperometric sensors described in A. S. Lima et al, "An Electrochemical Sensor Based on Nanostructure Hollandite-type Manganese Oxide for Detection of Potassium Ion," Sensors 9:6613-25 (2009), which is incorporated herein by reference. Where sensors 74 and 75 are conductivity sensors, the difference in conductivity measured between sensors 75 and 74 can be used by the electronic controller to calculate the potassium ion concentration added by infusion set 35 given the known molar conductivity of the potassium-containing salt and temperature of the dialysate. Similarly, where sensors 75 and 74 are potassium-sensitive electrodes, the change in concentration of potassium ion can be directly calculated by the electronic controller.

In some embodiments, the amount of potassium added by infusion set 35 is not determined and none of sensors 74, 75 and 76 are employed to determine a potassium ion concentration of the dialysate prior to contact with the dialyzer 15 or the patient in the case of peritoneal dialysis. Rather, a low conductivity of the fluid entering the dialysis loop 20 provides a determination that no significant amount of potassium ion concentration is entering the dialysis loop 20. As such, the concentration of potassium ions in the dialysate traveling to dialyzer 15 and/or the patient is determinable from known concentration of potassium salt in one or more of concentration reservoirs 36, 37 and 38 and the pumping rate of one or more of infusate pumps 74, 75 and 76.

In one embodiment, the amount of potassium ion added by the infusion set 35 is calculated by the electronic controller such that the concentration of potassium ion in the dialysate is known and the concentration of potassium ions in the spent dialysate after contact with the dialysis chamber 15 and/or the patient is measured by a return dialysate sensor 25. As such, the amount of potassium ions passing from the blood of a patient to the dialysate in the dialysis loop 20 can be calculated by the electronic controller.

In certain embodiments, the return dialysate sensor 25 is a potassium-sensitive electrode and the concentration of potassium ions in the spent dialysate can be directly calculated by a potential measured by the potassium-sensitive electrode. The difference between the known concentration of potassium ions in the dialysate prior to contact with the dialyzer 15 and/or the patient and the concentration in the spent dialysate measured by return dialysate sensor 25 allows for a direct calculation of mass transfer of potassium ions between the patient and the dialysate. As described, the mass transfer of potassium ions can be calculated based upon the measurement of the return dialysate sensor 25 wherein the potassium concentration of the dialysate used for dialysis is controlled by electronic controller providing for the infusion of a potassium salt infusate at a known rate.

In certain embodiments, the system can be used to perform ultrafiltration through the use of control pump 102. During the performance of ultrafiltration, the flow rate of dialysate traveling toward the dialysis chamber 15 and/or patient is slower than the amount of dialysate traveling past the return dialysate sensor 25. The difference in flow rates represents the rate of ultrafiltration or fluid removal from the patient. The electronic controller can account for the dilution of potassium ion concentration caused by bulk fluid transfer between the patient and the dialysis circuit 20. That is, the electronic controller can calculate mass transfer based upon the potential sensed by the return dialysate sensor 25 combined with the flow rate of the dialysate pre- and post-contact with the hemodialysis unit 15 and/or the patient. As such, the equivalents of potassium ion removed from the patient per unit of time can be readily calculated by the electronic controller. As described above, the controlled compliance properties of the dialysate circuit 20 allow for the control of dialysate flow rates in the dialysis circuit 20, and hence allow for the mass transfer of potassium ions to be calculated.

Figure 3:
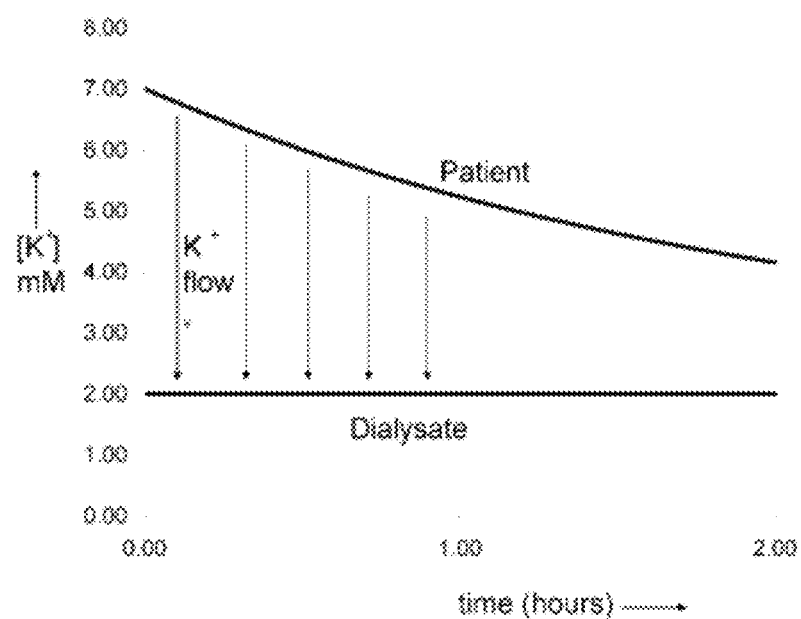
FIG. 3 shows an exemplary change in potassium ion concentration during an exemplary dialysis treatment with a constant dialysate concentration.

The electronic controller can adjust the potassium ion concentration of the dialysate to maintain a constant mass transfer of potassium over the course of treatment. As such, the rate of change in serum potassium ion concentration over time can be substantially equalized over the course of treatment. FIG. 3 shows an exemplary change in serum potassium concentration during dialysis (dashed line) with a dialysate having a constant concentration of potassium over time. As can be seen in FIG. 3, the gradient between the blood serum and the dialysate is largest at the beginning of dialysis that leads to a larger rate of potassium decline in the blood serum at the beginning of dialysis compared toward the end of a typical 4-hour dialysis session.

As shown in FIG. 3, a patient with a serum potassium concentration of 7 mM at the beginning of treatment has a serum potassium concentration that is decreased to about 4.2 mM at the end of the dialysis session. The rate of flow of potassium ions (mass transfer rate) is a function of the ion concentration gradient across the dialyzer membrane, which varies from 5 mM at the onset of the dialysis session to 2.2 mM at the end of the session. Consequently, there is a high rate of removal of potassium (high mass transfer rate) at the beginning of the session, while the rate of removal is about half of the initial value at the end of the two hour period illustrated in FIG. 3. The high rate of potassium removal at the beginning of treatment can cause complications for the patient, since rapid change in serum potassium levels can be compounded by an increase in the uptake of potassium ions by the cells as the serum bicarbonate levels increase. Toward the end of the dialysis session, there is a lower differential between the serum and the dialysate potassium concentrations resulting in a slow rate of potassium ion removal.

The amount of decline in blood serum potassium concentration is directly related to the mass transfer of potassium ions from the blood to the dialysate. As such, control of the mass transfer of potassium ions can be used to modify the rate of potassium concentration decline in the patient's blood. As such, the risk of arrhythmias due to rapid changes in serum potassium can be minimized. The systems described herein allow for the mass transfer of potassium to be calculated without knowing factors such as the actual potassium serum level of the patient, the diffusive permeability of the dialysis membrane or the intracellular/extracellular balance of potassium within the patient.

Figure 4:
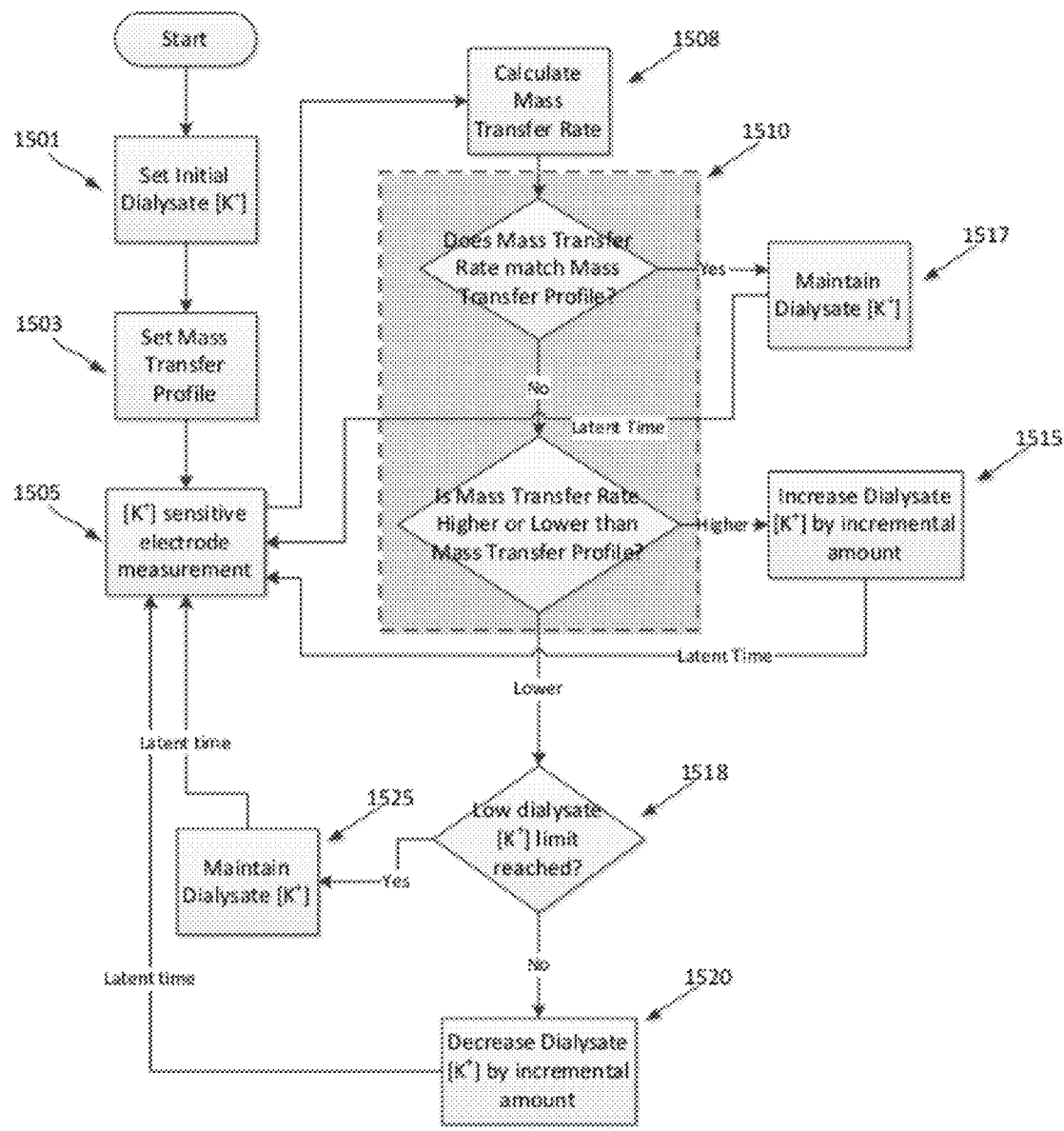
FIG. 4 shows an exemplary methodology for adjusting dialysate composition during treatment in accordance with some embodiments.

As shown in FIG. 4, an initial dialysate potassium concentration can be programmed in set 1501. The initial dialysate potassium concentration can be set based upon the expected potassium state of the patient. However, it should be noted that the initial dialysate potassium concentration can generally be higher than the level used for constant dialysate applications as exemplified in Table 1. In step 1503, a potassium mass transfer profile can be programmed into the electronic controller. In some embodiments, the mass transfer profile can be a constant rate of mass transfer throughout a period of dialysis treatment. In other embodiments, the mass transfer profile can vary the rate of mass transfer over a dialysis time period, or the dialysate potassium concentration can be set to not go below a preset limit. In some embodiments, the mass transfer profile can be set to zero where the dialysate potassium ion concentration can be set to match the blood serum concentration to effect zero net removal.

In step 1505, the potassium-sensitive electrode in the dialysate return sensor 25 measures an electrical signal dependent upon potassium concentration in the spent dialysate. In step 1508, the rate of mass transfer of potassium ions per unit time is calculated. In step 1510, the calculated rate of mass transfer of potassium ions is compared to the mass transfer profile, as shown within the dashed box shown in FIG. 4. If the mass transfer rate matches the mass transfer profile in step 1510, then the dialysate potassium concentration is maintained in step 1517 and after a latency time the composition of the spent dialysate is continually monitored in step 1505. If the mass transfer rate in step 1510 is higher than the mass transfer profile, then in step 1515 the potassium concentration of the dialysate is increased by increasing the rate of potassium salt addition by the infusion set 35 by an incremental amount to reduce the concentration gradient of potassium ions between the patient and the dialysate. If the mass transfer rate in step 1510 is lower than the mass transfer profile, then in step 1518 the current potassium concentration of the dialysate is compared against a lower limit. The concentration of the patient's blood serum cannot decrease to be less than the potassium ion concentration of the dialysate. As such, step 1518 can be used as a check to ensure that the blood serum is not brought to a potassium concentration below a preset limit. If the limit has been reached in step 1518, then the potassium concentration of the dialysate is maintained in step 1525. If the limit has not been reached in step 1518, then the rate of potassium salt infusion by infusion set 35 is decreased by an incremental amount to increase the potassium concentration gradient between the patient and the dialysate.

After the dialysate potassium concentration is appropriately maintained or adjusted, a latency time is elapsed prior to continuing to monitor the potassium concentration in the spent dialysate in step 1505. Due to the rapid circulation of the dialysate through the dialysis circuit 20, the latency period can be short. As such, the rate of potassium salt addition to the dialysate can be quickly adjusted to match the mass transfer profile programmed in step 1503. In some embodiments, the latency period is from about 15 seconds to about 3 minutes. In other embodiments, the latency period is form about 30 seconds to about 5 minutes.

Figure 5:
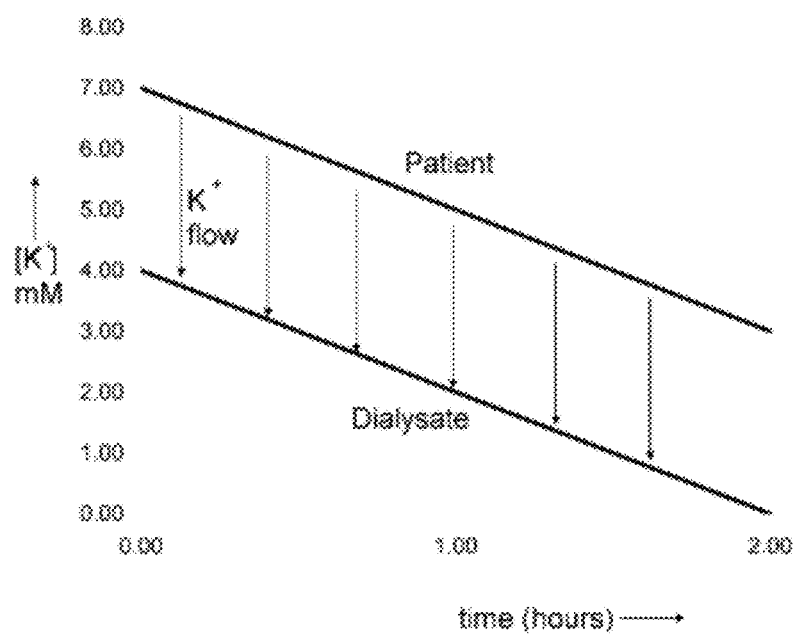
FIG. 5 shows an exemplary change in potassium ion concentration during a dialysis treatment with an adjustable dialysate concentration.

FIG. 5 shows a hypothetical dialysis treatment wherein the potassium ion concentration of the dialysate is varied in the manner outlined in FIG. 4. FIG. 5 shows a mass transfer profile that is constant throughout the treatment. The potassium ion concentration gradient between the plasma and the dialysate (AC) is proportional to the rate of mass transfer of potassium ions. The process of FIG. 5 allows for the dialysate potassium concentration to be iteratively adjusted to maintain a AC that provides the desired rate of mass transfer. However, it should be noted that the proportionality between AC and the rate of mass transfer is not necessarily constant over all concentration ranges.

As shown in FIG. 5, a constant gradient, for example, of about 3 mM can be maintained between the potassium levels in the serum and in the dialysate. At the beginning of the dialysis treatment, the dialysate potassium level can be high, for example, 4 mM. At the end of the two-hour period illustrated, the dialysate concentration of potassium can be brought to zero while the serum level for potassium ions is decreased to about 3 mM. As such, the following benefits can be obtained: (a) by prevention of the rapid decrease of potassium ion concentration, cellular uptake of potassium can be reduced; (b) as a consequence of (a) more potassium can be removed during a treatment session; and (c) the amount of potassium infusate used during treatment can be reduced as a consequence of low potassium ion dialysate levels at the end of treatment.

In another embodiment, the dialysate composition return sensor 25 can be removed from the system and an optional blood composition sensor 26 can be present in the blood circuit 10 as shown in FIG. 1. The blood composition sensor 26 preferably measures the potassium ion concentration in the blood prior to dialysis in dialyzer 15. The blood composition sensor 26 can have the same structure and components as the dialysate return composition sensor 25. In some embodiments, the dialysate return sensor 25 and the blood composition sensor 26 can both be present.

As described above, the use of the dialysate return composition sensor 25 can be used to accurately control potassium mass transfer. The amount of mass transfer observed and the current potassium ion concentration of the dialysate can be used by the electronic controller to estimate the potassium ion concentration in the blood. However, the blood potassium ion composition can be directly measured by the blood composition sensor 26 wherein the dialysate potassium concentration is iteratively modified to adjust the rate of the decrease in blood potassium concentration over time. That is, the rate of potassium salt infusion into the dialysate can be adjusted based upon the measurement made by the blood composition sensor 26 in an iterative fashion, as described above, to reach a desired rate of serum potassium ion concentration change.

Operation of the Dialysate Purification Module

Figure 6:
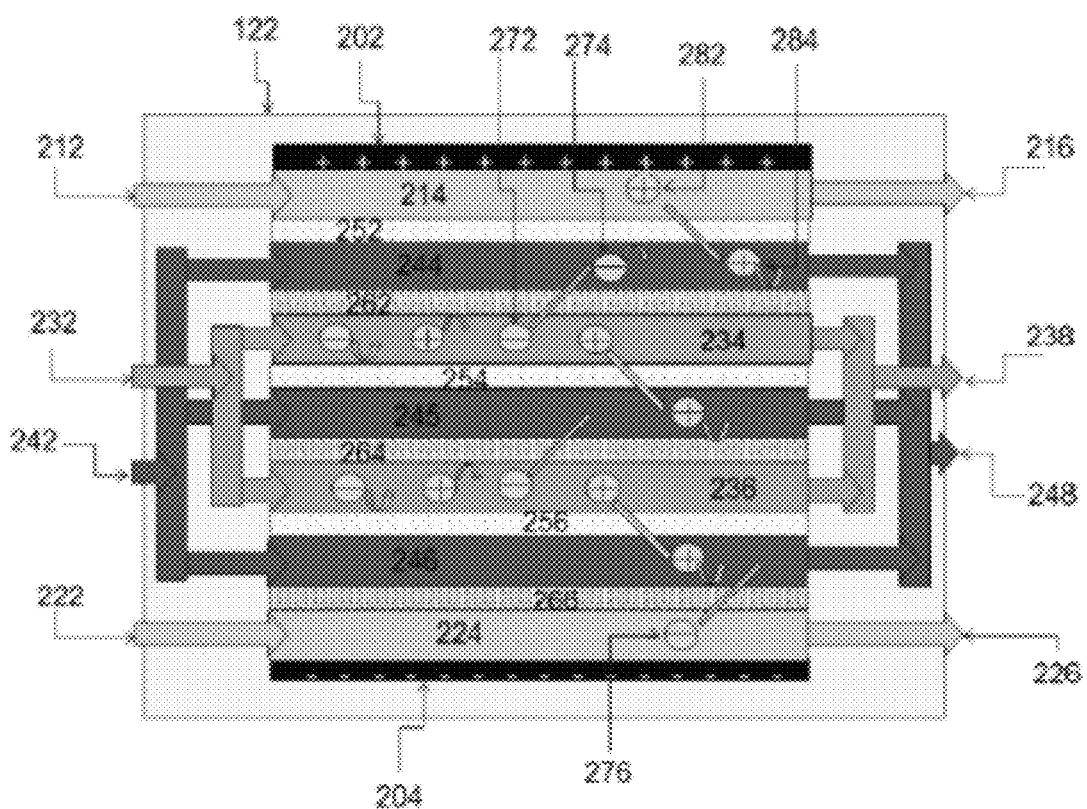
FIG. 6 shows a schematic for an embodiment of an electrodialysis unit.

The purification module 30 purifies the incoming dialysate and readies it to be reconstituted using the concentrate infusion set 35 to form regenerated dialysate, as described above. An exemplary operation of the electrodialysis unit 122 is shown in FIG. 6. Electrodialysis unit 122 is constructed as a multi-chamber flow device where the fluid flow through all chambers is substantially perpendicular to the applied electrical field. An electrical field can be applied using a pair of electrodes, an anode 202 and a cathode 204. Therefore, in FIG. 6, the produced electrical field is oriented in a direction from anode 202 to cathode 204. As a result of the presence of the electrical field, positively charged particles, such as 282 and 284 experience a force toward the cathode 204. Similarly, negatively charged particles, such as 272, 274 and 276 experience a force toward the anode 202.

The function of the electrodialysis unit 122 is to selectively move the charged species, i.e. ions, from one set of chambers to another, thereby reducing the concentration of the ions in a fluid that can be reconstituted and used again as a dialysate. That is, an electrodialysis unit has at least two chambers. A diluate chamber becomes depleted in anions and cations due to operation of the electrodialysis unit 122. The fluid passing through the diluate chamber can then be reconstituted as a dialysate. The remaining chamber is a concentrate chamber that becomes enriched in cations and anions through operation of the electrodialysis unit 122. In certain embodiments, at least two concentrate chambers are present, where one concentrate chamber becomes enriched in cations and the other concentrate chamber becomes enriched in anions.

FIG. 6 presents one embodiment of an electrodialysis unit 122. Movement of the ions in the electrodialysis unit 122 occurs in three set of compartments. The two compartments that are in contact with the anode 202 and cathode 204 are the compartments 214 and 224, respectively. Compartments 214 and 224 are concentrate compartments having a concentrate solution provided therein as described above. However, the solution flowing through compartments 214 and 224 can also be referred to as electrode rinse solutions that enter these two compartments through the ports 212 and 222, respectively. The electrode rinse solutions exit through ports 216 and 226. For charge balance, the electrode rinse solutions can be mixed with each other, or with the solutions in the other chambers.

The dialysate to be regenerated flows into the electrodialysis unit 122 via the intake port 232 and flows into the diluate chambers 234 and 236. Ultimately, the ion concentration in the diluate chambers 234 and 236 is reduced and the ion depleted solution or diluate exits the electrodialysis unit via the port 238. This diluate leaving the electrodialysis via port 238 is used for the regeneration of the dialysate. Ions leaving the diluate are accumulated in the concentrate chambers 244, 245 and 246. The concentrate fluid is circulated using an external pump 112, where the concentrate solution is removed from the electrodialysis unit 122 via the exit port 248 and reintroduced back into the electrodialysis unit via the port 242. That is, at least part of the concentrate solution re-circulates through the electrodialysis unit 122. Although FIG. 6 shows two diluate chambers 234 and 236 and three concentrate chambers 244, 245 and 246, the number of chambers for each can vary from 1 to 100, but not necessarily in equal numbers. Further, the electrode chambers 214 and 224 can serve as concentrate chambers. An increased number of chambers increases the surface area, and therefore the efficiency of the electrodialysis unit 122.

FIG. 6 also shows that the electrode rinse solutions, the diluate solution and the concentrate solution are separated by ion selective membranes. Specifically, the cation-selective membranes 252, 254 and 256 allow the passage of only the positively charged cations. Similarly, the anion-selective membranes 262, 264 and 266 allow the passage of only the negatively charged anions. As shown in FIG. 6, cations, such as 282, move toward the cathode 204 until they encounter an anion-selective membrane such as 262. Similarly, the anions, such as 276, move toward the anode until they encounter a cation membrane such as 256. Ultimately, about 90% of the ionic species are moved from a diluate chamber into a concentrate chamber.

Figure 7:
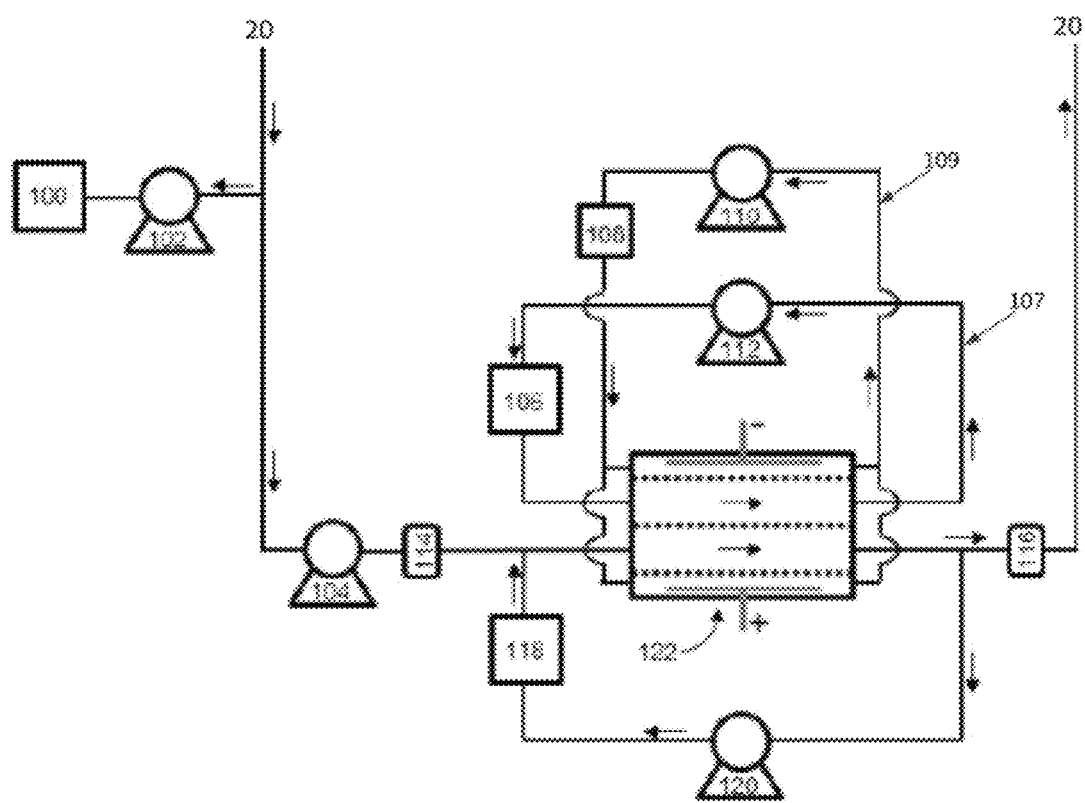
FIG. 7 shows a schematic for an embodiment of a purification module in accordance with some embodiments.

FIG. 7 shows an embodiment of a purification unit 30 for regenerating dialysate. In the embodiment shown in FIG. 7, three separate reservoirs 108, 106 and 118 are used along with pumps 110, 112 and 120 to circulate an electrode rinse solution, a concentrate solution and a diluate solution, respectively. Again, the diluate solution is the solution used for the regeneration of the dialysate. In some embodiments, the diluate solution is re-circulated via the pump 120 to increase the flow rate of the diluate over and beyond the flow rate of the dialysate within the dialysate loop 20, which is circulated via the pump 104 through the dialysate loop 20. Typical ranges for the volumes of the electrode rinse solution and concentrate solutions provided are 100-5,000 mL. Typical ranges of flow rates for the electrode rinse solution, the concentrate and the diluate solutions are 100-10,000 mL/min. In some embodiments, the system contains from about 2 to about 6 L of aqueous-based fluid. In other embodiments, the system contains any of from about 2 to about 10 L, from about 1.5 to about 5 L, from about 2 to about 8 L, or from about 2 to about 5 L of aqueous-based fluid.

A primary conditioning unit 114 is placed before the electrodialysis unit 122 to contact spent dialysate before it enters the electrodialysis unit 122. The primary conditioning unit 114 converts the urea, a neutral molecule, into ammonium ($NH_4^+$), an ionic species. This conversion may take place through various means, including electrical, optical, thermodynamic or chemical processes. For the case of chemical processing of urea, the catalytic enzyme urease can be used to convert urea into ammonium. The ammonium ions then enter into the electrodialysis 122 via the intake portal 232 of the electrodialysis unit 122, as shown in FIG. 6, and removed through the action of the electrical field. The primary conditioning unit 114 can also contain activated carbon for the removal of creatinine and uric acid from the dialysate, which are neutral or substantially neutral species at typical pH values for the dialysate. The primary conditioning unit 114 can also contain ion-exchange resin to remove $Ca^{2+}$ and $Mg^{2+}$, which may minimize membrane fouling due to precipitation and increase the membrane life in the electrodialysis unit.

As shown in FIG. 7, the concentrate solution and electrode solution are recirculated by pumps 110 and 112, respectively. During operation of the electrodialysis unit 122, the concentration of waste species within the recirculating concentrate solution and electrode solution increases with time. When particularly high concentrations of waste species build-up in the concentrate solution and the electrode solution, the operation of the electrodialysis unit 122 can be affected. As such, reservoirs 108 and 106 can contain a volume of concentrate solution and electrode solution, respectively, such that waste impurities will not build up to an inoperable level during a typical treatment session. That is, volumes of concentrate solution and electrode solution are provided such that the transfer of substantially all of the urea, which is the primary waste species, from a patient in one transfer session (approx. 20 grams) will not adversely affect the operation of the electrodialysis unit 122.

An additional conditioning unit 116 can be present at an outlet of the electrodialysis unit 122 that can contain activated carbon or another sorbent to remove non-ionic waste species. Further, the additional conditioning unit 116 can contain a sorbent to absorb ammonium ions, such as zirconium phosphate or another zirconium-containing sorbents. The electrodialysis unit 122, in some instances, may not remove all of the ammonium ions from the diluate solution. As such, residual ammonium ions can be removed by conditioning unit 116. Zirconium phosphate and other zirconium-containing sorbents are expensive consumable materials. As such, the use of electrodialysis unit 122 to remove the large majority of ammonium ions generated from urea in conjunction with conditioning unit 116 consumes less than 10% of the ammonium sorbents compared to systems relying solely upon zirconium phosphate or other zirconium-containing sorbents to remove ammonium ions. In conditioning unit 116, a cation exchange resin or a mixed-bed cation/anion exchange resin can also be present to remove other residual ions and substances (e.g. $Na^+$, $K^+$, $Mg^{2+}$, $Ca^{2+}$).

Although the electrodialysis unit 122 of the purification unit 30 can remove up to 90% of the ions from solution, remaining ions may need to be removed using the sorbents in additional conditioning 116, as explained above. However, there is a possibility of ions to be returned to the dialysate circuit 20. As such, sensors 74, 75 and 76 located in the dialysis circuit 20 and the infusate set 35 can be used to determine the ionic concentration of the fluid reentering the dialysate loop, where the electronic controller can then infuse a reduced amount of infusate solutions into the dialyzer circuit 20 to achieve a desired dialysate composition. In particular, where sensors 74, 75 and 76 include a conductivity sensor and a potassium-sensitive electrode, a proper amount of a potassium salt and other salts can be added in response to ionic substances entering the dialysate loop. Further, an ammonium ion sensor 53 can be present since any ammonium ions reaching the patient or the hemodialysis unit 15 can be dangerous. Dialysate flow to the patient and/or hemodialysis unit 15 can be stopped if the presence of ammonium ions is detected.

For example, at the onset of the dialysis session, the serum potassium level can hypothetically be 7 mM, which can be approximated by the dialysate return composition sensor 25. If the 90% of the potassium ions are removed by the electrodialysis unit 122, then the remaining potassium ion concentration would then be 0.7 mM, which would be detected by the set of sensors 74, 75 and 76 (not all sensors are required in all embodiments). If the desired potassium ion concentration in the dialysate is 4 mM, then the infusate set 35 can add an amount of potassium salt to bring the concentration from 0.7 to 4 mM. Using such a feedback technique, the needed amount of infusate solutions and sorbent materials are reduced.

Figure 8:
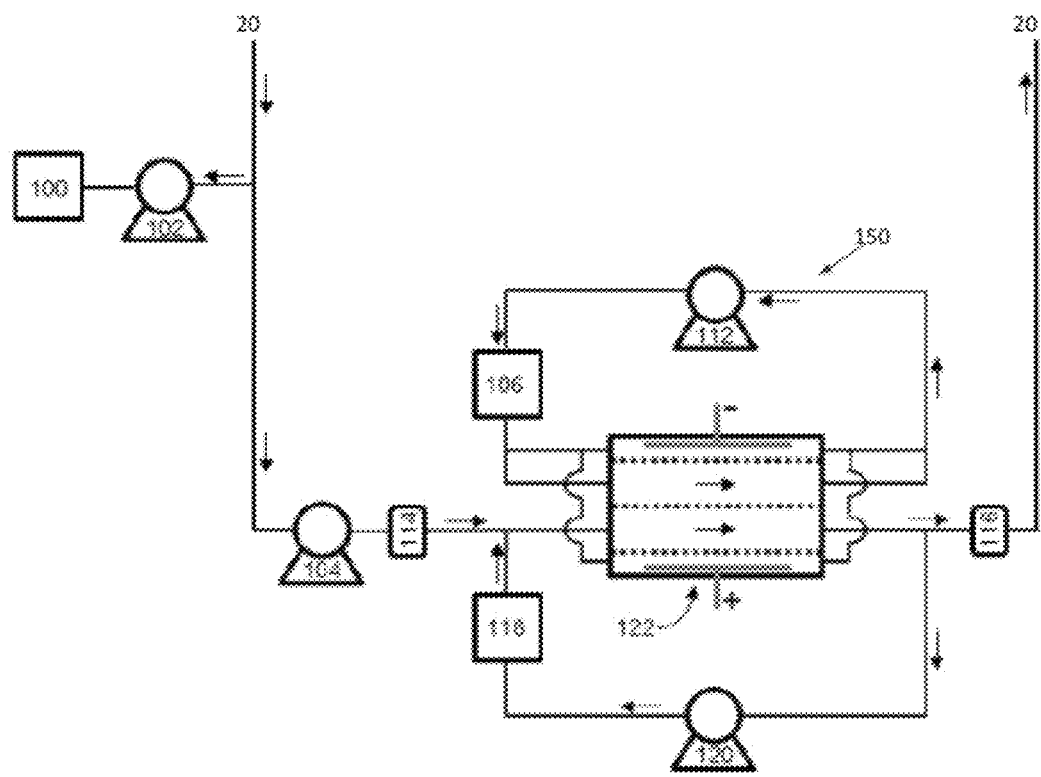
FIG. 8 shows a schematic for an embodiment of a purification module in accordance with some embodiments.

FIG. 8 shows another embodiment of the invention. In this embodiment, the electrode solution and the concentrate solution are mixed through passage of reservoir 106 and the resulting solution circulated using the pump 112. As such, one pump and one reservoir are removed from the purification module 30 when compared to the embodiment as shown in FIG. 7.

Figure 9:
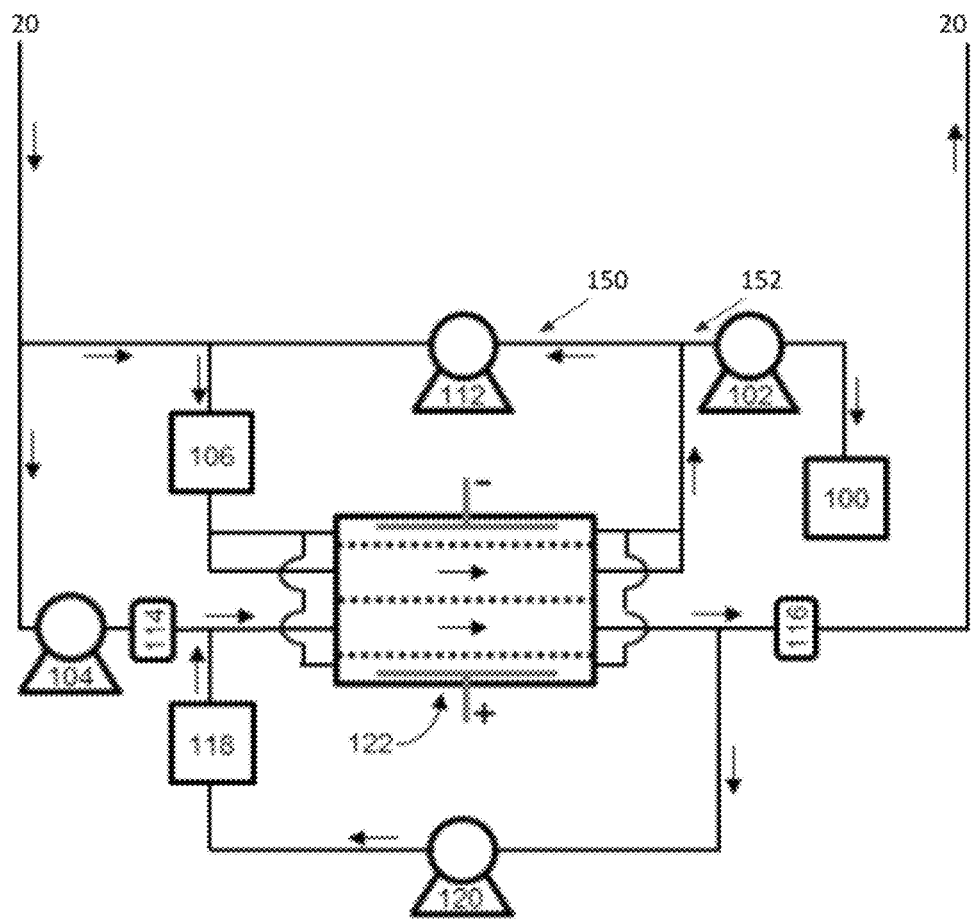
FIG. 9 shows a schematic for an embodiment of a purification module in accordance with some embodiments.

A further embodiment is shown in FIG. 9. The concentrate solution and electrode solution are circulated via pump 112 and stored in a combined reservoir 106. In the embodiment shown in FIG. 9, a means is provided for diluting the concentration of the solution stored in reservoir 106. The control pump 102 and reservoir and drain 100 are attached to the concentrate solution and electrode solution recirculation loop 150 via a conduit 152. As such, operation of the control pump 102 draws fluid from the dialysate loop 20 into reservoir 106. As such, a small amount of fluid is obtained from the dialysate loop 20 and used to reduce the concentration of ions in the concentrate solution stored in reservoir 106. An equal volume of more concentrated concentrate solution is removed to reservoir/drain 100 by the control pump 102. As such, the build-up of ammonia and other waste species in the concentrate solution can be limited.

In the embodiment shown in FIG. 9, operation of the control pump 102 can affect ultrafiltration by drawing fluid from the blood circuit 10 into the dialysate circuit 20. However, operation of the control pump 102 does not necessarily result in an equal migration of fluid into the dialysate circuit 20 from the blood circuit 10, since an amount of water can be added to the control circuit 20 in conjunction with operation of the control pump 102 as discussed above.

Figure 10:
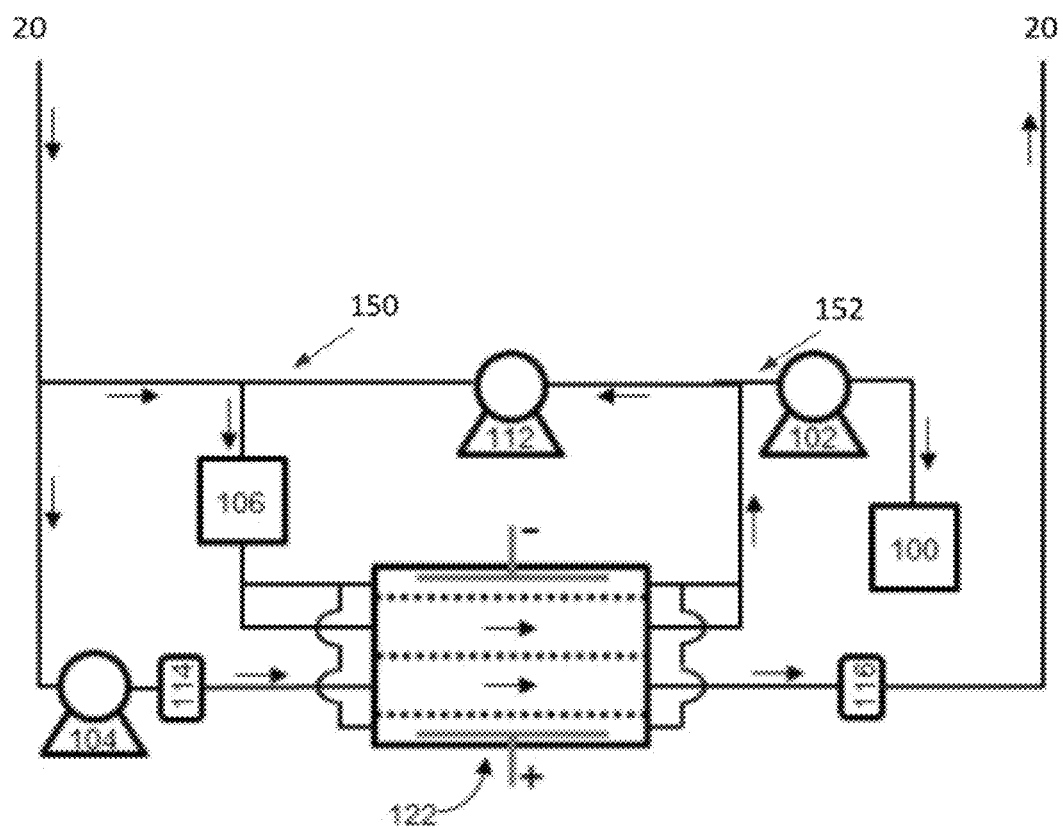
FIG. 10 shows a schematic for an embodiment of a purification module in accordance with some embodiments.

A further embodiment is shown in FIG. 10. The embodiment shown in FIG. 10 is largely parallel to the embodiment shown in FIG. 9. However, the diluate circulation pump 120 and the diluate reservoir 118 are eliminated to save space in the purification unit 30.

Figure 11:
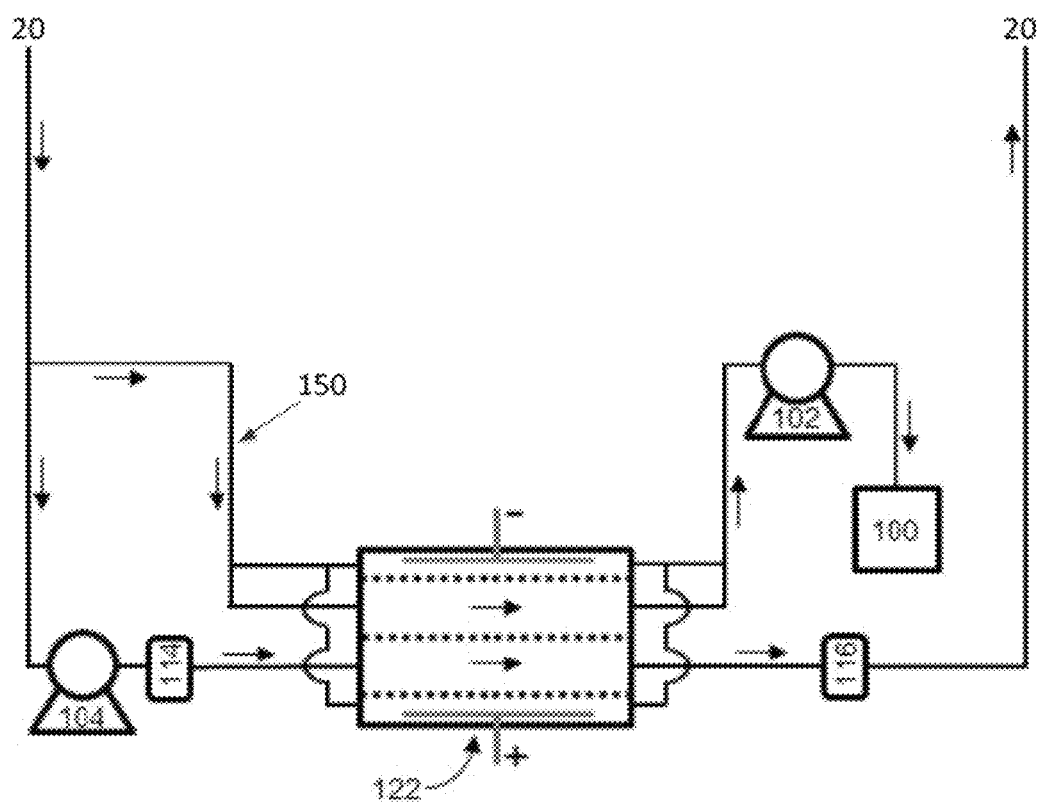
FIG. 11 shows a schematic for an embodiment of a purification module in accordance with some embodiments.

A still further embodiment is shown in FIG. 11 that simplifies operation of the purification unit 30. In this embodiment, the concentrate circulation pump 112 and the concentrate reservoir 106 are in the purification module unit 30. In FIG. 11, the concentrate solution is not re-circulated. Rather, a portion of the dialysate entering the purification unit 30 is diverted through the concentrate and/or electrode chambers of the electrodialysis unit 122 through operation of the control pump 102 to draw dialysate into conduit 150. This amount of diverted dialysate is then discarded into reservoir/drain 100.

Figure 12:
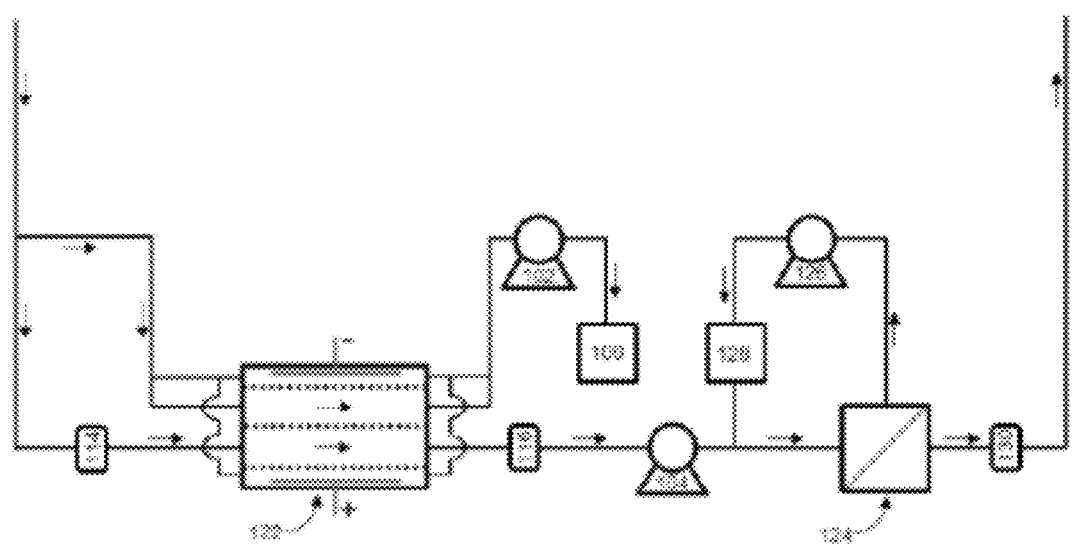
FIG. 12 shows a schematic for an embodiment of a purification module in accordance with some embodiments.

An additional embodiment is shown in FIG. 12. The embodiment shown in FIG. 12 lacks a concentrate circulation pump 112 or concentrate reservoir 106. A reverse osmosis unit 124, a high-pressure pump 104 and a high-flow pump 126 along with a reservoir 128 are added in-line with the electrodialysis unit 122. The reverse osmosis unit 124 allows for a more complete removal of the solutes from the dialysate. Reverse osmosis uses a filter-based technique to remove both ionic and non-ionic species. In reverse osmosis, a hypotonic solution is separated from a hyper tonic solution via a membrane that is permeable to a solvent (e.g. water) but impermeable to solute. A high pressure is applied to the hypertonic solution to counteract osmotic pressure and drive solvent from the hypertonic solution to the hypotonic solution. Here, the hypertonic solution is the diluate solution exiting the electrodialysis unit 122 that can still contain some waste species. Pressure from high-pressure pump 104 drives solvent from the diluate solution into a pure water compartment within the reverse osmosis unit 124. The diluate circuit can be re-circulated by pump 126 to increase the efficiency of reverse osmosis.

Figure 13:
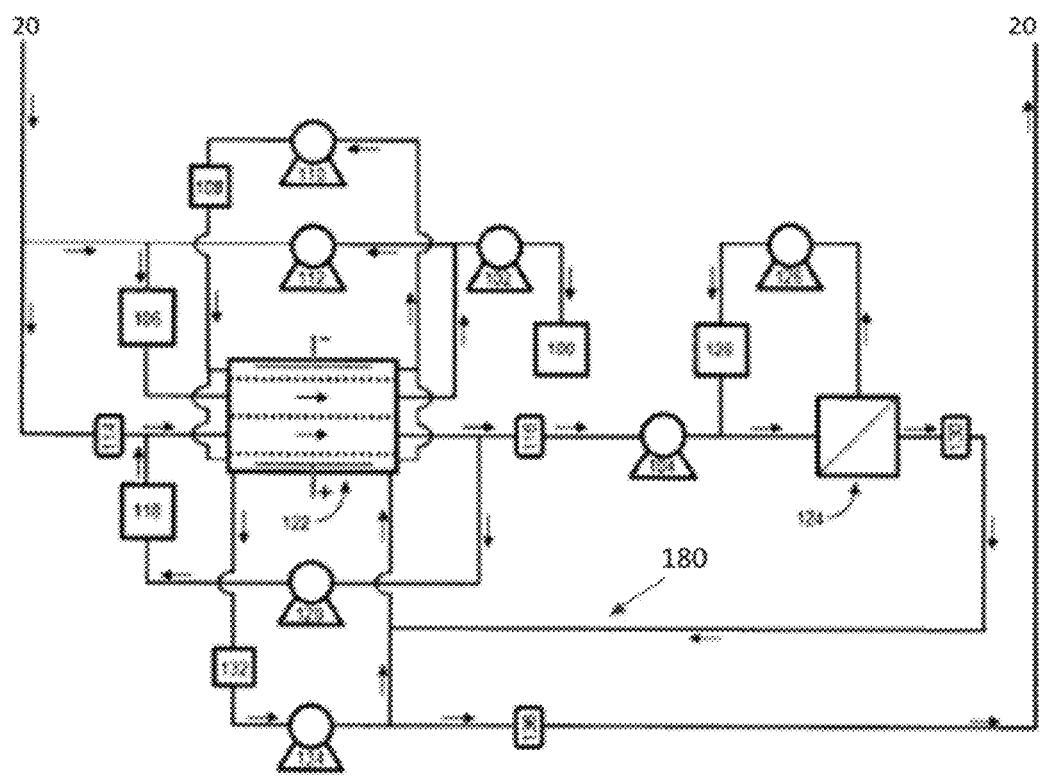
FIG. 13 shows a schematic for an embodiment of a purification module in accordance with some embodiments.

An additional embodiment employing a reverse osmosis unit 124 is shown in FIG. 13. Element numbers in FIG. 13 conserved from FIGS. 7 and 12 refer to like elements. In the embodiment shown in FIG. 13, three separate reservoirs 108, 106 and 118 are used along with pumps 110, 112 and 120 to circulate an electrode rinse solution, a concentrate solution and a diluate solution, respectively. Again, the diluate solution is the solution used for the regeneration of the dialysate. As in FIG. 7, the diluate solution can be re-circulated via the pump 120 to increase the flow rate of the diluate over and beyond the flow rate of the dialysate within the dialysate loop 20, which is circulated via the pump 134 through the dialysate loop 20.

The portion of the diluate exiting the electrodialysis unit 122 not re-circulated by pump 120 is passed through a conditioning unit 116 and a high-pressure pump 104 and a reverse osmosis unit 124. Optionally, the diluate solution can be re-circulated through the reverse osmosis unit 124 using pump 126 and reservoir 128 as shown. After diluate solution passes through the reverse osmosis unit 124, it returns back to the electrodialysis unit 122 through a separate, secondary, diluate feed line 180 as shown. The electrodialysis unit 122 can include a separate set of diluate chambers to accommodate the flow of the secondary diluate through the electrodialysis unit 122. The secondary diluate can also include a secondary diluate reservoir 132 and a secondary diluate pump 134 that both re-circulate part of the secondary diluate as well as provide for circulation through the dialysate loop 20. Also, a final conditioning unit 136 can be included to remove components that were not completely removed by the up-stream components.

For embodiment shown in FIG. 13, the primary conditioning unit 114 can contain activated carbon and/or an ion-exchange resin; however, urease need not be present in primary conditioning unit 114. The secondary conditioning unit 116 can contain an additional ion-exchange resin and/or activated carbon. A tertiary conditioning unit 130 located at the outlet of the reverse osmosis unit 124 can contain urease (typically attached to a resin) to break down urea that has made it through the reverse osmosis unit 124. As described above, the fluid exiting the reverse osmosis unit 124 and tertiary conditioning unit 130 is returned to the electrodialysis unit 122 via the secondary diluate line 180.

That is, FIG. 13 presents an embodiment where the spent dialysate solution from the dialysate circuit 20 passes through the electrodialysis unit 122 without converting urea to a charged species. As such, the electrodialysis unit 122 serves to remove ions from the spent dialysis fluid (e.g. $Na^+$, $K^+$, $Cl^-$, etc.) while urea is not removed. The primary diluate thus formed is then passed to a reverse osmosis unit 124 which can remove charged as well as uncharged species such as urea. As such, the concentration of urea in a diulate is reduced prior to contact with a tertiary conditioning unit 130 containing urease for the generation of ammonium ions. Because the urea concentration is significantly reduced by the reverse osmosis unit 124, potentially up to 80% less urease can be required in tertiary sorbent cartridge 130 compared with other embodiments discussed above. As such, size and overall operating cost can be reduced. The final conditioning unit 136 can contain an ion-exchange resin to remove any remaining dialysate impurities, such as ammonium, phosphate, calcium, potassium, etc. not removed by up-stream components.

System Communication

Figure 14:
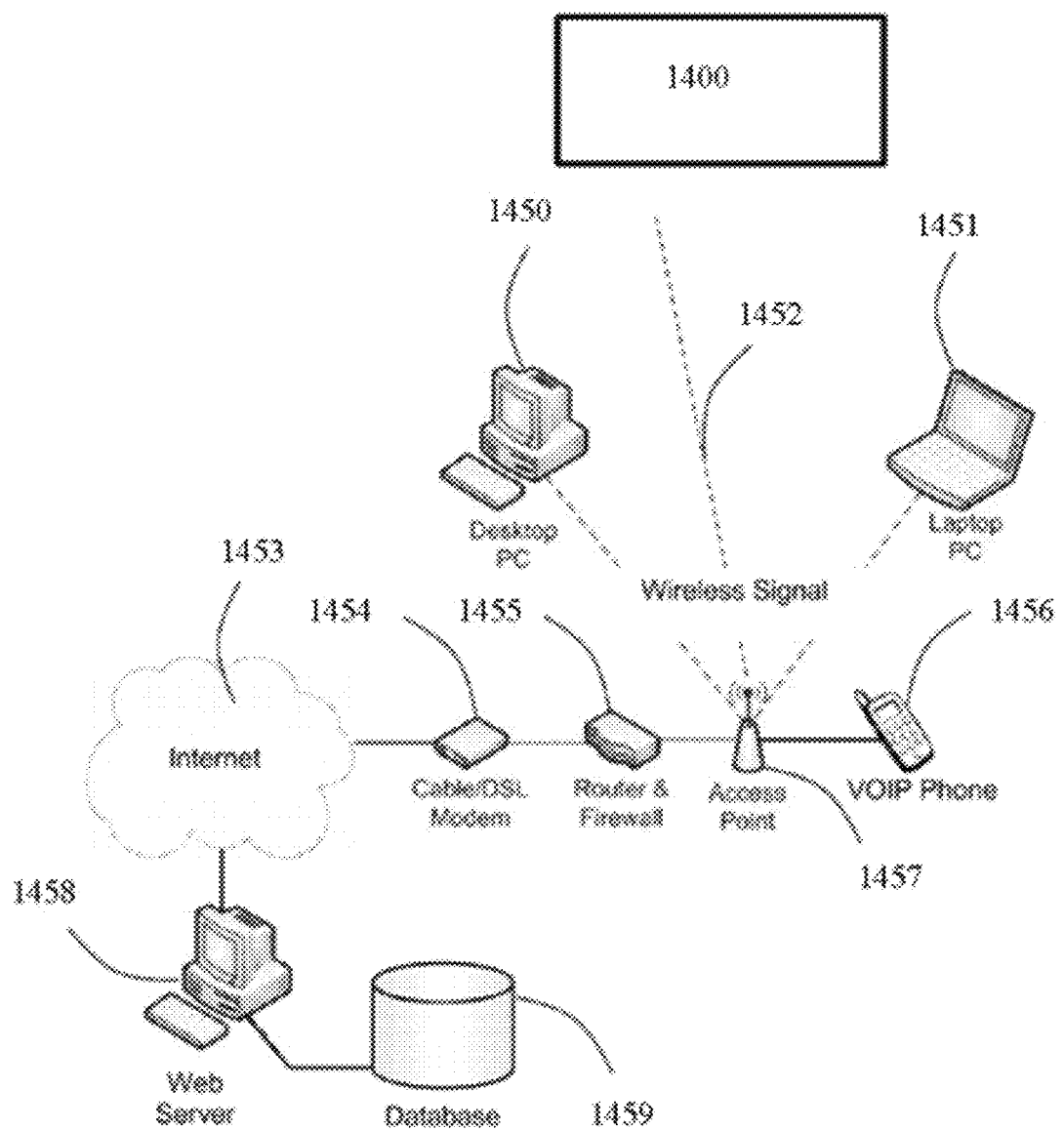
FIG. 14 shows a communication system in accordance with some embodiments.

The electronic controller 1400 of FIG. 14 can monitor pump rates of the system as well as monitor potassium removal and ultrafiltration as described above. For example, the electronic controller 1400 can transmit information based on data from the sensors to a remote device via a computer network, pager network, cellular telecommunication network, and/or satellite communication network, or via an RF link such as Bluetooth, WiFi, or MICS or as described in U.S. Pat. No. 5,683,432 "Adaptive Performance-Optimizing Communication System for Communicating with an Implantable Medical Device" incorporated herein by reference in its entirety, wherein there is no requirement for the electronic controller to be implanted within the patient.

In certain embodiments, the invention includes a telemetry circuit that enables programming by means of a 2-way telemetry link. Uplink telemetry allows device status and diagnostic/event data to be sent a physician or another party for review to track the treatment of a patient. Downlink telemetry allows the programming of device functions of the electronic controller to be performed by parties other than the patient, for example, specific parameters for controlling potassium ion concentration in the dialysate, and the optimization of the therapy for a specific patient. Known telemetry systems suitable for use in the practice of the present invention are contemplated by the invention. Communication with the electronic controller is typically done via a bi-directional radio-frequency telemetry link, such as the CareLink™ system (Medtronic, Inc., Minneapolis, Minn.).

As shown in FIG. 14, in some embodiments, data from the external controller 100 and/or programming of the external controller can be accomplished through a number of different external devices. The external controller can be in communication with an access point 1457, such as a WiFi access point. The patient can use different types of devices, running applications for sending and receiving data from the external controller 1400, such as a desktop 1450 or laptop PC 1451 or a cellular phone or smart phone device 1456. In some embodiments, data can be transmitted over the internet 1453 via a local router 1455 and modem 1454 for placement on a secure web server 1458 and associated database 1459. The web server 1458 can be accessed by the patient and/or a physician or clinician to update programming of the electronic controller 1400 or to monitor the progress of treatment.

Various telemetry systems for providing the necessary communications channels between an electronic controller and a medical device have been developed and are well known in the art, for example, Telemetry systems suitable for the present invention include U.S. Pat. No. 5,127,404, entitled "Telemetry Format for Implanted Medical Device"; U.S. Pat. No. 4,374,382, entitled "Marker Channel Telemetry System for a Medical Device"; and U.S. Pat. No. 4,556,063 entitled "Telemetry System for a Medical Device," which are all incorporated herein by reference.

Operation of System in Electrodialysis Mode and In-Center Mode

Figure 15:
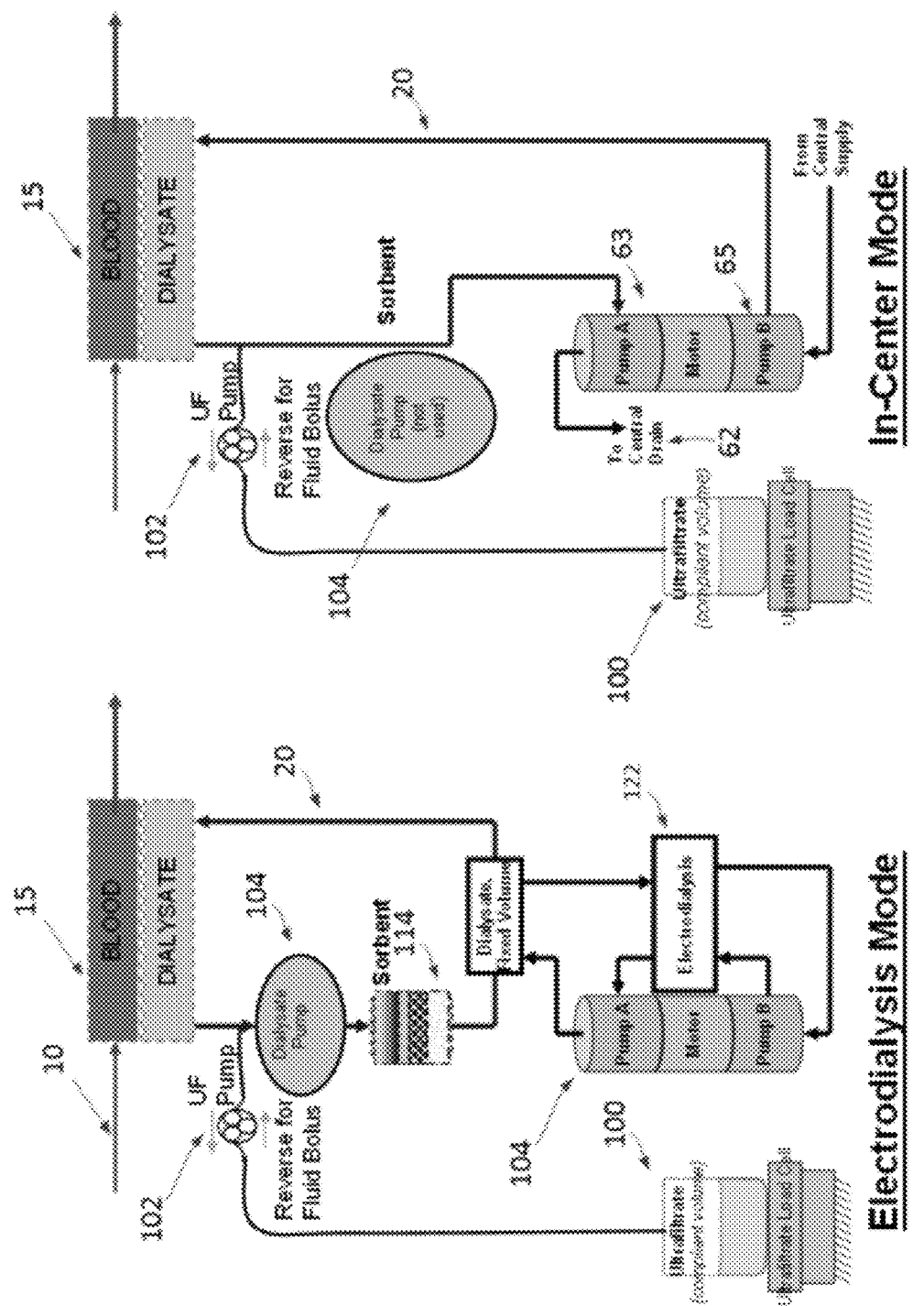
FIG. 15 shows a flow diagram for use of a dual purpose, single-drive reciprocating metering pump in the described systems.

FIG. 15 shows the operation of the device in both modes with electrodialysis regeneration of a fixed volume of dialysate and "in-center" mode with a supply of fresh water. In both modes, dialysate is transported through the dialysis circuit 20 and blood is conveyed through the blood circuit 10, wherein dialysis occurs in the dialyzer 15. Both modes also can make use of a control pump 102 to affect ultrafiltration and bulk removal of fluid from a patient. The two modes differ in that a pump 104 need not be present to drive dialysate flow through dialysis circuit 20 in the "in-center" mode. Rather, dialysate flow is supported by pumps supplying fresh water from the treatment center. Similarly, the electrodialysis unit need not be present nor conditioning unit 114 involved with the regeneration of dialysate.

Cleaning and Disinfection

Figure 16:
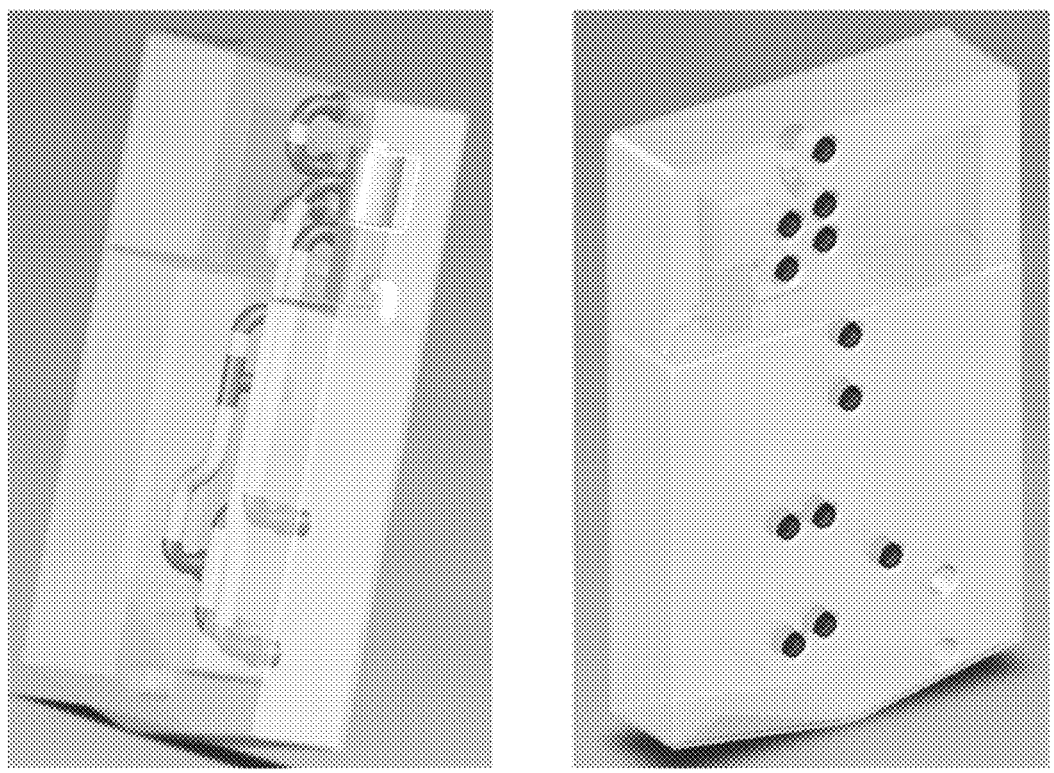
FIG. 16 illustrates the cleaning and disinfection manifold for use in the described systems.

After each use, the system is cleaned and disinfected to prevent the accumulation of biological pathogens, such as bacteria, spores and viruses. This is accomplished by first the removal and disposal of the dialyzer 15, blood circuit 10 and vascular access device 5. Afterwards, a cleaning and disinfection manifold (FIG. 16) is placed in the place of dialyzer 15 and the dialysate loop 20 is flushed with fresh water. If the device was used as a stand-alone unit, then the sorbent cartridges are removed from the primary and secondary conditioning units, 114 and 116 respectively, and replaced with cleaning cartridges containing a cleaning solution, such as citric acid. The built in electrical heater 90 on the dialysate circuit 20 is turned on to bring the temperature of the solution in the dialysate loop to 85 degrees Celsius while the cleaning solution circulates in the dialysate circuit 20 for at least one hour. The system remains idle until the next usage.

Control of Ultrafiltration, Fluid Removal, Fluid Replacement, and Fluid Monitoring As described above, the controlled compliance dialysis circuit can be used to accurately control the bulk movement of fluid across the dialysis membrane in hemodialysis unit 15. The blood circuit 10 functions as an extracorporeal extension of the patient's body. As such, the net movement of fluid from the dialysate circuit 20 to the blood circuit 10 effectively adds fluid to the blood compartment of the patient. Likewise, the net movement of fluid form the blood circuit 10 to the dialysate circuit 20, or ultrafiltration, effectively removes fluid from the blood compartment of the patient.

The blood and circulation of a patient is in balance with the interstitial fluids of the patients or body compartment fluids of the patient. That is, as blood volume or fluid is reduces, the removed blood volume or fluid will be replaced by fluid moving into the blood compartment from the body compartment. However, this process of equilibration between the blood compartment and the body compartment takes time and is not instantaneous. In addition to difficulties in removing impurity components such as urea or maintaining electrolyte balance, patients with KD can similarly have problems removing fluid from the body. As such, dialysis treatment can include the removal of fluid from the blood compartment via the blood circuit 10, which has the effect of drawing fluid out of the body compartment or interstitial areas. However, a removal of fluid from the blood compartment that is too rapid can result in hypovolumia or other adverse effects. As such, in some embodiments, the blood compartment and/or the fluid compartment can be monitored during treatment and adjustments made in the amount of fluid being removed or in the addition of replacement fluid to the patient.

As described above, ultrafiltration or fluid removal from the blood compartment can be accomplished through operation of the control pump 102 in an efflux to remove fluid from the dialysate circuit 20. During operation of the control pump 102 in an efflux direction, the flow rate of fluid exiting the hemodialysis unit 15 is faster than the flow rate of fluid entering the hemodialysis unit 15, wherein the additional fluid exiting the hemodialysis unit 15 originates from the blood present in the blood circuit 10. During treatment, adding a replacement fluid to the blood circuit 10 can become necessary. To accomplish the addition of a replacement fluid, water intake pump 165 can be operated to add fluid into the dialysis circuit 20 to cause a net addition of fluid to the blood circuit 10 across the hemodialysis unit 15 when the unit is operated in electrodialysis mode as described above. During operation in in-center mode, the flow balance between pumps 65 and 63 as described above with proper operation of the flow balance unit 40, as described above. The replacement fluid added to the blood circuit 10 has the composition of the dialysate fluid constituted or re-constituted by the infusion set 35, as described above.

If the rate of fluid removal from the blood compartment is too large, the rate of fluid flow from the tissue compartment may not be sufficient to keep up with the rate of fluid loss from the blood compartment, which can result in hypovolemia or low blood volume. A more moderate differential of fluid loss between compartments may be desired from a patient health perspective. In some embodiments, agents that increase the osmolality of dialysate and thus blood can be used to increase the rate at which fluid is transferred from the tissue or body compartment to the blood compartment of the patient. That is, by increasing the concentration of osmolality enhancer in the dialysate, fluid can be removed from blood at a higher rate as a result of an increase in fluid migration from the body compartment. However, the osmolality enhancer can also pass through the dialysis membrane and increase in concentration in the blood and the blood returned to the patient may have a higher osmolality than the blood removed from the patient. Blood having a higher osmolality will tend to result in more rapid fluid removal from the tissue into the blood. The concentration of the osmolality enhancer used in the dialysate can be changed over the course of a dialysis session; e.g., higher concentration at the beginning and lower concentration at the end. Examples of osmolality enhancers that can be employed include sodium and glucose. Other osmolality enhancers can be used. In lieu of adjusting the osmolality of the dialysate fluid, it may be desirable to monitor fluid loss from the tissue compartment, the blood compartment, or both to determine whether the relative losses or volumes are within a safe range. In some embodiments, suitable ratios of tissue fluid volume to blood fluid volume can be determined on a patient-by-patient basis or can be set initially according to population statistics. As a general rule, decreases in blood volume at a rate of 8 to 10% per hour can cause imminent hypovolemia.

Any suitable sensor can be employed to monitor fluid in the blood compartment or the tissue/body compartment. Examples of sensors and systems that may be employed with regard to blood fluid volumes and tissue fluid volumes are discussed in U.S. Provisional Patent Application No. 61/480,528, filed on Apr. 29, 2011, and U.S. patent application Ser. No. 13/424,454, filed Mar. 20, 2012, both entitled FLUID VOLUME MONITORING FOR PATIENTS WITH RENAL DISEASE; and U.S. Provisional Patent Application No. 61/480,530, filed on Apr. 29, 2011, and U.S. patent application Ser. No. 13/424,467 filed Mar. 20, 2012, both entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well-studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

Control of the rate of fluid removal (i.e. ultrafiltration) and fluid replacement can be adjusted based upon a ratio of fluid measured between the tissue compartment and the blood compartment. In the embodiment shown in FIG. 17, a dialysis session including blood fluid removal is initiated in step 500 and indicators of tissue fluid volume 510 and blood fluid volume 520 are monitored. The blood fluid removal session can be continuously monitored. The ratio of blood fluid volume to tissue fluid volume is compared, and a determination as to whether the ratio is outside of a predetermined acceptable range is made in step 520. If the ratio is determined to not be outside a predetermined range, the blood fluid removal session continues with the previously set parameters with regard to fluid removal from the blood. If the ratio is determined to be outside the predetermined range, then rate of fluid removal from the blood is altered in step 540.

For example, if the ratio of the tissue fluid volume to blood fluid volume is above the predetermined range, the rate of fluid removal can be decreased. That is, if too much fluid is taken out of the blood or if fluid is removed at a rate faster than the rate at which fluid from the tissue compartment may fill the blood volume, the ratio of tissue fluid volume to blood fluid volume will increase. If the ratio increases to an extent beyond the predetermined range, the rate of fluid removal from the blood can be decreased to allow more time for fluid from the tissue compartment to flow into the blood and bring the fluids in the blood compartment and tissue compartment into appropriate balance and avoid an undesired fluid imbalance that can have negative consequences on patient health.

In contrast, if the ratio of tissue fluid volume to blood fluid volume is below the predetermined range, the rate of fluid removal from the blood can be increased. For example, for purposes of efficiency, it may be desirable to keep a slight, but safe fluid imbalance between the blood compartment and the tissue compartment to drive out excess fluid at a safe and efficient rate. While a low ratio of tissue fluid volume to blood fluid volume may not result in a health risk to the patient (provided that a sufficient volume of fluid is eventually removed), the time in which a patient undergoes a blood fluid removal process may be unnecessarily extended. Thus, by monitoring tissue fluid volume and blood fluid volume during a blood fluid removal session, the rate of fluid removal can be finely controlled based on the monitored indicators to enhance patient safety and to enhance efficiency of the blood fluid removal process.

A ratio of tissue fluid volume to blood fluid volume being too low can also be indicative of too much replacement fluid being added to the blood circuit 10. Accordingly, the rate at which replacement fluid is added can be decreased (which effectively increases the rate of fluid removal for purposes of the present disclosure).

An appropriate range of tissue fluid volume to blood fluid volume can be determined in any suitable manner. For example, the ratio at the patient's dry weight can be defined as the reference. In general, blood is about 7% of body weight and total tissue fluid is about 60% of the body weight (including blood, extracellular and intracellular fluid). Thus, the typical tissue to blood fluid volume ratio of a healthy individual is 53/7, or about 7.6 (e.g., in the range of 6 to 9). This can be used as a starting point for an appropriate ratio of tissue fluid volume to blood fluid volume to be achieved. Alternatively or in addition, the reference ratio can be obtained through a learning process over the course of therapy and can be patient-dependent. The pattern of change of the tissue to blood volume ratio (or indicators thereof) can be optimized through the learning process. As an optimized pattern is learned, it can be used to guide personalized therapy to achieve better outcomes on a patient-by-patient basis.

In some embodiments, a learning algorithm or evolving algorithm that looks at the rate of change of both blood and tissue is used. The difference in rate of change can be used to determine the time constant of the fluid exchange between the tissue and blood compartments. This information can then be used to establish a target on hematocrit (or other indicator of blood fluid volume) for a final state, while taking into consideration the slower transfer between tissue and blood compartments. This could be used to dynamically adjust the fluid removal rate. Limits can be established by patient or clinician input. The initial calibration can be learned or can utilize other information such as weight or other external lab input.

Figure 17:
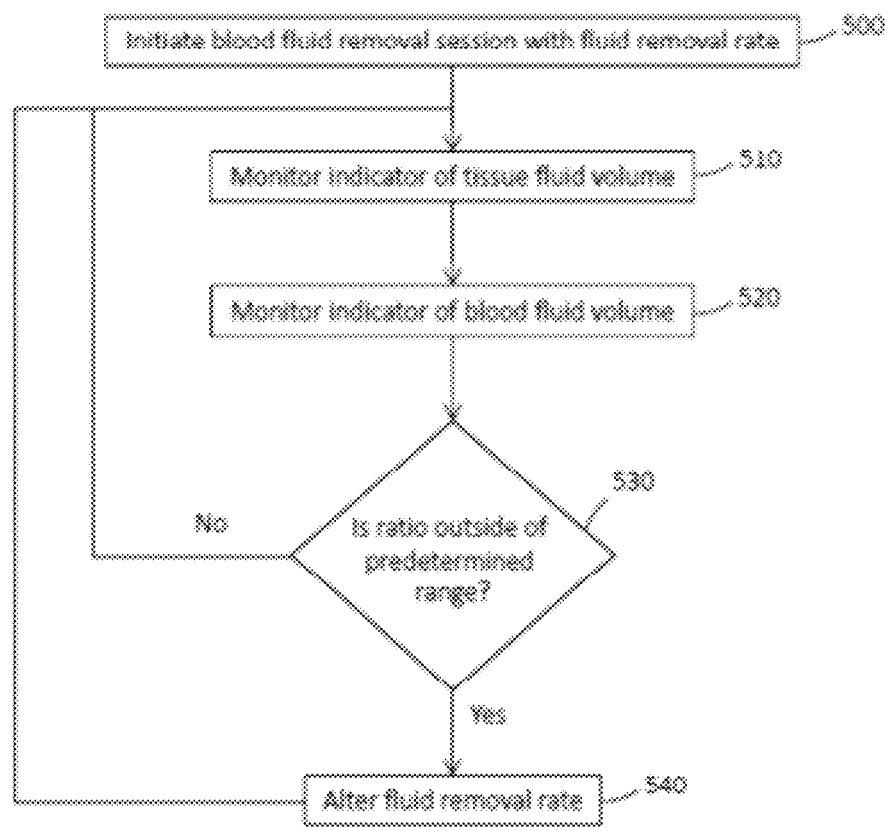
FIGS. 17-21 are flow diagrams depicting overviews of methods in accordance with certain embodiments described herein.
Figure 18:
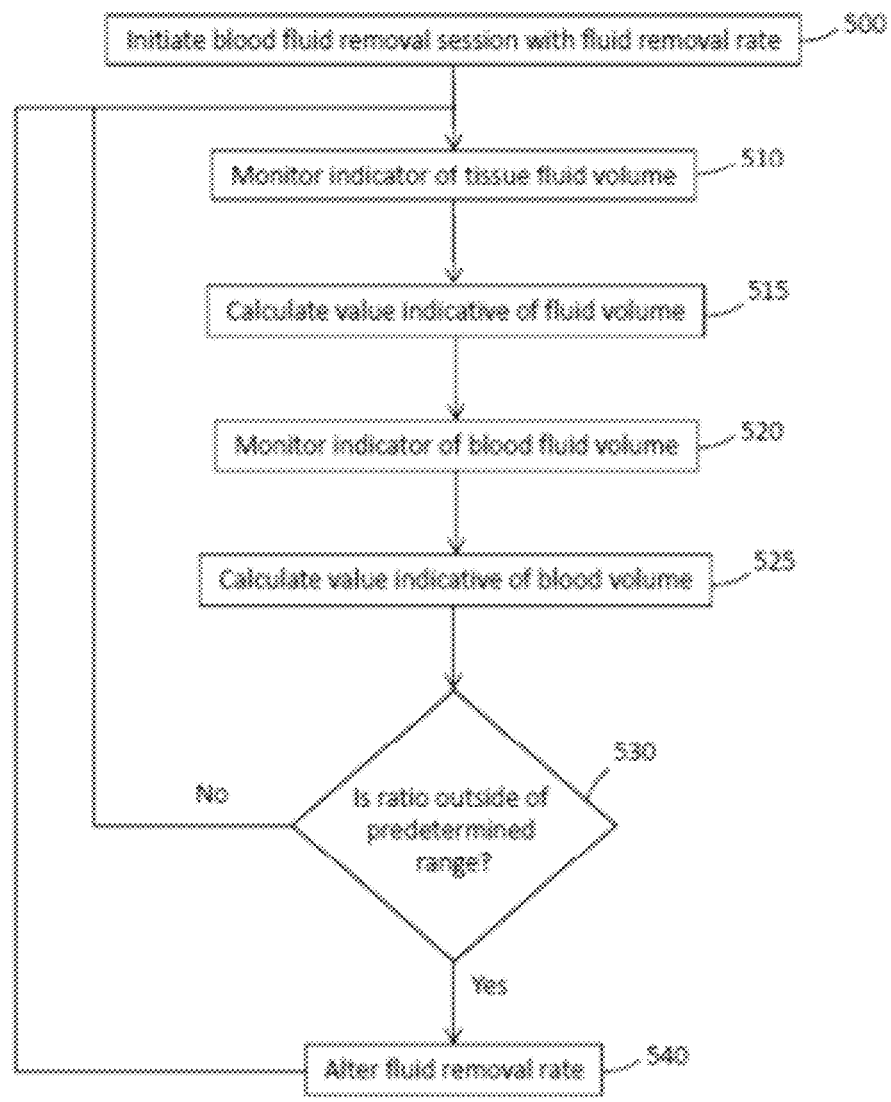

Referring now to FIG. 18, a method shaving details to that depicted in FIG. 17 is shown. In FIG. 18, the method includes calculating a value indicative of tissue fluid volume 515 based on the monitored indicator 510 and calculating a value indicative of blood volume 525 based on the monitored indicator 520. The ratio of tissue fluid volume to blood fluid volume can be determined based on these calculated values 530 rather than on the values obtained with regard to the monitored indicators themselves as depicted in FIG. 17. In either case, the outcome is essentially the same, provided that differences in the way indicators of tissue and blood fluid volume can predict volume are accounted for.

For example, if tissue fluid volume is determined by impedance, an increase in tissue fluid volume would result in an increase in impedance. However, if hematocrit levels were used to determine blood fluid volume, an increase in blood fluid volume would result in a decrease in hematocrit. Accordingly, if the determination regarding the ratios in the embodiment in FIG. 17 took into account that a increase in hematocrit indicates an decrease in blood fluid volume, the end result would be essentially the same as would be obtained in the method of FIG. 18. Put another way, if it was understood and accounted for that the ratio of impedance to the hematocrit changes differently from the ratio of tissue fluid volume to blood fluid volume, the methods of FIG. 17 and FIG. 18 will produce similar results with regard to altering the rate at which fluid is removed from the blood.

Figure 19:
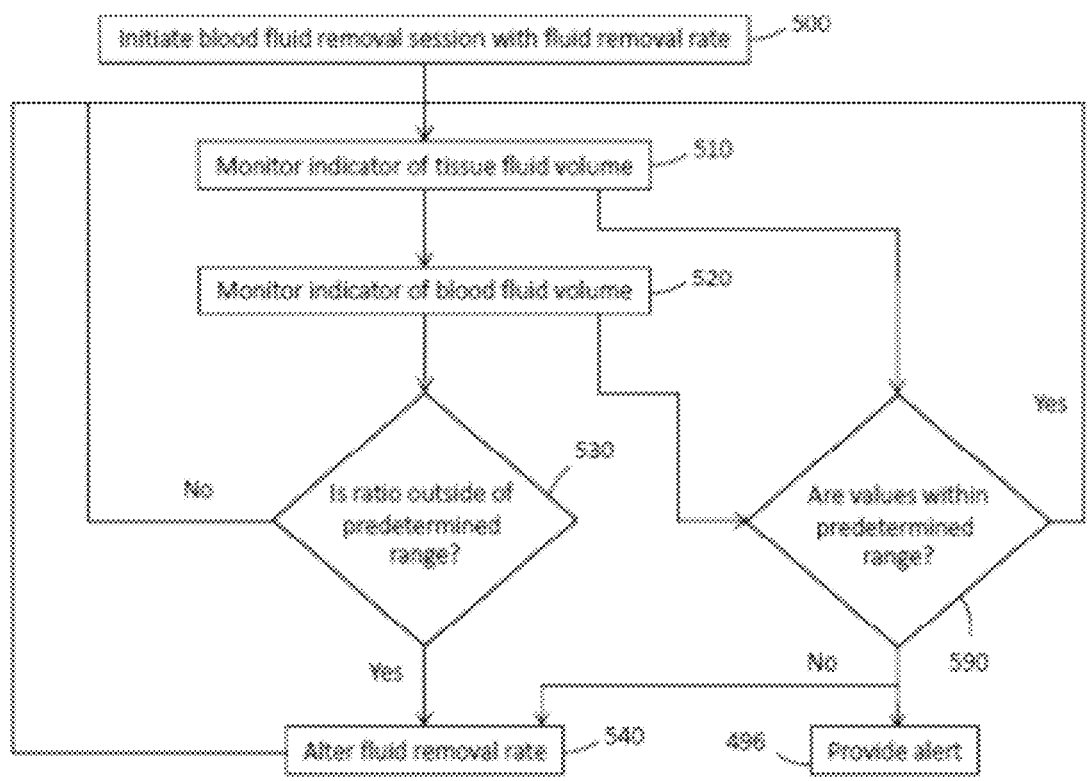

As depicted in FIG. 19, the methods described herein may, in some embodiments, use the monitored indicators of tissue fluid volume 510 or blood fluid volume 520 alone, in addition to the ratio of such values, for purposes of patient safety. As depicted in FIG. 19, it may be determined whether the individually monitored indicator of tissue fluid volume or blood fluid volume is within predetermined acceptable ranges 590. For example, if tissue fluid volume or blood fluid gets unacceptably low (even though the ratio may be within acceptable ranges) or too high, the rate of fluid removal from blood may be altered 540. By way of example, if a value of the indicator of tissue fluid volume is indicative of a near dry weight volume, the rate of fluid removal from blood may be reduced to allow a proper ratio of tissue fluid volume to blood fluid volume to be achieved prior to reaching the dry weight fluid volume. Thus in some embodiments, the threshold for determining whether a value of the monitored indicator of blood of tissue fluid volume is outside of a predetermined range may change based on the ratio of tissue to blood fluid volume. For example, if the ratio of tissue to blood fluid volume is high (indicating a rapid removal of fluid from blood), then the lower threshold for tissue fluid volume (e.g., nearing dry weight) may be higher than if the ratio of tissue to blood fluid volume was low (suggesting less rapid removal of fluid from blood) to avoid overshooting the dry weigh tissue fluid volume.

As also depicted in FIG. 19, an alert such as an audio or visual alarm may be provided 496 to alert the patient or a healthcare provider that a potentially dangerous patient health situation exists with regard to too high or too low fluid volume in the tissue or blood.

Figure 20:
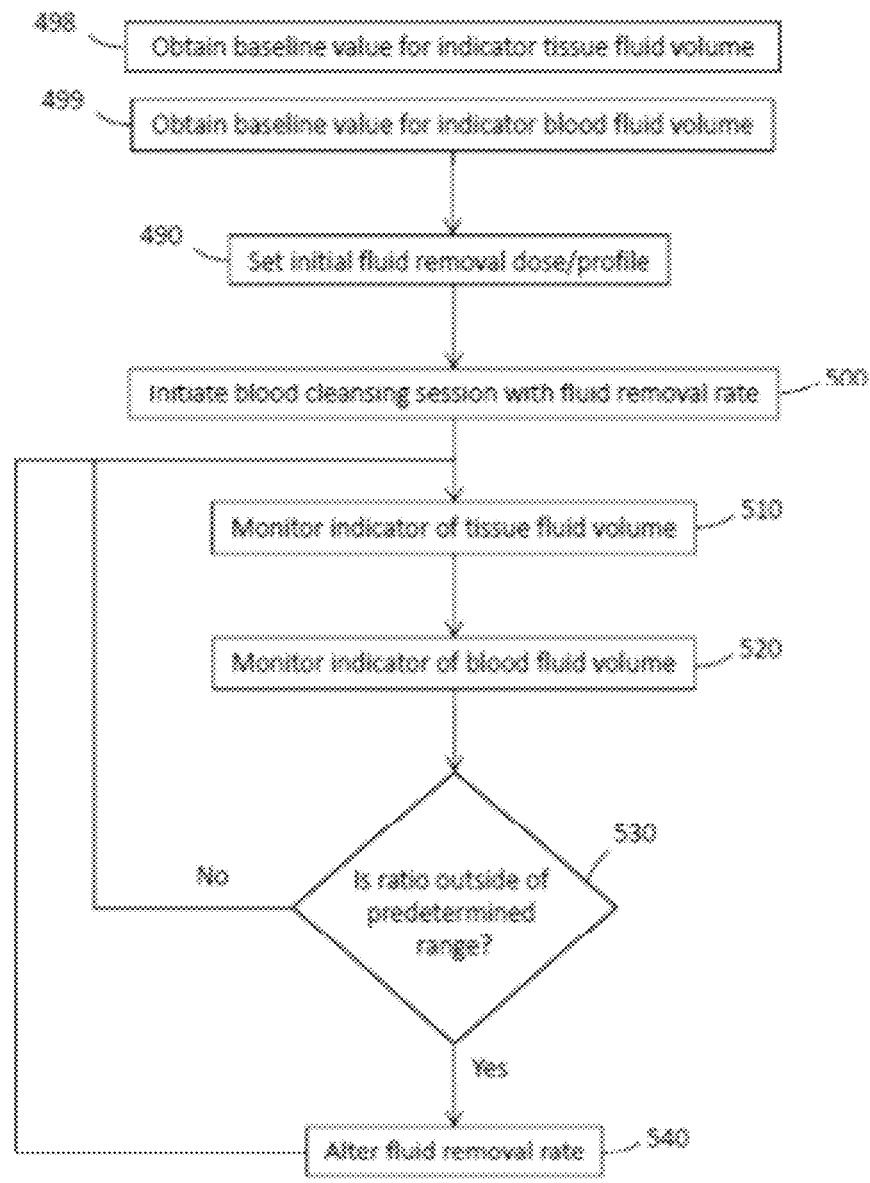

Referring to FIG. 20, a method having similarities to that depicted in FIG. 17 is shown. The method in FIG. 20 includes obtaining a baseline value for an indicator of tissue fluid volume 498 or obtaining a baseline value for an indicator of blood fluid volume 499 prior to initiating a blood fluid removal session 500. One or both of the baseline values may be used to determine the initial dose or prescription for fluid removal for the blood fluid removal session 490. The rate of fluid removal from the blood may be adjusted 540 during the blood fluid removal session based on monitoring 510, 520 that occurs during the session.

Figure 21:
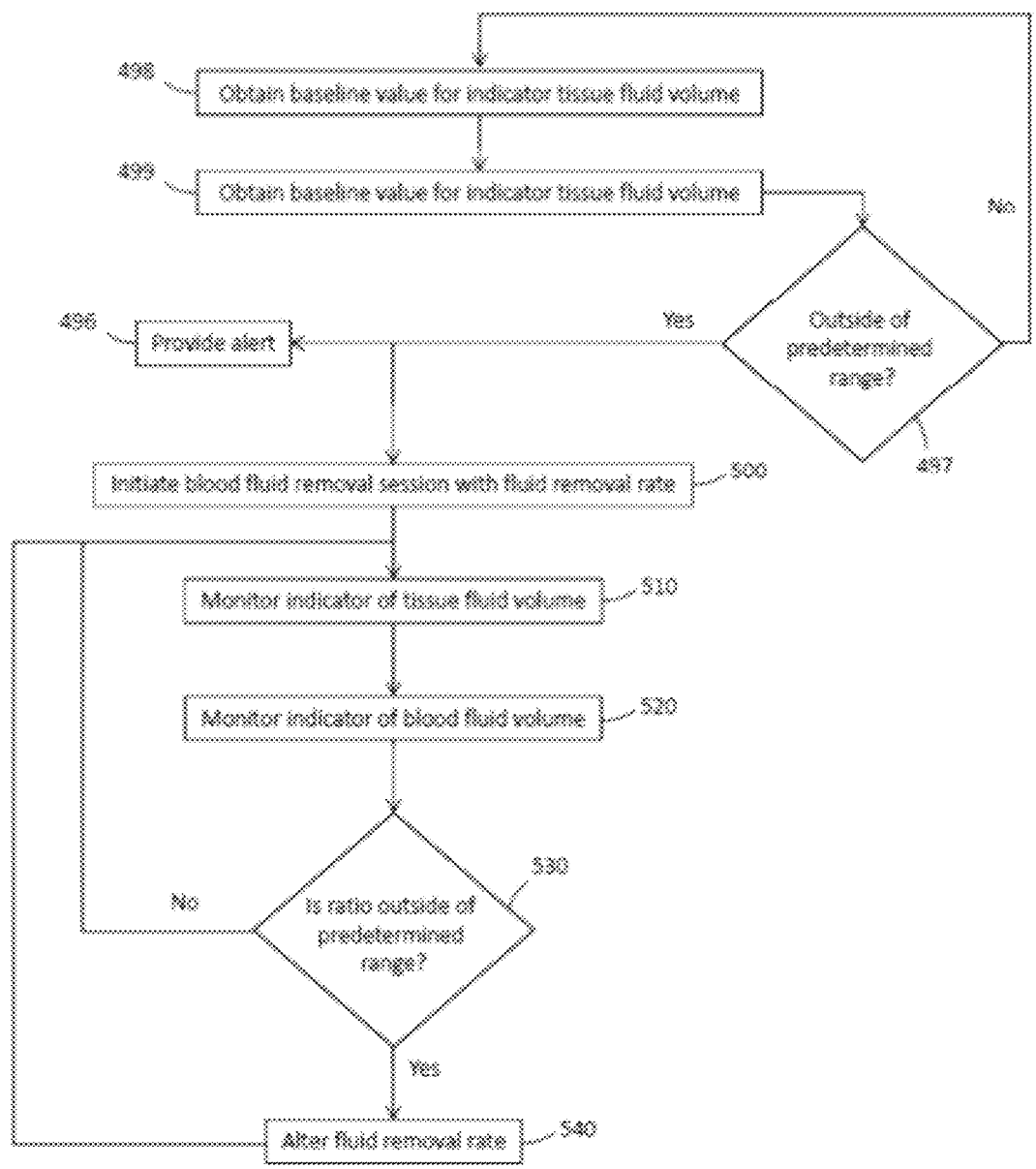

Referring now to FIG. 21, a method having similarities to that depicted in FIG. 17 is shown. The method in FIG. 21, like the method depicted in FIG. 20, includes obtaining a baseline value for an indicator of tissue fluid volume 498 or obtaining a baseline value for an indicator of blood fluid volume 499 prior to initiating a blood fluid removal session 500. If the values are determined to be outside of predetermined acceptable ranges 497, a blood fluid removal session may be initiated 500. Such a method may be advantageously employed in situations where the blood fluid removal device and monitoring sensors are implanted or continuously operating or available to operate, as a blood fluid removal session may be automatically initiated. Alternatively or in addition, the method depicted in FIG. 21 may include providing an alert 496 to the patient or healthcare provider indicating that a blood fluid removal session is advised.

Hypotension is the main complication during dialysis (25-60%). With the methods described herein, which may include real-time blood pressure sensors or other blood volume sensors, imminent blood pressure changes or levels may be predicted, e.g. on a feedforward basis. Accordingly, the rate of fluid removal may be adjusted based on data collected during the fluid removal session to avoid a hypotension situation, as opposed to current standard of care where one starts to adjust the fluid removal rates only when one sees the problems. Dry weight and optimized tissue to blood fluid ratios learned, e.g. as described above, from the therapy course of a patient may help this prediction process to be effective and practical. If necessary or desired, replacement fluid, dialysate or removed fluid may be introduce into the blood circuit 10 to avoid, mitigate or correct a hypotensive event.

Figure 22:
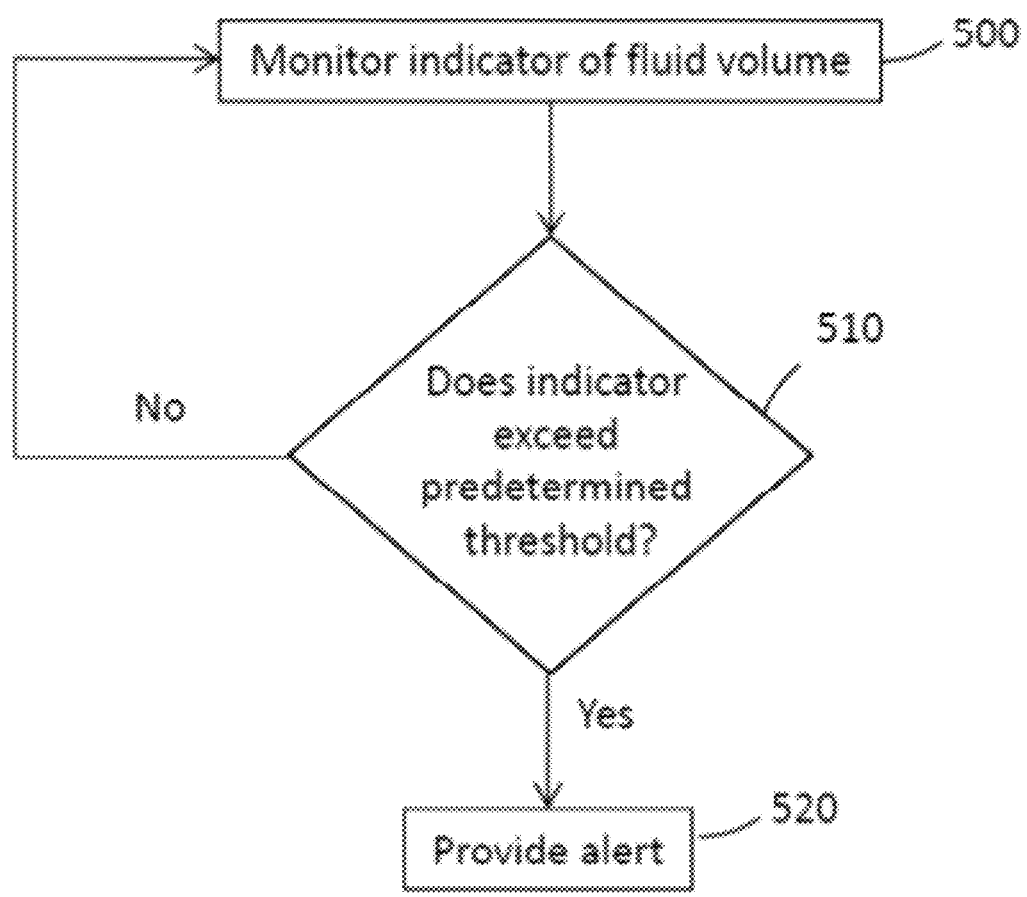
FIGS. 22-24 are flow diagrams depicting overviews of methods in accordance with certain embodiments described herein.
Figure 23:
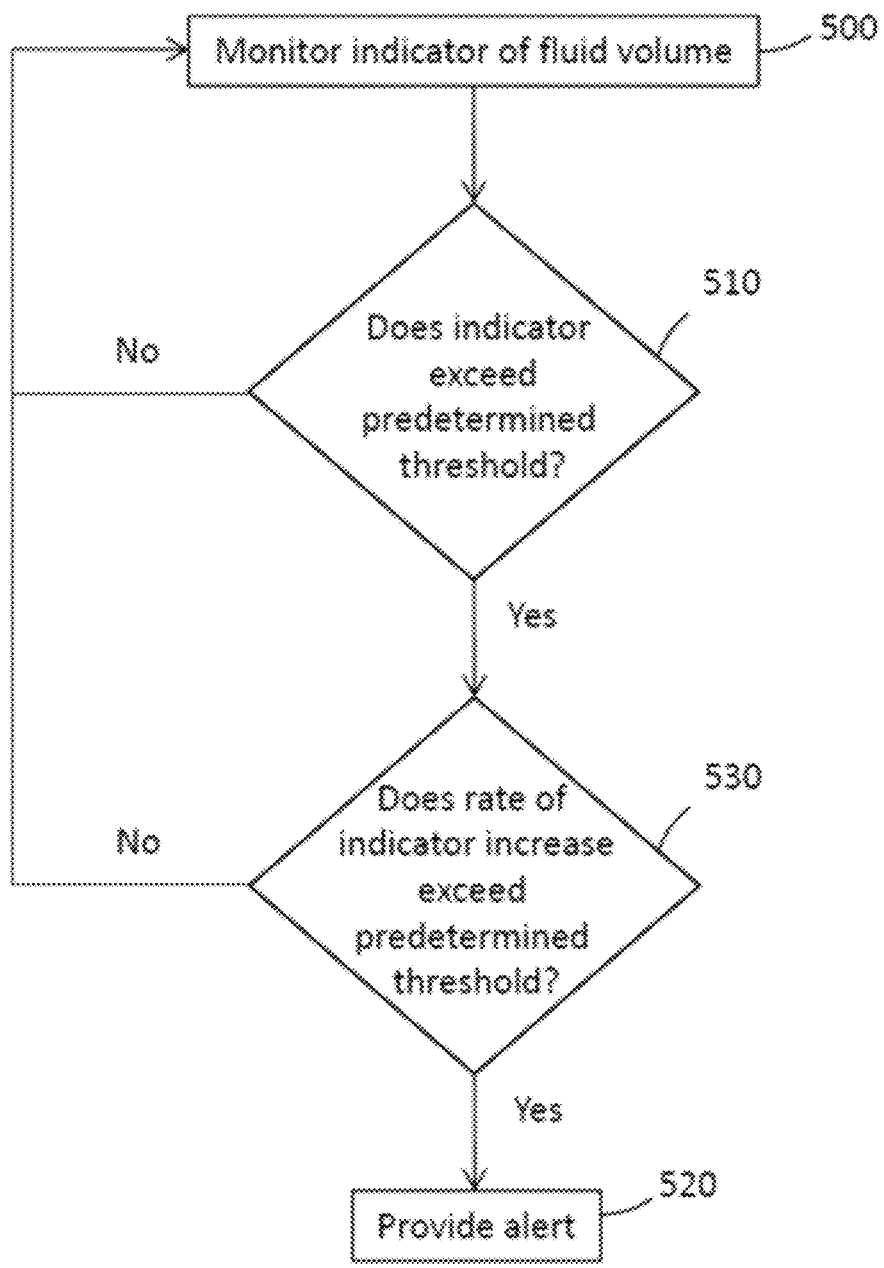
Figure 24:
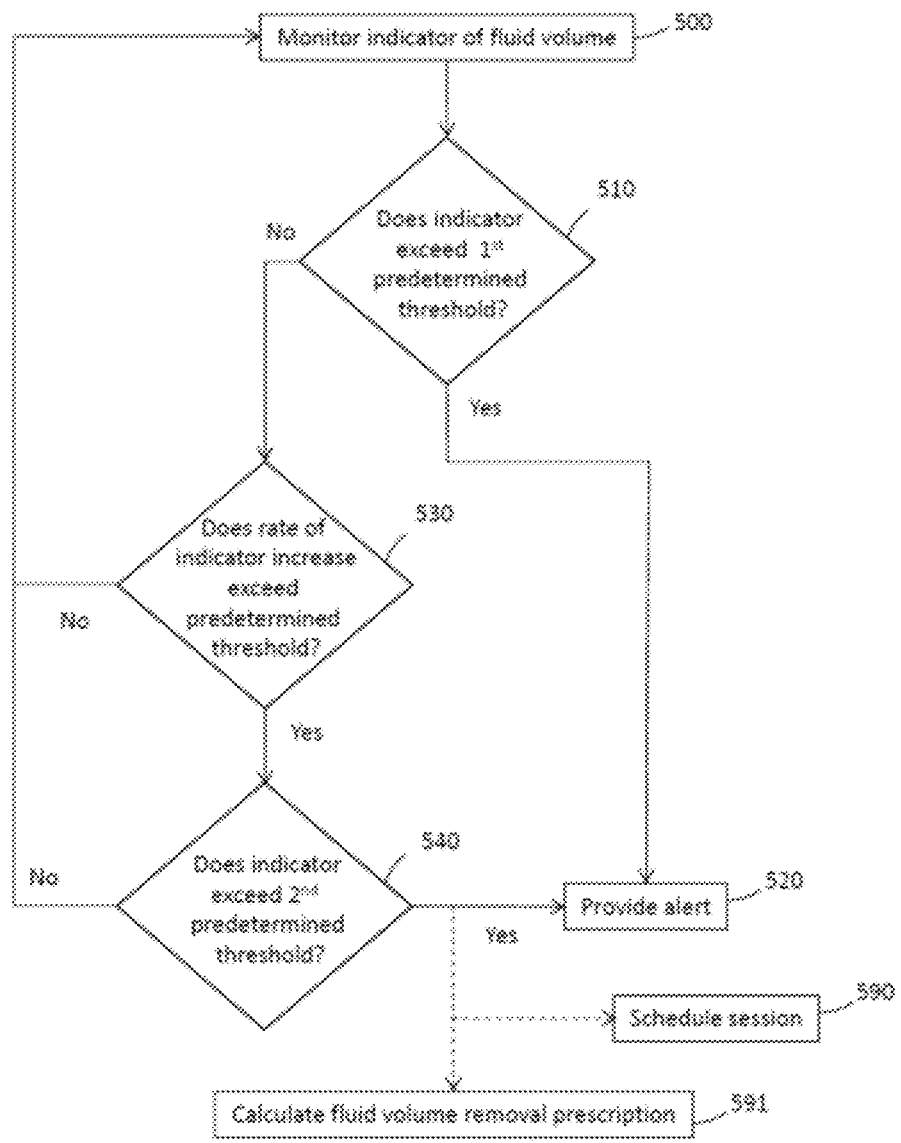

In additional embodiments, a decision to provide an alert or to modify a rate of fluid removal or addition of replacement fluid can be made through the monitoring of only one of the tissue fluid volume or the blood fluid volume. Referring to FIGS. 22-24, overviews of embodiments of methods for monitoring of fluid volume of one of the tissue compartment and the blood compartment are presented. In some embodiments, the methods can be used for purposes of assisting in determining the appropriate timing of a creation of a fistula. For example, an indicator of fluid volume (e.g., as discussed above) can be monitored 500 and a determination may be made as to whether the indicator exceeds a predetermined threshold 510, such as a threshold that is indicative of excess fluid levels that would warrant creation of a fistula. The threshold may be based on empirical data collected over populations of patients based on closely monitored patients in accordance with existing medical practice, may be based on changes from baseline within a given patient, or the like. If the monitored indicator exceeds a threshold indicative of increased fluid, an alert may be provided 520, such as an alert provided by an indicator circuit of a sensor as described above. Data regarding the monitored indicator of fluid volume can be transmitted to a health to a healthcare provider, as described above.

In some embodiments, the methods depicted in FIGS. 22-24 can be used for determining whether a heart failure patient is close to being decompensated. Data regarding fluid levels before or during the patient's prior decompensation events may be marked or evaluated. By way of example, a physician or health care provide may interrogate a fluid monitoring device (e.g. a blood compartment monitor or a tissue compartment monitor) to better understand events that preceded a patient presenting with heart failure decompensation. Thresholds for alerts may be adjusted based on monitored fluid levels, rates, etc. that occurred prior to the patient's decompensated heart failure event. In some embodiments, the monitoring device or system including the monitoring device may receive input regarding the patient's decompensation status, and the device or system may be reviewed data stored in memory to determine whether certain patterns appear in relation to decompensation. Thresholds for issuance of alerts may be adjusted automatically by the device or system.

As shown in FIG. 23, a method may include determining whether the rate of fluid increase, based on the monitored indicator, exceeds a predetermined threshold 530. If the rate of increase of fluid volume is high or exceeds a threshold, the alert (etc.) may be provided. In some embodiments, it may be desirable to determine whether the rate exceeds a threshold 530 prior to determining whether the overall value of the indicator exceeds a threshold 510, because if the rate of increase is high, the overall threshold may be lower than if the rate is low. That is, the threshold 510 may be based on the rate 530.

For example and as shown in FIG. 24, a method may include determining whether the monitored indicator exceeds a first high threshold 510, in which case an alert (etc.) is provided 520. If the indicator does not exceed the first high threshold 510, a determination may be made as to whether the rate of increase of fluid, as indicated by the sensed data, exceeds a threshold 530. If the rate of increase exceeds a threshold, a determination may be made as to whether the value of the monitored indicator (as it is indicative of fluid volume) exceeds a lower second threshold 540. In which case, the alert (etc.) may be provided 520. In this way, a lower threshold may be set if the rate of increase is high. The threshold values may be entered into lookup tables based on prior data from other patients or populations or may be "learned" based on sensed data acquired within the patient.

It will be understood that the methods depicted in, and described with regard to FIGS. 22-24, may be useful for patients that are already undergoing blood fluid removal treatments, and may be used for purposes of automatically scheduling fluid removal session (e.g., 590, FIG. 24), e.g., via telemetry circuit as described above. A sensor monitoring the indicator of fluid volume may also calculate a fluid volume prescription based on the sensed data (e.g., 591, FIG. 24) and transmit data regarding the prescription to a fluid volume removal device or other device that will allow a healthcare provider to enter the appropriate fluid volume removal prescription. Alternatively or in addition, data regarding the monitored indicator may be sent to a fluid volume removal device or other device, which may then calculate an appropriate fluid volume removal prescription (e.g., 591, FIG. 24) based on the transmitted data. The fluid volume prescription data calculated by the sensor device or other device may be based on prior data from other patients or populations or may be "learned" based on sensed data acquired within the patient over time.

Adjustment of Dialysate Composition

As described above, the potassium ion concentrate of a dialysate fluid can be adjusted to adjust potassium ion concentration to obtained better control over the rate of potassium ion removal from the patient, as fully described above. However, additional adjustments to electrolytes contained in a dialysate fluid and/or pH or buffer composition of the dialysate. Accordingly, one goal of hemodialysis, ultrafiltration, and the like is to ensure that the patient's blood pH and electrolyte concentrations are within acceptable ranges. Typical ranges of pH and blood electrolyte concentration that are desired during or following a blood fluid removal session are provided in Table 4 below. Target concentrations of various buffers and electrolytes (or salts or hydrates thereof) are presented on Table 4.

TABLE 4

Typical target ranges for pH and electrolytes
(ref. Medical Surgical Nursing, 7$^{th}$ Ed., 2007)

|  | Target Range |
|---|---|
| pH | 7.35-7.45 |
| Phosphate | 2.8-4.5 mg/dL |
| Bicarbonate | 22-26 mEq/L |
| Cl$^-$ | 96-106 mEq/L |
| Mg$^{2+}$ | 1.5-2.5 mEq/L |
| Na$^+$ | 135-145 mEq/L |

TABLE 4-continued

Typical target ranges for pH and electrolytes
(ref. Medical Surgical Nursing, 7th Ed., 2007)

|  | Target Range |
|---|---|
| $K^+$ | 3.5-5.0 mEq/L |
| $Ca^{2+}$ | 4.5-5.5 mEq/L |

Figure 25:
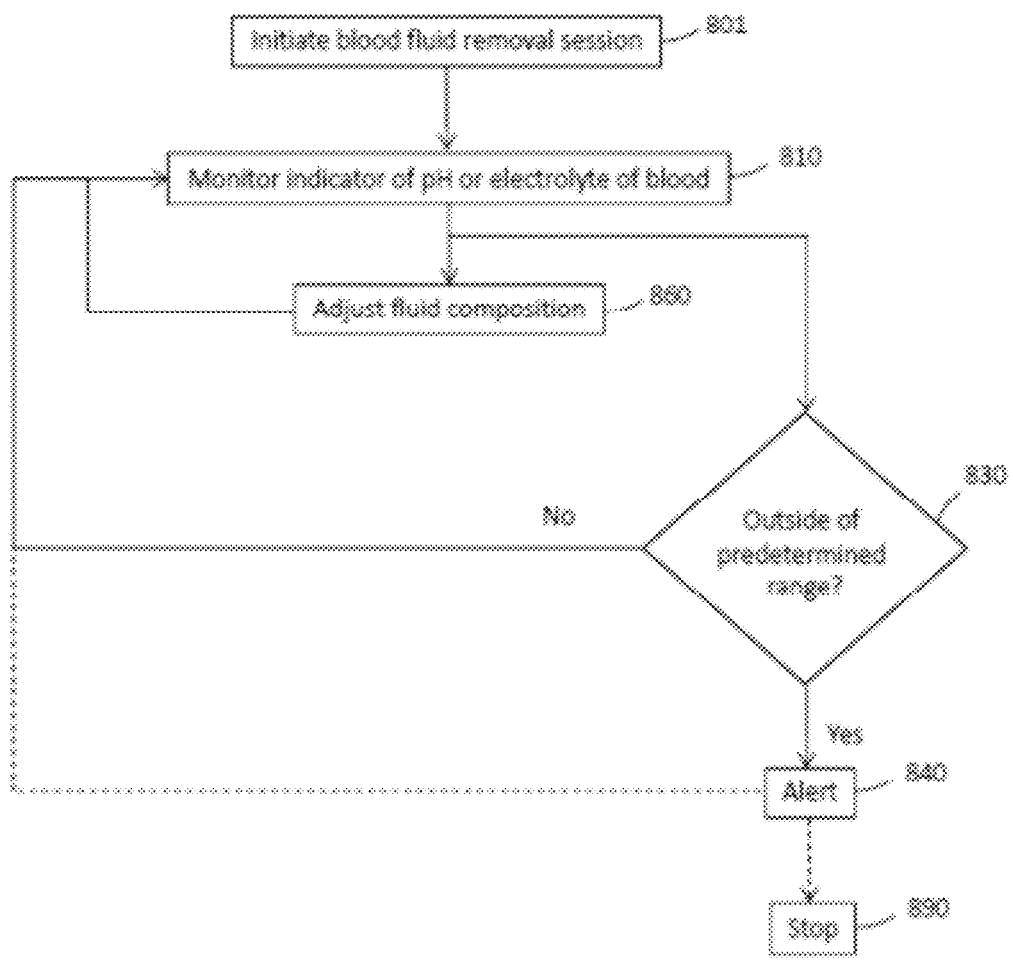
FIGS. 25-27 are flow diagrams depicting overviews of methods in accordance with certain embodiments described herein.

As described above, the composition of the dialysate traveling to the hemodialysis unit 15 can be adjusted by infusion set 35 and monitored by one or more sensors 74, 75, and 76. Further, one or more sensors for detecting electrolytes (e.g. $Ca^{2+}$, $Mg^{2+}$, $Na^+$, $Cl^-$) or monitoring electrolytes in the blood circuit 10. In certain embodiments, such sensor can be placed upstream of the hemodialysis unit 15 to measure the composition of blood under the hemodialysis unit 15 and downstream of the hemodialysis unit 15 to measure blood exiting the hemodialysis unit 15, wherein adjustment to the dialysate fluid can be made based upon a difference in signal between the upstream and downstream sensors. Referring now to FIG. 25, the depicted method includes initiating a blood fluid removal session 801 and monitoring an indicator pH or electrolyte concentration of blood 810; e.g. detecting pH or electrolytes in blood or in fluid from which pH or electrolyte levels in blood can be derived. Based on the monitored indicator of pH or electrolytes, the pH or electrolyte composition or concentration of fluid (e.g., dialysate or replacement fluid) used in the blood fluid removal session can be adjusted 860. For example, based on one or more of the current value of a monitored ionic species or the rate of change in the monitored ionic species, the fluid composition can be adjusted, e.g. as discussed above.

As shown in FIG. 25, continuous, periodic or intermittent determinations can be made as to whether the pH or electrolyte concentration is out of range 830 based on data acquired during the monitoring 810. For example, a determination 830 may be made as to whether pH or electrolyte levels crossed a threshold (e.g., a ceiling or floor). If the pH or electrolytes are determined to be within range, monitoring 810 can continue. If the pH or electrolytes are determined to be out of range (e.g., cross a threshold), an alert 840 can be issued to notify the patient or a healthcare provider of the situation. In some cases, the situation may warrant stopping 890 of the blood fluid removal session; e.g., if the detected pH or electrolytes are too far out of range or cross a heightened threshold. In other cases, it may be suitable to continue with the blood fluid removal session with heightened awareness of a situation for which increased attention may be warranted.

Figure 26:
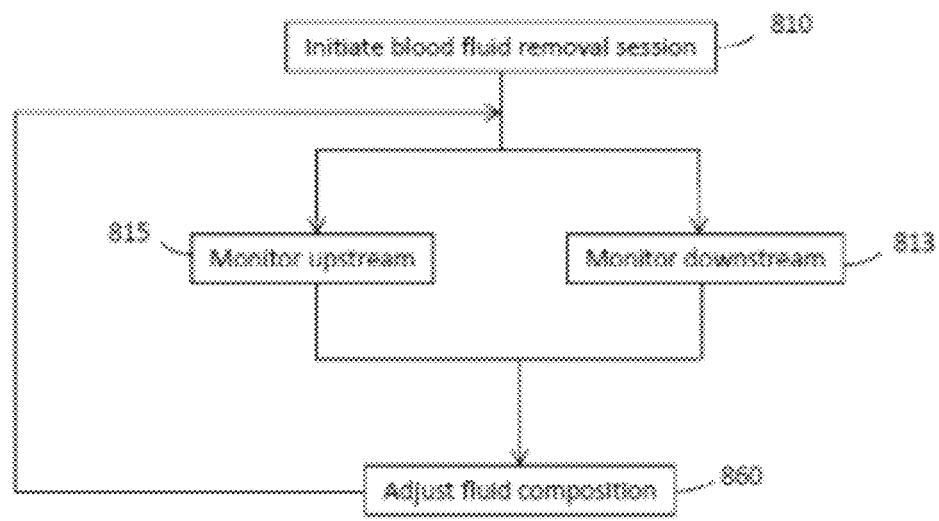

Referring now to FIG. 26, the depicted method includes initiating a blood fluid removal session 801 and monitoring an indicator pH or electrolyte concentration upstream 815 and downstream 813 of the hemodialysis unit 15. Data acquired from upstream and downstream sensors can be compared to determine how to adjust 860 the fluid composition, e.g. as described above.

Figure 27:
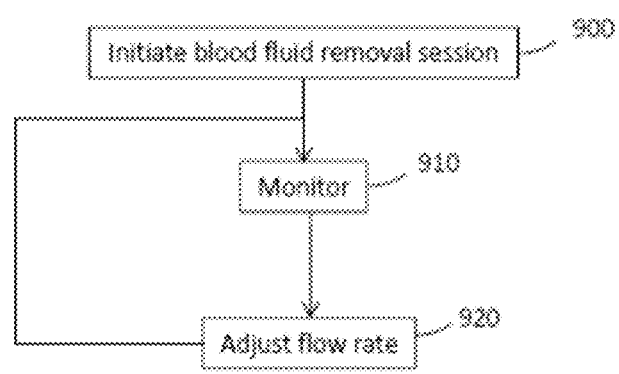

Referring now to FIG. 27, a method where blood electrolyte concentration or pH is adjusted by altering the flow rate of dialysate or blood is shown. The method includes initiating a blood fluid removal session 900, such as a hemodialysis session, and monitoring an indicator of pH or electrolyte 910, which can be in the patient, upstream of the device, downstream of the device, within the device, or the like. Based on the monitored data 910, adjustments to the flow of dialysate or blood may be made 920 to adjust the electrolyte concentration or pH in the blood that gets returned to the patient.

In additional embodiments, the composition of a dialysate can be changed or adjusted based on one or more cardiovascular (CV) parameters that can be monitored during a dialysis treatment session. A suitable external or implantable device can be used to measure certain CV parameters such as blood pressure (BP), heart rate and electrocardiogram (ECG) signals. One suitable implantable sensor device configured to monitor a patient's ECG signals is Medtronic, Inc.'s Reveal® series cardiac monitors. In some embodiments, a sensor device for measuring one or more CV parameters can be a suitably equipped pacemaker or defibrillator implanted in the patient. Monitored cardiac signals from such implanted devices can be transmitted to a dialysis device or other computing device for setting dialysis session parameters using the communication systems described herein. In further embodiments, suitable external ECG monitors, heart monitors and blood pressure sensing devices can be used to measure the one or more CV parameters. For example, a Holter sensor system can be configured to monitor ECG activity of the patient. An example of a suitable external blood pressure monitoring system is the wearable blood pressure monitor described in U.S. Pat. No. 7,674,231, "Wearable Pulse Wave Velocity Blood Pressure Sensor and Methods of Calibration Thereof", issued Mar. 9, 2010.

In certain embodiments, the one or more CV parameters can be selected from one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

One or more of the monitored CV parameters may be employed to set an appropriate prescription, such as dialysate composition, for the patient's next dialysis session or to adjust during a dialysis session. By way of example, if the patient's blood pressure is high or higher than typical for the patient, the rate of fluid removal can be increased. If the blood pressure is low or lower than typical for the patient, the rate of fluid removal can be decreased. If the patient's heart rate is high (e.g., higher than a predetermined threshold), the dialysate potassium concentration may be increased. A determination that potassium concentration requires adjustment based on a CV parameters can be performed regardless of any mass transfer of potassium that may be determined by the system.

Table 5 below provides some general examples of how an initial prescription or adjustments during a blood fluid removal session can be altered based on a monitored cardiovascular condition or parameter.

TABLE 5

Example alterations that may be taken based on cardiovascular monitoring

| Monitored Parameter | Status | Fluid Removal Rate | $K^+$ conc. | $Na^+$ conc. |
|---|---|---|---|---|
| Blood pressure | High | Increase | | Decrease |
| | Low | Decrease | | Increase |
| Heart rate | High | | Increase | |
| | Low | | Decrease | |
| Q-T interval | High | | Increase | |
| | Low | | Decrease | |

Monitoring of the one or more cardiovascular parameters can occur before, during or after a dialysis session where a dialysis treatment parameter, such as dialysate composition, is changed. If the patient's cardiovascular conditions continue to worsen following an adjustment, the dialysis session change cam be reversed or a different change can be made. If the patient's cardiovascular condition improves following the dialysis session parameter change, the parameter change can remain in effect for a period of time or other changes can be made to determine whether further improvements are achievable. The blood fluid removal parameters can be changed one at a time, or more than one at a time can be changed based on patient safety concerns or patient history. For example, if the patient has previously presented with a particular status of a particular condition or combination of conditions and has previously responded favorably to certain combinations of dialysis session parameter adjustments, it be desirable to simultaneously implement such adjustments. Systems and methods for basing parameters on patient history before, during or after a dialysis session are described in Provisional Patent Application No. 61/480,539, and U.S. patent application Ser. No. 13/424,533, filed Mar. 20, 2012, both entitled ADAPTIVE SYSTEM FOR BLOOD FLUID REMOVAL, filed Apr. 29, 2011, which applications are hereby incorporated herein by reference in their entirety.

Figure 28:
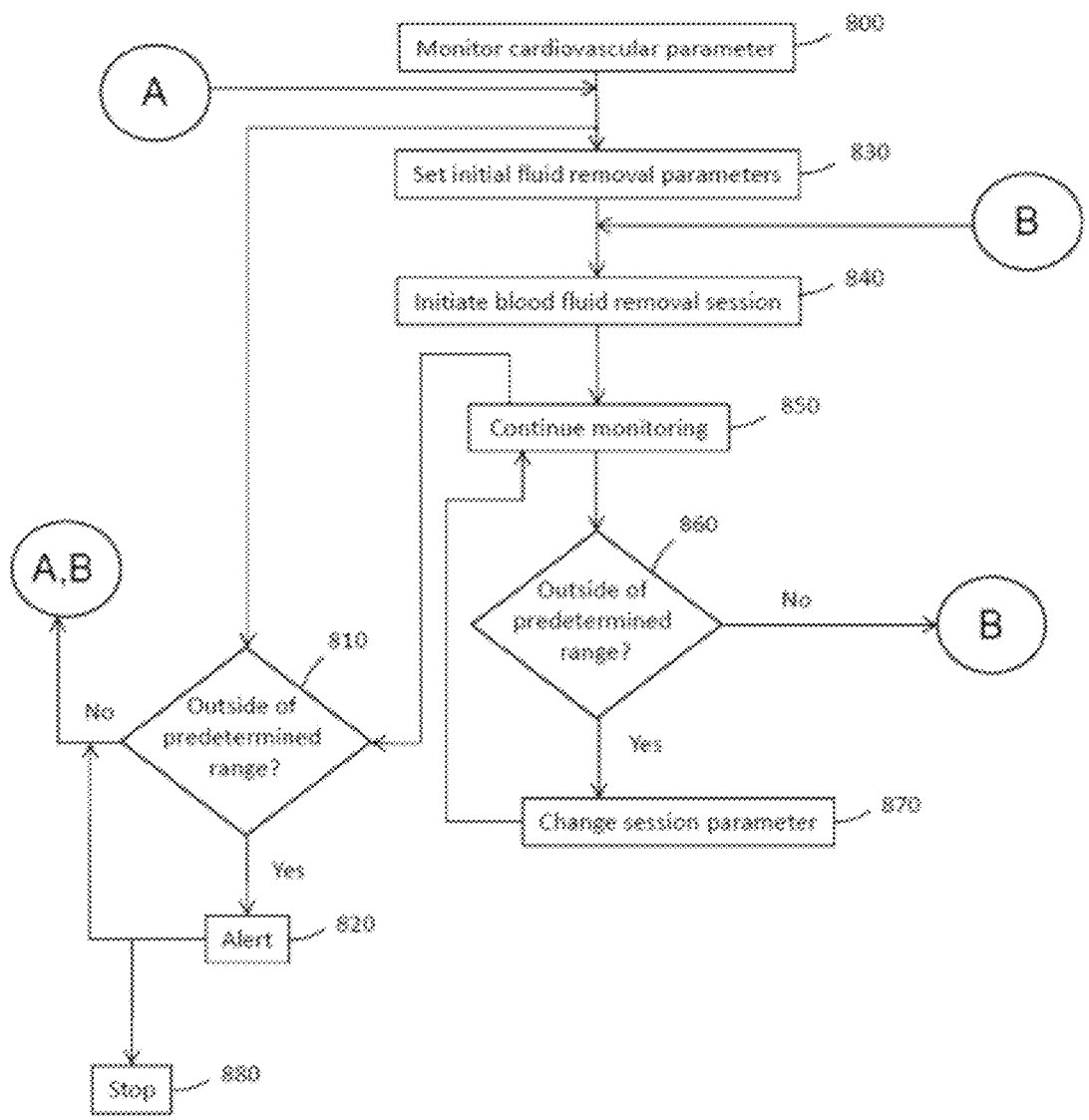
FIGS. 28-29 are flow diagrams depicting overviews of methods in accordance with certain embodiments described herein.

Referring now to FIG. 28, the depicted method includes monitoring a cardiovascular parameter of the patient 800, as discussed above. The monitoring 800 can be chronic or periodic and can employ one or more implantable or wearable sensors. The method further includes determining whether the monitored cardiovascular parameter is outside of a predetermined range 810. If the parameter is determined to be outside of the predetermined range, an alert may be issued 820. The alert can be an alert to the patient, such as a vibration or audible alarm emitted from the sensor or a device in communication with the sensor. The alert can be to a healthcare provider communicated through any of the communication systems described herein.

If the monitored cardiovascular parameter is determined not to be outside the range, data acquired during monitoring 800 is used to set initial parameters of a blood fluid removal session are set 830. The initial parameters of the session can include blood fluid removal rate, profile, or amount, the composition and concentration of components of fluid used during the session, such as dialysate or replacement fluid, and the like. As described above, the ability to chronically cardiac parameters of the patient provides the ability to tailor the parameters of a blood fluid session prior to each session, as opposed to current standard practice in which the fluid composition is adjusted on a monthly basis (or thereabout). As multiple blood fluid removal sessions (e.g., two to three a week) may occur with a month, setting the session parameters on a monthly basis may result in the patient undergoing several blood fluid removal sessions with session parameters that may no longer be well suited for the patient.

Still referring to FIG. 28, once the initial session parameters are set 830, the blood fluid removal session an be initiated 840 and monitoring of the cardiovascular parameters continued 850. A determination may be made as to whether the monitored cardiovascular parameter is outside of a first, higher threshold range 810 or a second, lower threshold range 860. If the parameter is outside of the first range 810, an alert 820 may be provided (e.g., as discussed above) and, in some cases, the blood fluid removal session may be stopped 880. If the cardiovascular parameter is not outside of the first range 810 but is outside the second range (860), a parameter of the dialysis session may be changed 870 based on the monitored cardiovascular parameter (e.g., as discussed above). Further changes may be made in a similar manner as needed.

If the cardiovascular parameter is not outside of the first range 810 or the second range 860, the blood fluid session may continue with the initially set parameters.

Figure 29:
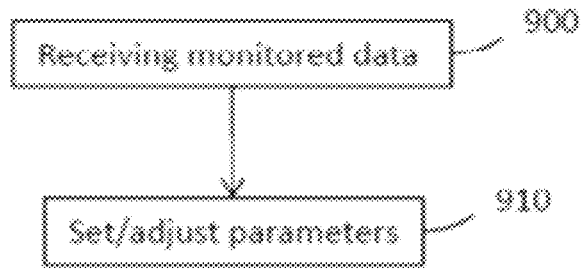

Referring now to FIG. 29 a method carried out by a blood fluid removal or dialysis system or device is shown. The method includes receiving data regarding a monitored cardiovascular parameter 900 and setting or adjusting a parameter of a blood fluid removal session based on the received data. The system or device has control electronics configured to set or adjust the session parameter based on the received data regarding the cardiovascular parameter.

Detection of Membrane Fouling

In certain embodiments, a controlled compliance dialysate circuit 20 is a controlled compliance dialysis circuit as discussed above. In such a dialysate circuit, the flow of fluid between the blood circuit 10 and the dialysate circuit 20 can be controlled through the adjustment of pump rates since the amount of dialysate fluid in the dialysate circuit 20 is a limited or known volume. As such, a change in pressure measured by any of the pressure sensors described above can provide an indication of fouling of a membrane within the hemodialysis unit 15. That is, a fouled membrane will cause excessive high or low pressure in parts of the system during ultrafiltration if the membrane is fouled in a manner that impedes fluid flow across the membrane. However, in some embodiments, a controlled compliance dialysate circuit may not be employed, where the amount of fluid within the dialysate circuit can fluctuate during operation. In such embodiments, the system can nevertheless still be monitored to evaluate the performance of the membrane within the hemodialysis unit 15.

In additional embodiments, the membrane within the hemodialysis unit 15 can be monitored for efficiency in passing dissolved solutes (e.g., urea, electrolytes, etc.) regardless of whether the membrane is further used for ultrafiltration and bulk fluid passage. Such monitoring can be employed for a dialysate circuit 20 that is a controlled compliance circuit.

In certain embodiments, a sensor is configured to monitor an indicator of fluid flow rate. The sensor can employ any suitable flow meter, such as an acoustic Doppler velocimeter, an optical flow meter, a thermal flow meter, a Venturi meter, in-fluid paddle type meter, or the like. In some embodiments, a pressure sensor is used and the flow is calculated based on the pressure and the known diameter of the tubing through which the fluid flows. Such flow meters and components thereof are known in the art and can be readily adapted for use herein.

In certain embodiments, one or more pressure sensors are used to measure differential pressure across a dialysis membrane for purposes of monitoring membrane performance. For example, an increased relative pressure upstream of membrane (e.g., fluid entering the hemodialysis unit 15), or portion thereof, can indicate decreased performance of the membrane (e.g., fouling). By way of further example, a decreased relative upstream pressure can be indicative of a rip or tear in, for example, a membrane.

In certain embodiments, a sensor is configured to monitor an indicator of a compound in blood or in fluid removed from the blood. The sensors can be configured to monitor components of blood that are configured to be removed during hemodialysis. Examples of such compounds include urea, creatinine, sulfate, phosphate, β-2-microglobulin, or the like. Sensors capable of measuring such compounds are known in the art and can be readily adapted for used herein. For example, Nova Biomedical manufactures a variety of sensors capable of detecting components in blood such as creatinine, phosphate, urea and the like, which sensors can be employed or adapted for use herein. Other urea sensor detection technology that may be employed or adapted for used herein is described by Zhong et al., Clin. J. Biotechnol. 1992; 8(1):57-65. β-2-microglobulin sensor detection technology that may be employed or adapted for used herein is described by Brynda et al., Biosens Bioelectron. 1999; 14(4):363-8 and by Nedelkov et al., Proteomics. 2002; 2(4):441-6. Any suitable sensor technology can be employed and the sensor can be placed at any point on the dialysate circuit 20 between the hemodialysis unit 15 and the control pump 102 or other point where fluid is removed or added to the dialysate circuit 20.

In some embodiments, multiple redundant sensors on the same upstream or downstream position relative to the hemodialysis unit 15 can be present on the dialysis circuit 20 to improve accuracy and reliability. In some embodiments, a sensor can have more than one transducer or sensing mechanism to detect more than one compound in blood or to detect a compound in blood and flow rate. In some embodiments, sensors for the same compound may be configured to accurately detect different ranges of concentrations of the compound. In embodiments, more than one transducer is present in a single unit. This allows for convenient data collection and circuitry, as all the data may be collected in one place at the same time.

Figure 30:
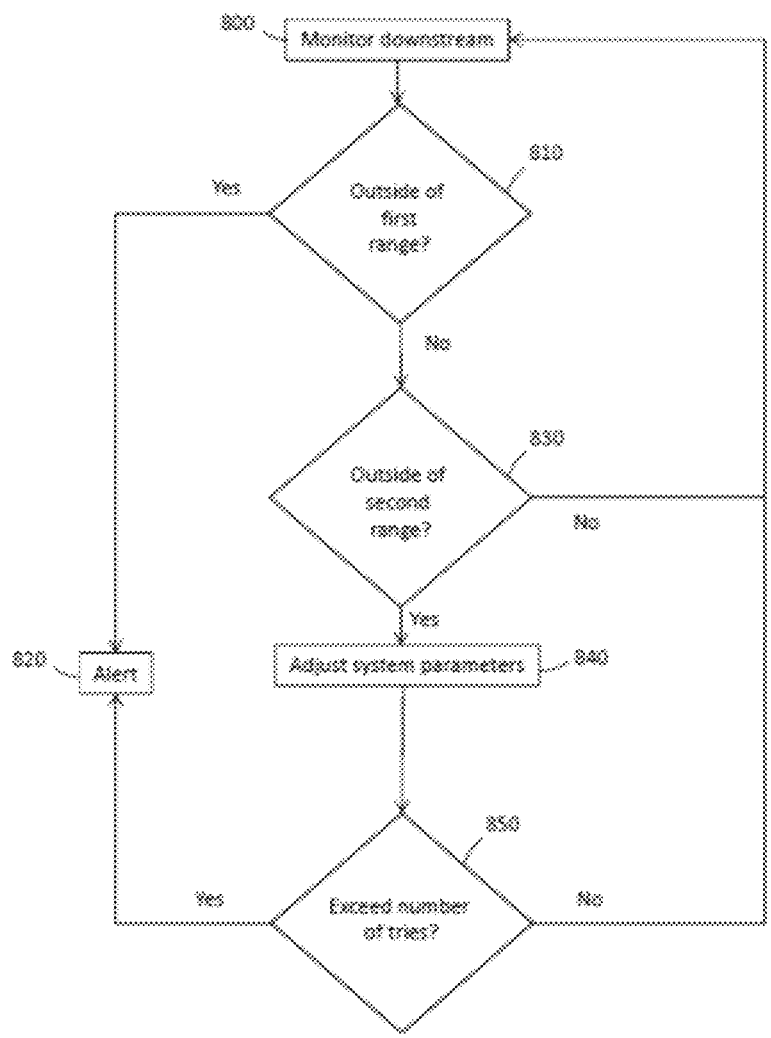
FIGS. 30-34 are flow diagrams depicting overviews of methods in accordance with certain embodiments described herein.

Referring now to FIG. 30 an example of a method for monitoring the performance of a dialysis membrane for ultrafiltration or hemodialysis unit (i.e. medium) is shown. The method includes monitoring a condition downstream of the membrane 800. The condition can be, for example, flow rate of fluid exiting the hemodialysis unit 15, the concentration of a compound (e.g., waste product) in fluid or blood exiting the hemodialysis unit 15, or the like. The depicted method includes determining whether a value of the monitored condition is outside of a first heightened range. If the value of the monitored parameter is outside of the first range (e.g. upper limit), an alert may be issued 820. If the value is not outside of the first heightened range, a determination as to whether the value of the monitored condition is outside of a second less heightened range 830. If the value is not outside of the second range, monitoring 800 may continue. If the value is determined to be outside the second range (e.g., lower limit), one or more system parameters, such as blood flow rate, dialysate flow rate, negative pressure application, or the like, can be adjusted 840 and monitoring 800 can continue. In some cases, it may be desirable to limit the number of attempts to adjust system parameters 840 to bring the medium performance within a desired range. If a predetermined number of tries is exceeded 850 or set amount of time passes without bring the medium performance within a desired range (i.e., within the second range, 830), an alert can be issued 820.

Figure 31:
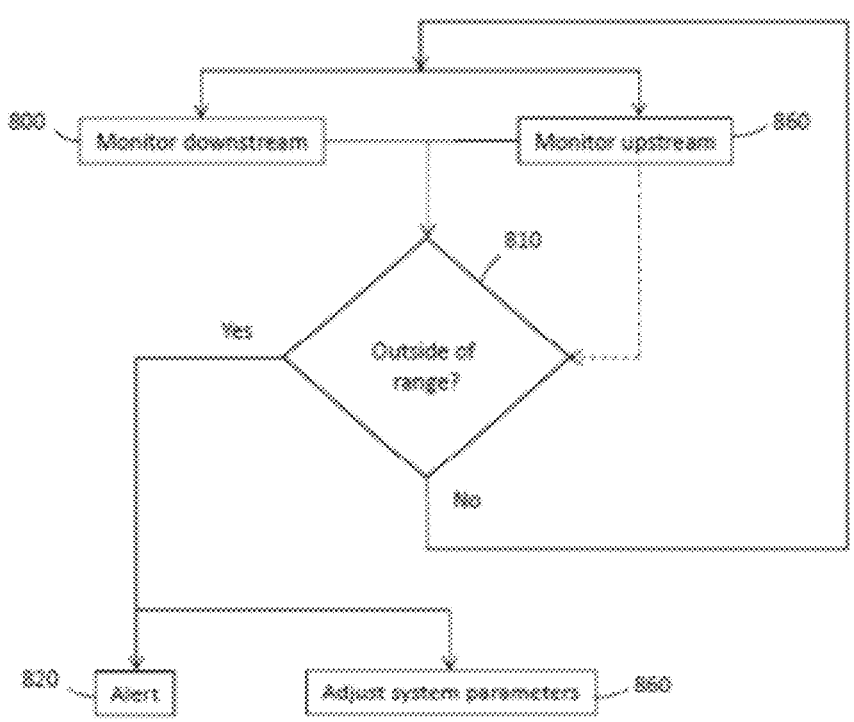

Referring now to FIG. 31 a method for monitoring the performance of a dialysis membrane employing monitoring downstream 800 and upstream 860 of the hemodialysis unit 15 is shown. The upstream monitoring 860 can include monitoring flow rate of blood, pressure, or concentration of a compound, such as a waste product, in blood before the blood enters the medium. A value of the upstream monitoring can be used in determining what constitutes and appropriate range of medium performance 810. In the depicted embodiment, values associated with the upstream 860 and downstream 800 monitoring are compared and a determination is made as to whether the compared values are indicative of the medium performance being out of range 810. If the values are determined not to be indicative of membrane performance being out of range (e.g., fouled, inefficient removal of waste product or fluid, etc.), monitoring 800, 860 can continue (e.g., as discussed above with regard to FIG. 31). If the values are determined to be indicative of medium performance being out of range, an alert can be issued 820.

Figure 32:
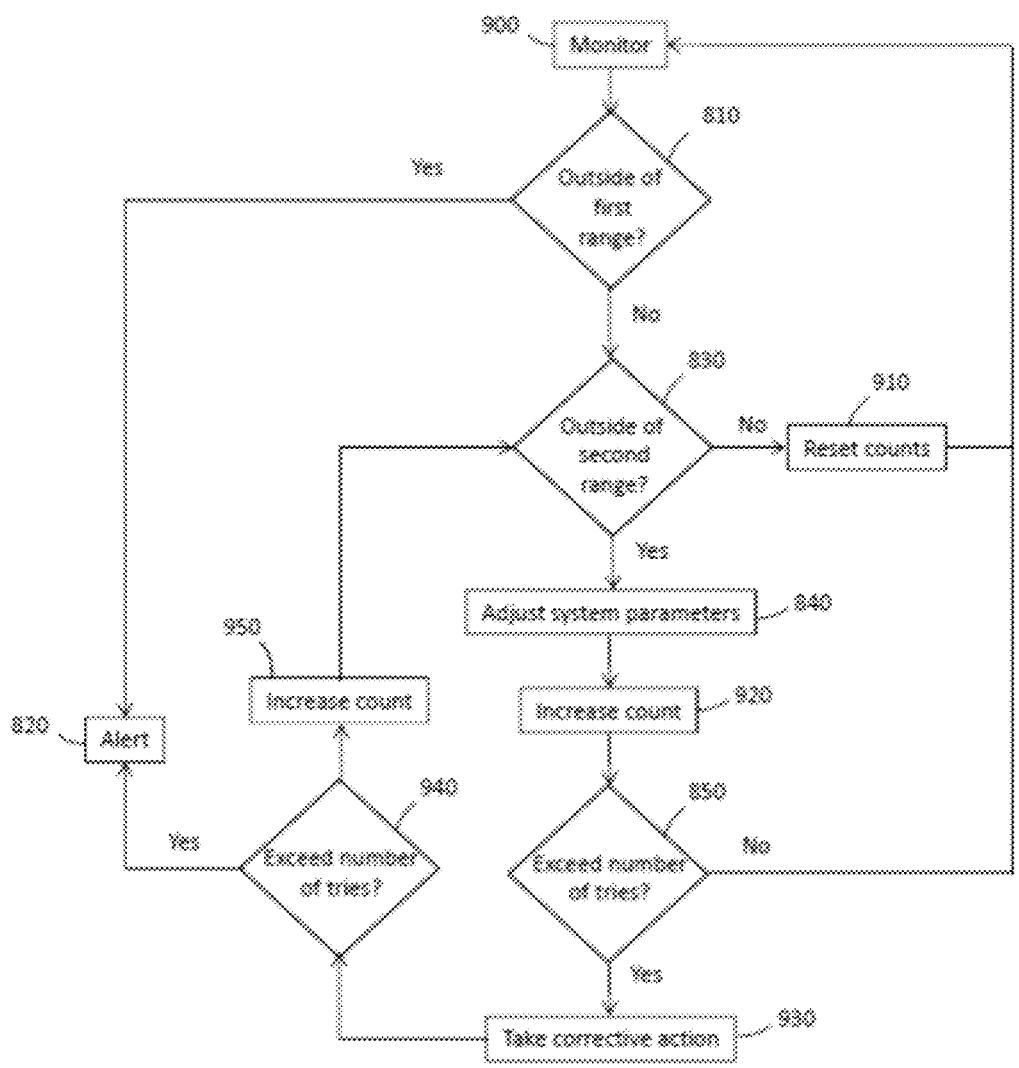

Referring now to FIG. 32, a method is shown that includes maintaining or returning system parameter values to values within a desired range and taking corrective action if the values do not return to the desired range. Aspects of these methods may be performed independently if desired. In the depicted embodiment, a system parameter is monitored 900. The monitoring can be upstream of the hemodialysis unit 15, downstream of the hemodialysis unit 15, or within the hemodialysis unit 15. If a value of the monitored parameter is outside of a first range 810, which may be indicative of more serious system inefficiency or malfunction, an alert 820 can be issued. If the value of the system parameter is determined not to be outside of the first range 810, a determination can be made as to whether the parameter is outside of a second range 830, which may be indicative of a less serious inefficiency or malfunction. If the value is not outside of the second range (i.e., the system is performing as expected), counts 910 can be reset, and monitoring 900 can continue. Additional detail regarding resetting counts 910, which refers to adjustment to system parameters so that monitored values will fall within desired ranges and correcting a cause or source of system inefficiencies or malfunctions, will be discussed below.

If the monitored value is determined to be outside of the second range 830, a modification or adjustment system parameters 840 may be made to return system performance to desired levels (e.g., monitored values fall within second range), e.g., as discussed above with regard to FIG. 30. Before or after adjusting the system parameters 840, a count of the number of corrective attempts or adjustment made can be increased 920. Alternatively or in addition, a timer can be started. A determination can then be made as to whether the number of attempts or time has been exceeded 850. If the number of tries has been exceeded, corrective action can be taken 930 in an attempt to address a cause or source of the malfunction. By way of example, actions may be taken to de-foul or clean a membrane. Examples of how this may be done are presented below with regard to FIG. 32. A determination can be made as to whether a preset number of tries (or time) to address a cause or source of the system inefficiency or malfunction has been attempted 940. If the number of tries has been exceeded, an alert may be issued 820. The count of the number of tries 950 can be increased at any point after taking corrective action 930. If the count or time does not exceed the preset count or time, a determination can be made as to whether the corrective action resulted in the monitored values returning to within the second range 900. If yes, the counts (i.e., counts 920 and 950) can be reset.

Figure 33:
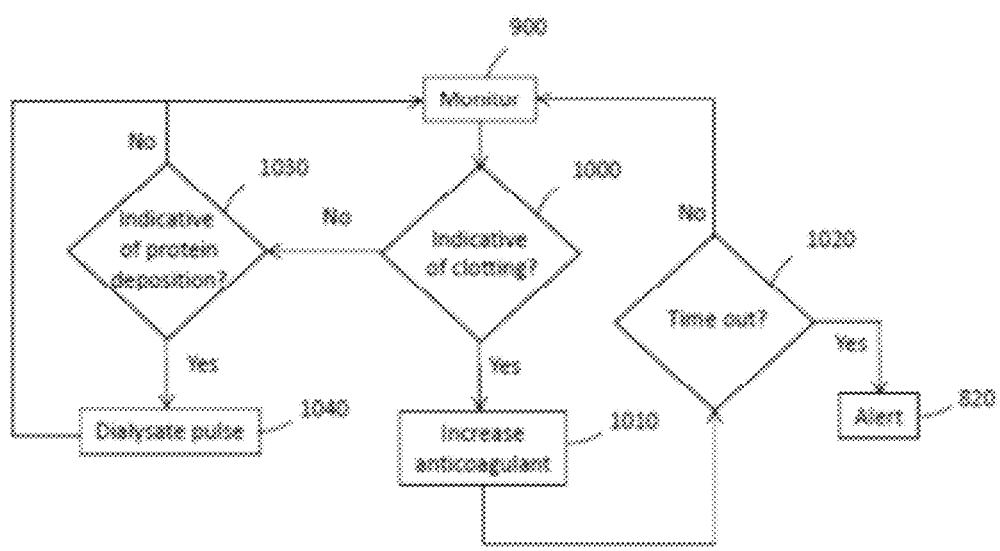

Referring now to FIG. 33 an example of a method for detecting an under-performing membrane and for cleaning or de-fouling the membrane or medium is shown. Severity of fouling of a membrane or medium in contact with blood is most often due to depositing of proteins or clotting factors on the medium, which can lead to blood clotting on medium. During initial protein deposition, medium performance should not be significantly compromised. However, as more protein deposits or initial clotting develops, the performance of the medium will further deteriorate until significant clotting or protein deposition renders the medium ineffective.

FIG. 33 depicts a method in which the medium includes a membrane and the system employs dialysate, such as with a hemodialysis system. However, it will be understood that similar methods may be employed in other types of systems and other types of media; e.g. sorbents. As indicated in FIG. 33, membrane performance can be monitored 900; e.g. as discussed above with regard to pressure differential, flow rates, concentration of chemical species, etc. A determination may be made as to whether a monitored value is indicative of clotting 1000; e.g., a high level of membrane inefficiency. If yes, an increase in anticoagulant agent can be added to the blood or dialysate 1010 in an attempt to prevent further clot formation or a thrombolytic agent may be added to dissolve the clot. A pump or other suitable means for adding an anticoagulant can be placed at any appropriate location on the blood circuit 10 between the blood access point 5 and the hemodialysis unit 15. As discussed above, it may be desirable to stop blood flow or divert blood flow during times thrombolytic agents are being employed. If the monitored value remains indicative of clotting after a predetermined amount of time 1020 after administration of increased concentrations of anticoagulant or thrombolytic agent (or after sequential increases in anticoagulant reach a predetermined upper limit), an alert may be issued 820. If, however, the monitored value is not indicative of clotting, a determination may be made as to whether the monitored value is indicative of a predetermined degree of protein deposition 1030, and a pulse of dialysate 1040, sustained increased dialysate flow or the like, may be delivered in an attempt to clear the deposited proteins from the membrane, and the process repeated.

It will be understood that the order of the steps in FIG. 33 are shown only for purposes of illustration and that the method may be performed in any other suitable order (e.g., step 1030 may be performed before step 1000). Media, such as membranes, or systems may be readily calibrated by one of skill in the art such that changes in monitored values can be attributed to certain degrees of fouling.

Figure 34:
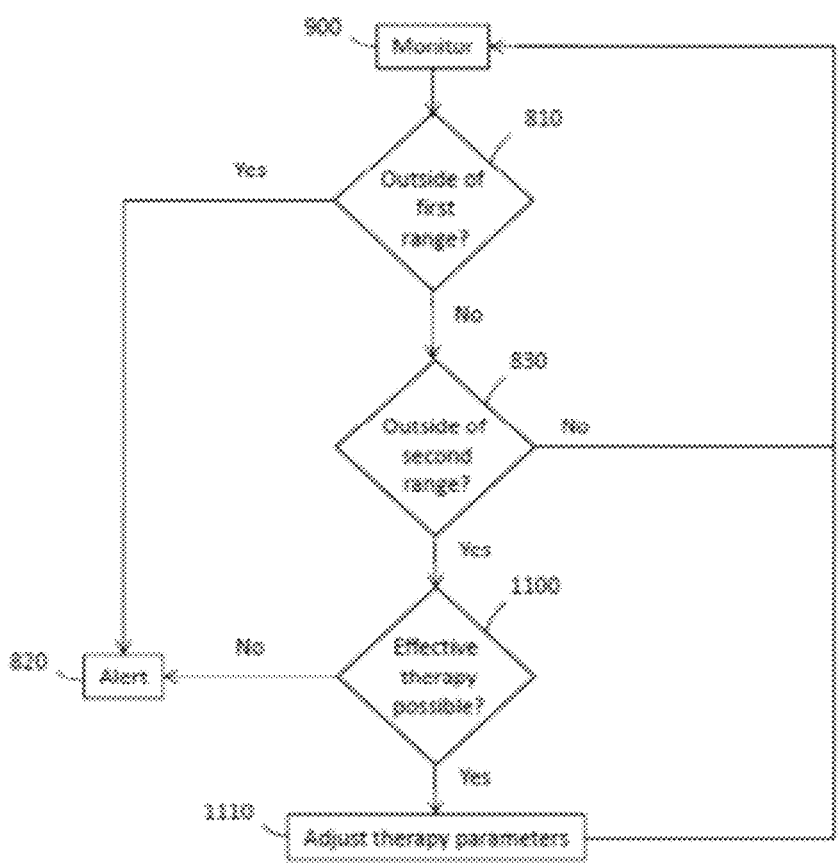

Referring now to FIG. 34 a method is depicted in which therapy proceeds despite monitored parameters indicating poor system performance. In the depicted embodiment, a system parameter is monitored 900. The monitoring may be upstream of the medium, downstream of the medium, or within the medium or medium chamber. If a value of the monitored parameter is outside of a first range 810, which may be indicative of more serious system inefficiency or malfunction, an alert 820 may be issued. If the value of the system parameter is determined not to be outside of the first range 810, a determination may be made as to whether the parameter is outside of a second range 830, which may be indicative of a less serious inefficiency or malfunction. If the value is not outside of the second range (i.e., the system is performing as expected) monitoring 900 and therapy may continue. If, however, the value is outside of the second range 830, a determination may be made as to whether effective therapy may be delivered 1100 despite the poor system performance (as measured by the monitored parameter). For example, it may be determined that the medium is not performing efficiently (e.g., slow rate of waste product or fluid removal from blood), but that an extended session time may be acceptable for achieving therapeutic goals. The therapy parameters may be adjusted 1110; e.g., extend session time, and the process continued.

Automated Updating of Dialysis Parameters

In various embodiments described herein, a method includes (i) initiating a blood fluid removal or dialysis session, which may herein be referred to as a blood fluid removal session, with initial system parameters; (ii) acquiring a first set of data regarding one or more patient physiological parameters; (iii) storing the first data set in a "best" or "most effective to date" data set memory; (iv) associating the initial system parameters in an increased effectiveness lookup table with the first data set; (v) adjusting at least one parameter of the blood fluid removal session to arrive at adjusted system parameters; (vi) acquiring a second set of data regarding the one or more patient physiological parameters after the at least one parameter of the blood fluid removal session has been adjusted; and (vii) if at least one value of the second data set is closer to the target value than a corresponding value of at least one value of the first data set: replacing the first data set in the most effective to date data set memory with the second data set; storing in the increased effectiveness lookup table data regarding the second data set; and associating data regarding the adjusted system parameters with the second data set.

Figure 35:
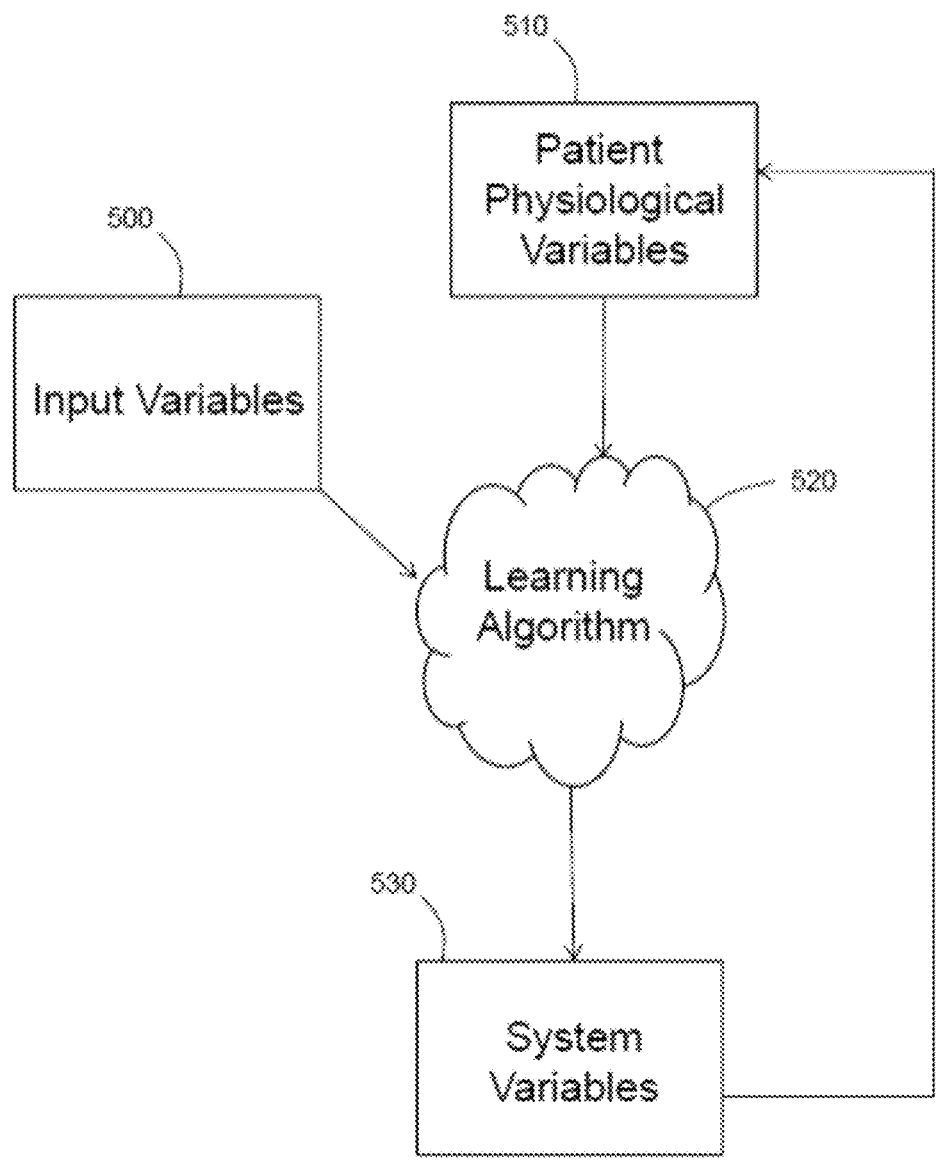
FIGS. 35-41 are flow diagrams illustrating methods in accordance with various embodiments described herein.

As shown in FIG. 35 a algorithm 520, based on input variables 500, and patient physiological variables 510 can determine appropriate system variables 530 to employ based on the patient's history with blood fluid sessions under the algorithm. During a blood fluid session, system variables 530 may be changed and the patient physiological response may be monitored in response to the changed system variables. If one or more of the patient's physiological variables 510 improve or become "more effective", the algorithm 530 can associate the changed system variables 530 with the increased effectiveness patient outcome so that the changed system variables 530 may be used later in the session or in a future session when the patient has a similar set of physiological variables 510. If one or more of the patient's physiological variables 510 become less effective, the algorithm 530 can associate the changed system variables 530 with a less effective patient outcome so that the changed system variables 530 may be avoided later in the session or in a future session when the patient has a similar set of physiological variables 510.

In embodiments, the physiological variables 510 are monitored by sensors that feed data regarding the variables directly into the algorithm 520 or electronics running the algorithm. The sensors may monitor fluid volume in the patient's blood; fluid volume in the patient's tissue; concentrations of electrolytes in the patient's blood; pH of the patient's blood; one or more cardiovascular parameter of the patient, such as blood pressure, heart rhythm, heart rate; or combinations or indicators thereof. The sensors may monitor the patient physiological parameters before, during or after a blood fluid removal session.

Any suitable sensor may be employed. Examples of sensors and systems that may be employed with regard to blood fluid volumes and tissue fluid volumes are discussed in U.S. Provisional Patent Application No. 61/480,528, filed on Apr. 29, 2011, and U.S. patent application Ser. No. 13/424,454 filed Mar. 20, 2012, both entitled FLUID VOLUME MONITORING FOR PATIENTS WITH RENAL DISEASE; and U.S. Provisional Patent Application No. 61/480,530, filed on Apr. 29, 2011, and U.S. patent application Ser. No. 13/424,467 filed Mar. 20, 2012, both entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well-studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or underloaded. The data acquired by impedance sensor and input data regarding fluid status of the patient at the time the sensor data is acquired may be used to establish suitable ranges for impedance values.

Examples of sensors and systems for monitoring pH and electrolyte concentration are disclosed in U.S. Provisional Patent Application No. 61/480,532, filed on Apr. 29, 2011, and U.S. patent application Ser. No. 13/424,479 filed Mar. 20, 2012, both entitled ELECTROLYTE AND pH MONITORING FOR FLUID REMOVAL PROCESSES, which applications are hereby incorporated herein by reference in their entirety to the extent that they do not conflict with the present disclosure. Of course, any suitable sensor or systems for monitoring pH and electrolyte concentration may be used. For example, a transducer may be employed to detect pH or electrolytes. Suitable transducers may include an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein. One or more sensors may be employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components. A sensor (or transducer) for detecting pH, electrolyte concentration, or the like may be placed at any suitable location for purposes of monitoring electrolytes or pH. For example, the sensor may be implanted in the patient, located external to the patient an upstream of a blood fluid removal device, located external to the patient and downstream of the blood fluid removal device, or the like.

Examples of sensors and systems for monitoring cardiovascular parameters are disclosed in U.S. Provisional Patent Application No. 61/480,535, filed on Apr. 29, 2011, and U.S. patent application Ser. No. 13/424,490 filed Mar. 20, 2012, both entitled CARDIOVASCULAR MONITORING FOR FLUID REMOVAL PROCESSES, which applications are hereby incorporated herein by reference in their entirety to the extent that they do not conflict with the present disclosure. Of course, any suitable sensor for monitoring cardiovascular parameters may be used. In embodiments, pH or electrolyte sensors; e.g., as described above, may be used to monitor cardiovascular parameters. Sensors for monitoring heart rate or heart rhythm may be used. One suitable implantable sensor device that is configured to monitor a patient's ECG signals is a Medtronic, Inc.'s Reveal® series insertable cardiac monitor. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session. Blood pressure monitors, which may be external or implantable (such as Medtronic Inc.'s active leadless pressure sensor (ALPS), which generally takes the form of a stent to anchor the device within a vessel, may be employed. Such a device may be placed in any suitable blood vessel location, such as in a femoral artery or pulmonary artery. A wearable sensor system, such as a Holter sensor system, may be used to monitor ECG activity of the patient. Regardless of whether the sensor or sensor system employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

As indicated above, sensors for monitoring patient physiological parameters may be, or may have components that are, implantable or wearable. In embodiments, multiple sensors may be connected via telemetry, body bus, or the like. The connected sensors may be of the same or different type (e.g., pH or impedance). Such connected sensors may be placed (e.g., internal or external) for purposes of monitoring at various locations of the patient's body.

Monitoring may alternatively or additionally include receiving patient or physician feedback regarding the patient's state. For example, the patient may indicate a point in time when cramping begins, which often happens when too much fluid is removed. The blood fluid monitoring device may include an input, such as a keyboard or touch screen display for entering such data. Alternatively, a separate device such as a patient programmer, laptop computer, tablet computer, personal data assistance, smart phone or the like may be used to input the data; or the like.

Figure 36:
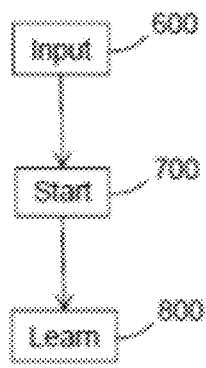

Referring now to FIG. 36 a high level flow diagram of a method is described. The method includes providing input 600, such as input variables discussed above with regard to FIG. 35 to a blood fluid removal system. The method also includes initiating or starting 700 a blood fluid removal session, and learning 800 from the session. The learning 800 may be as discussed above with regard to FIG. 35 with system parameters being varied and patient physiological parameters being monitored to determine which system parameter adjustments result in desirable patient physiologic outcomes.

Figure 37:
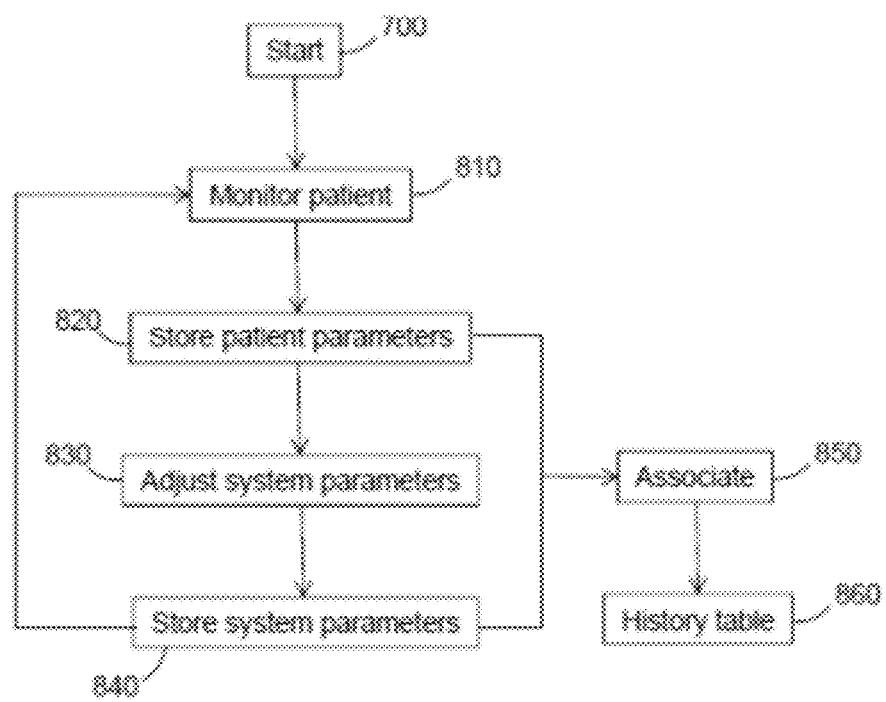

For example and with reference to FIG. 37, additional detail regarding an embodiment of a learning process that may occur during a blood fluid removal session is shown. The blood fluid removal session is started 700 and the patient is monitored 810. Monitored patient parameters, such as patient physiological variables as discussed above, are stored 820; e.g., in memory of the blood fluid removal system. The system parameters, such as system variables described above, which may include rate of fluid removal from the blood or electrolyte concentration of a dialysate or replacement fluid, are adjusted 830 and the system parameters are stored 840; e.g., in memory of the blood fluid removal system, dialysis system or monitoring system, and patient monitoring 810 continues. The set of stored patient parameters 820 are associated 850 with a set of stored system parameters 840 so that the system may recall particular system parameters that were employed at the time the patient had a given set of parameters. The data regarding the stored patient parameters (820) and the stored system parameters 840 may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to changing system parameters (860).

Figure 38:
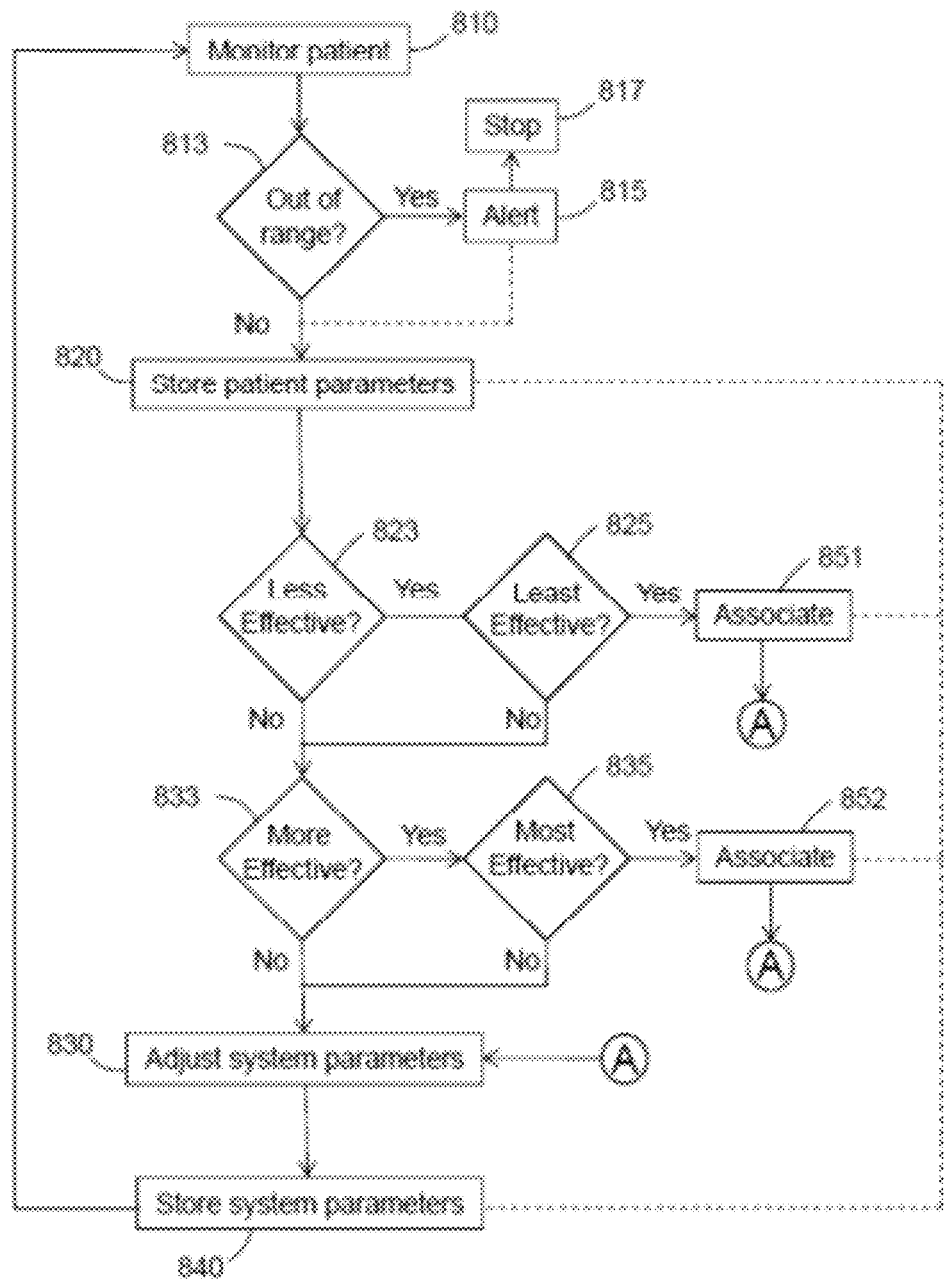

A more detailed embodiment is presented in FIG. 38. In the embodiment depicted in FIG. 38, patient is monitored 810 during a blood fluid removal session. It may be desirable to determine whether data acquired from patient monitoring is out of range 813. As used herein, "out of range" means that a value of a monitored parameter exceeds (i.e., is above or below) a predetermined range of values. The predetermined range of values may be indicative of a patient safety concern. If the data is out of range, an alert may be issued 815 or the session may be stopped 817. In some cases, it may be desirable to continue with the session, even if the monitored data or some aspect thereof is out of range. In the depicted embodiment, if the session is continued, (e.g., due to choice or to the monitored data not being out of range), data regarding the monitored patient parameters is stored 820 and is compared to stored patient data previously obtained (e.g., in a prior session or earlier in the session). A determination may be made as to whether the present patient parameter data is less effective 823 than stored patient parameter data resulting from system parameter adjustments 830 that occurred just prior to the current set of system parameters. If the data is determined to be less effective 823, the stored current patient parameters 820 may be associated 851 with stored current system parameters 840; e.g., as discussed above. In some cases, it may be desirable to determine whether the current patient parameter data, or a portion or aspect thereof, is the least effective that has been detected in the patient in a current or previous blood fluid removal session 825; e.g. by comparing the current patient data to a history of collected patient data. If the current patient data is the least effective observed 825 to date, the stored current patient parameters 820 may be associated 851 with stored current system parameters 840. In this way, only the "least effective" patient conditions are tracked, as opposed to all patient conditions, which can save on memory and processing power. In any case, once the patient and system parameter data is associated 851, the system parameters may be adjusted 830 and the process repeated.

If the present patient parameter data is determined to not be less effective than stored patient parameter data resulting from system parameter adjustments that occurred just prior to the current set of system parameters, a determination may be made as to whether the present patient parameter data is more effective 833 than stored patient parameter data resulting from system parameter adjustments 830 that occurred just prior to the current set of system parameters. If the data is determined to be more effective 833, the stored current patient parameters 820 may be associated 852 with stored current system parameters 840; e.g., as discussed above. In some cases, it may be desirable to determine whether the current patient parameter data, or a portion or aspect thereof, is the most effective that has been detected in the patient in a current or previous blood fluid removal session (835); e.g. by comparing the current patient data to a history of collected patient data (e.g., "history table" in FIG. 37). If the current patient data is the most effective observed 835 to date, the stored current patient parameters 820 may be associated 852 with stored current system parameters 840. In this way, only the "best" or most effective patient conditions are tracked, as opposed to all patient conditions, which can save on memory and processing power. In any case, once the patient and system parameter data is associated 852, the system parameters may be adjusted (830) and the process repeated.

Figure 39:
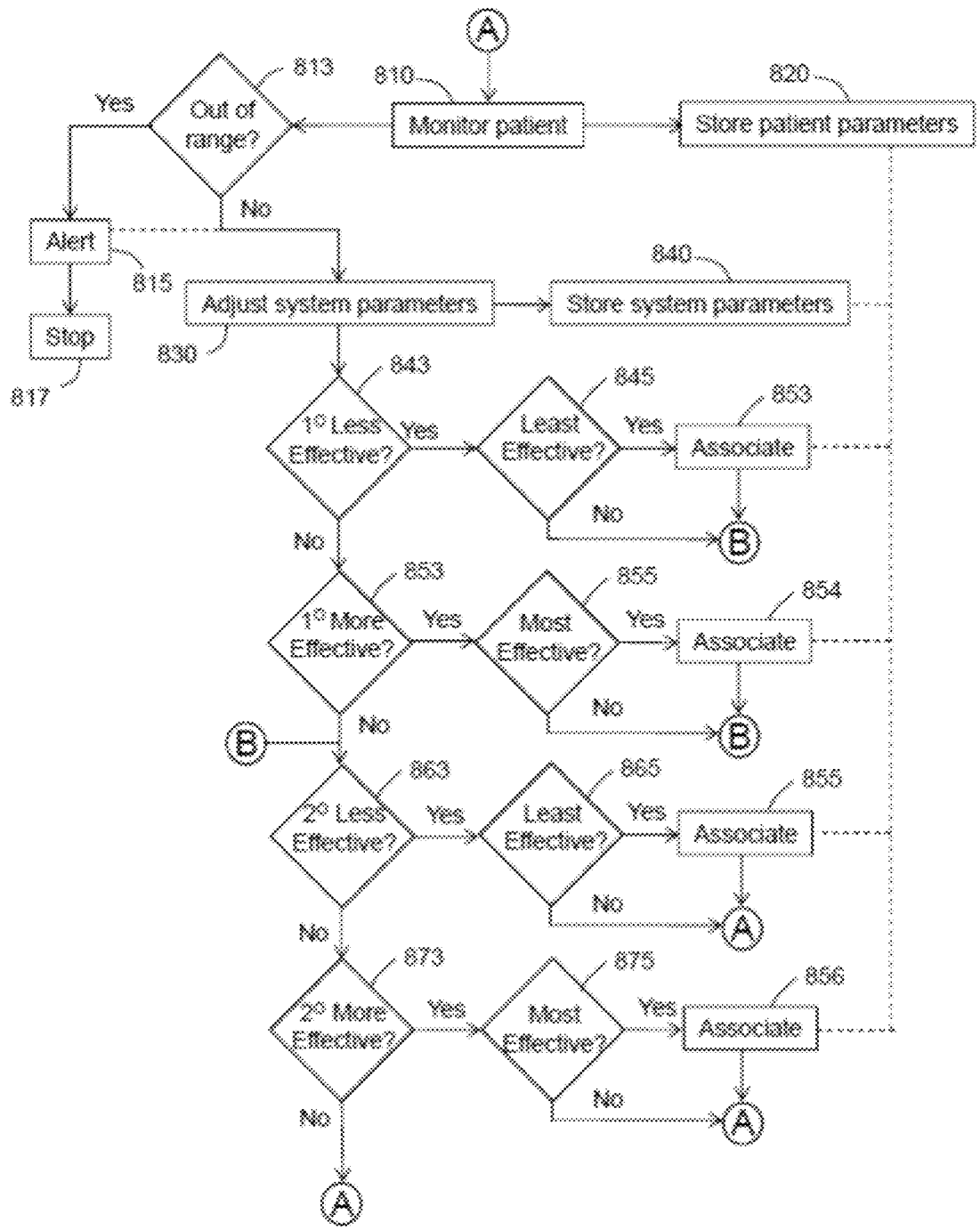
Figure 40:
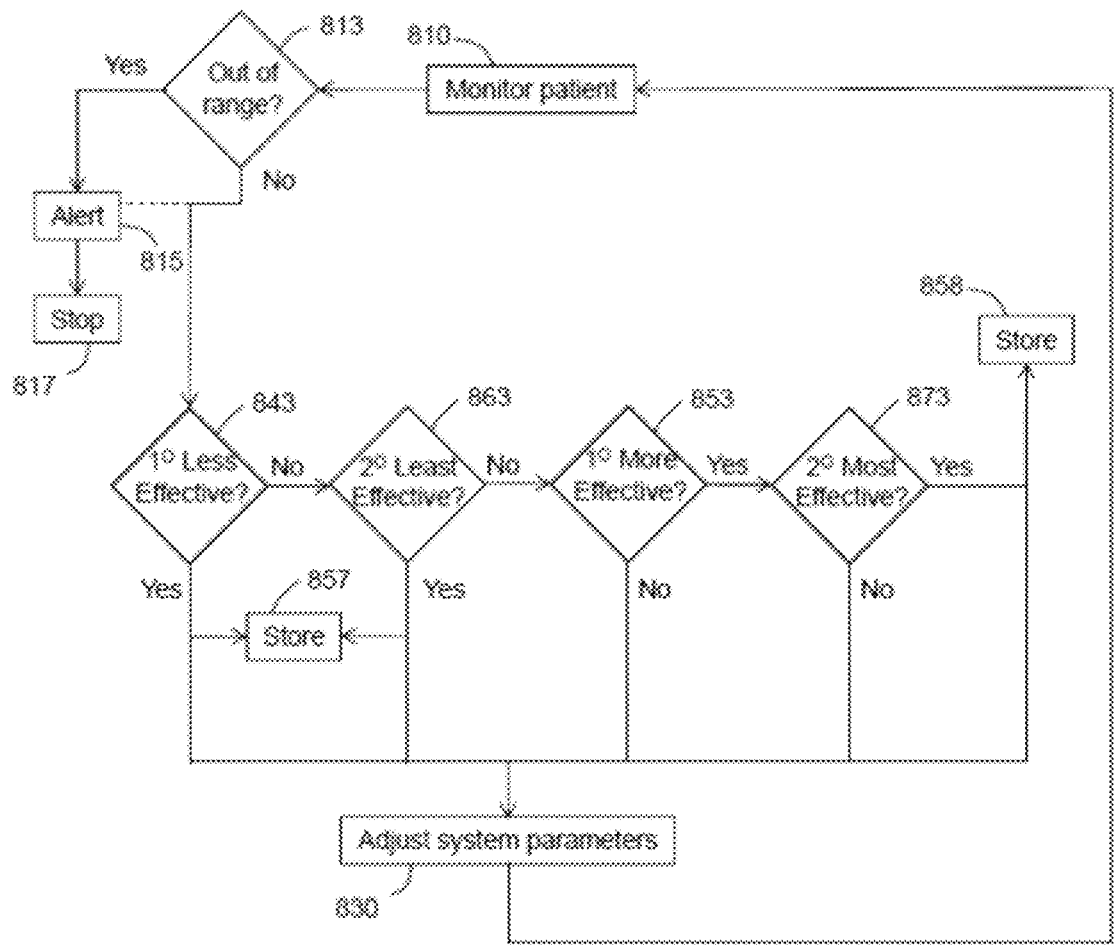

Referring now to FIG. 39, an embodiment of a method where more than one patient parameter variable is evaluated in a manner similar to that described with regard to FIG. 40. In the embodiment depicted in FIG. 39, two patient parameter variables are evaluated. However, it will be understood that any number of patient parameter variables may be evaluated by employing a method as depicted in FIG. 39 or using any other suitable method. In the embodiment depicted in FIG. 39, the variables are labeled "primary" and "secondary", as it may be desirable to prioritize patient parameter variables. For example, in some cases it may be desirable to monitor blood pressure and attempt to achieve a stable blood pressure at or near a target range throughout the session because hypotension is one of the most common side effects of blood fluid removal sessions. That is, as long as other patient parameters are not out of a predetermined range, the system may attempt to keep blood pressure in check and make adjustments to that end. However, in some cases, reducing arrhythmias is the primary goal, as many patients for which a blood fluid removal process is indicated dire from complications due to arrhythmias. If arrhythmias are determined to be the primary patient parameter, the blood fluid removal system may attempt to keep arrhythmias in check and make adjustments to this effect without regard to other patient parameters, e.g., as long as the other patient parameters remain within acceptable limits.

The method depicted in FIG. 39 includes monitoring patient parameters 810 (at least a primary and secondary patient parameter), storing patient parameter data 820, and determining whether a parameter, or aspect thereof, is out of a predetermined range 813. If the parameter is out of range, an alert may be issued 815, the blood fluid removal session may be stopped 817 or the session may continue. If the parameters are determined to not be out of range 813, the system parameters may be adjusted 843 and stored 840. A determination may then be made as to whether the primary patient parameter is less effective 843, e.g. by comparing current patient parameter data to stored patient parameter data resulting from system parameter adjustments that occurred just prior to the current set of system parameters. If the primary patient parameter is determined to be less effective 843, the current stored patient parameter data may be associated 853 with the current stored system parameters. Alternatively or in addition, a determination may be made as to whether the current patient parameter data regarding the primary parameter is the lease effective that has been detected in the patient in a current or previous blood fluid removal session 845; e.g., as discussed above with regard to FIG. 39. If it is the least effective, the current stored patient parameter data may be associated 853 with the current stored system parameters as described above with regard to FIG. 38. Similarly determinations as to whether the primary patent parameter data is more effective 853 or the most effective to date 855 may be made and stored system and patient parameters may be associated 854. Similar determinations regarding whether the secondary patient parameter, or a value associated therewith, is less effective 863, the least effective 865, more effective 873, the most effective 875 and appropriate associations 855, 856 may be made. In this manner, the system may identify and learn how system parameters may affect individually monitored patient parameters, such as blood pressure, heart rate, fluid volume, and electrolyte concentration. Based on this information, the system may make choices as to which system parameters may be employed to produce results that are likely to be favorable to the patient.

Referring now to FIG. 40 a flow diagram depicting a process where the combined response of two or more patient parameters to changes in system parameters 830 is tracked. For the purposes of convenience some of the steps depicted and described above with regard to FIGS. 39-40 are omitted from FIG. 40. However, it will be understood that the same or similar steps may be employed with regard to the method depicted in FIG. 40. In the depicted embodiment, patient parameters and system parameters are stored (857, 858) only when both the primary and secondary patient parameters are determined to become less effective (843, 863) or more effective (853,873). In this manner, the system may identify or learn which system parameters result in desirable (or undesirable) changes in multiple patient parameters.

Through the association of patient parameter data and system parameter data as shown in FIGS. 37-40 and discussed above, a history of patient responses to changing system parameters may be obtained. This history, which may be in the form of a lookup table, may be consulted prior to or during a blood fluid removal session to determine which system parameters, given the patient's physiological parameters at a given point in time, are more likely to cause the patient to respond favorably and which system parameters are more likely to cause the patient to respond negatively. Accordingly, the system may respond by adjusting parameters to those that are more likely to cause the patient to respond favorably.

Figure 41:
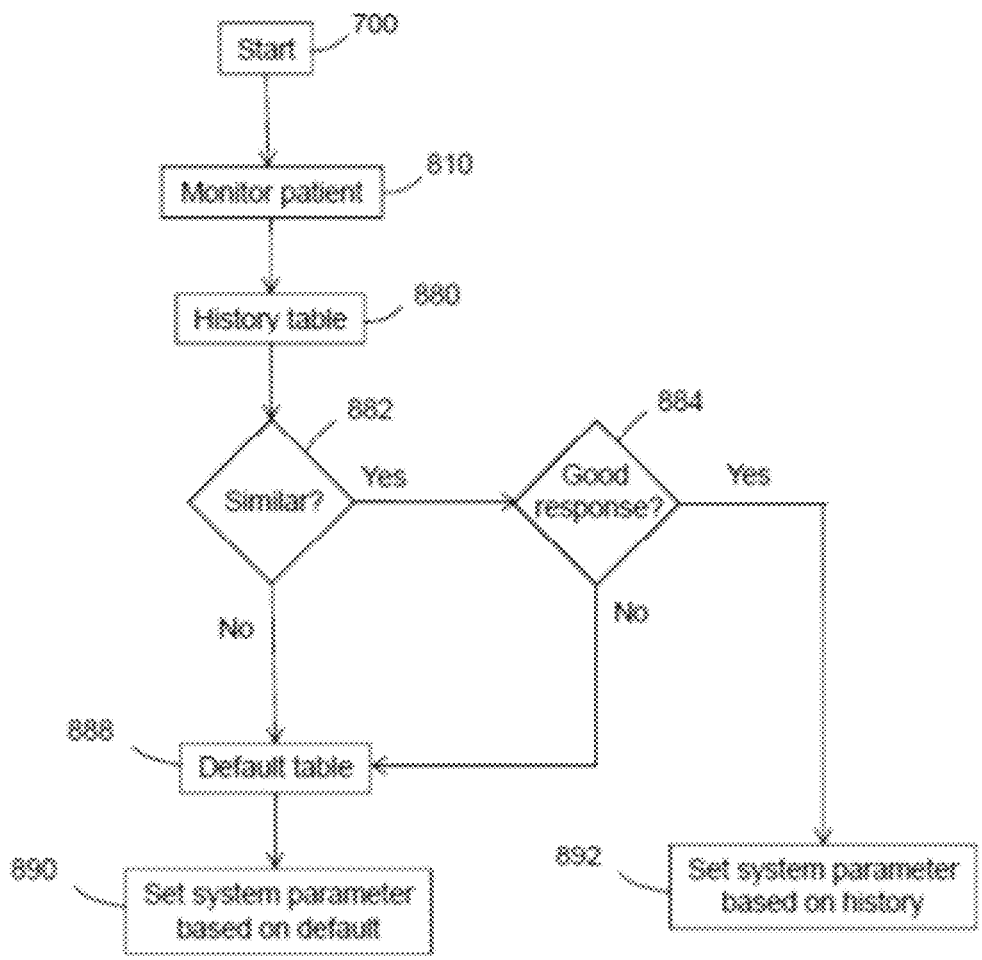

For example and with reference to FIG. 41, a flow diagram is shown that depicts and embodiment of how stored and associated data (e.g., as discussed above with regard to FIGS. 37-40) may be used to determine which system parameters to use at a given time in a blood fluid removal session. The method includes initiating or starting a blood fluid removal session 700, monitoring patient parameters 810, and consulting history lookup table 880, which may be generated by associating system parameters and patient parameters as described above with regard to FIGS. 37-40. A value associated with the current patient parameter data is compared to data regarding a corresponding value in the lookup table, and a determination is made as to whether the current patient parameter is similar to prior patient parameter data stored in the history table 882. By way of example, a value of a current patient parameter data set may be determined to be similar to a corresponding value in the lookup table if the values are within 10%. The system may scroll through the lookup table to identify the closest corresponding value, if more than one corresponding value is within the predetermined cutoff for being considered similar (e.g., within 10%). As used herein, a "corresponding" value is a value of the same parameter obtained at different times. The value may be a magnitude, a rate of change, an average, or the like. The parameter may be blood pressure, heart rate, fluid volume, concentration of electrolyte, or the like.

If more than one parameter or value of a parameter is compared to data in the lookup table, the system may determine whether each value for each parameter is within the predetermined cutoff for being considered similar and identify a prior patient parameter data set as being most similar by prioritizing or weighting parameters or by summing the percent differences between all of the current values and the corresponding values in the lookup table. Regardless of how the system determines whether a current patient parameter data set is similar, or most similar, to a prior patient data set stored in the history table, a determination may be made as to whether the patient's response to the system parameters associated with the stored patient parameter data table was a favorable response 884; e.g., was "better" (or "more effective") or "best" (or "most effective") as discussed above with regard to FIGS. 38-40. If the prior patient response was determined to be a good or "effective" response, the current system parameters may be set according to the parameters stored in the lookup table 892. If the prior patient response was considered to not to be similar 882 or effective 884, a default table may be consulted 888 which contains non-patient specific system parameters that would generally be considered suitable in general circumstances or that would be considered suitable for a patient presenting with the current physiological parameters. The system parameters may then be set according to the parameters stored in the default table 890.

It will be understood that prior patient negative responses (e.g., "less effective", "least effective") may be stored in a lookup table, accessed and used in a similar manner to that described with regard to the "effective" responses in FIG. 41. In some embodiments, separate lookup tables are maintained for "effective" responses (e.g., an "increased effectiveness" data table) and for "ineffective responses" (e.g., a "decreased effectiveness" data table). In some embodiments, the "increased effectiveness" lookup table and the "decreased effectiveness" lookup table are the same data table, which stores patient parameters and associated system parameters that resulted in "more effective", "most effective", "less effective" or "least effective" patient parameters.

Figure 42:
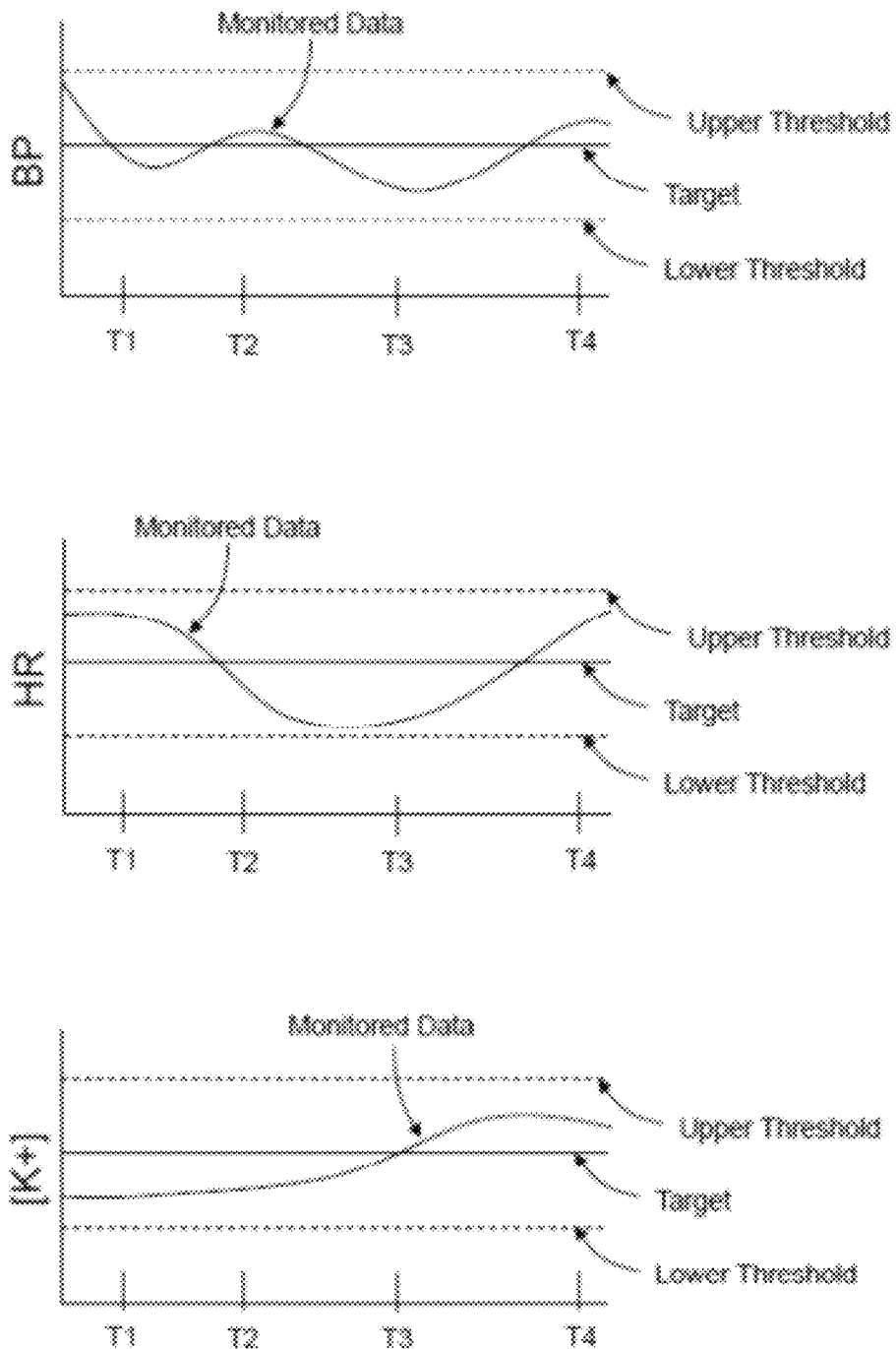
FIG. 42 is a schematic graphical representation of monitored data (not actual data) shown for purposes of illustration.

For purposes of example and to provide some clarity with regard to how one (or a blood fluid removal system) may determine whether patient parameter data is "out of range", "more effective", "less effective", and the like (as discussed above with regard to FIGS. 38-40), graphical schematic data is presented in FIG. 42 showing representations of monitored data (not actual data) for blood pressure (BP), heart rate (HR), and potassium concentration in the patient's blood ($[K^+]$). In the schematic illustration, system parameters are changed at times T1, T2, T3 and T4. The patient parameters (BP, HR, $[K^+]$) are shown as changing in response to the changes in blood fluid removal system parameters. As shown, not all patient parameters will respond similarly (e.g., more effective or less effective) in response to a system parameter change. In the depicted schematic illustrations, a desired target value is shown for each patient parameter. If the monitored data value achieves or approaches the target, a determination may be made that the change in system parameter resulted in an improvement or "more effective" state for that parameter. If the monitored data value deviates from the target, a determination may be made that the change in system parameter resulted in a worsening or "less effective" state for that parameter. It will be understood that the timing of the patient parameter response to a change in system parameters may vary greatly from patient parameter to patient parameter. In some cases, changes in a patient parameter may be observed within seconds or minutes of a change in a system parameter. In other cases, a change in a patient parameter in response to a change in a system parameter may take hours or more to be fully appreciated or observed.

Figure 43:
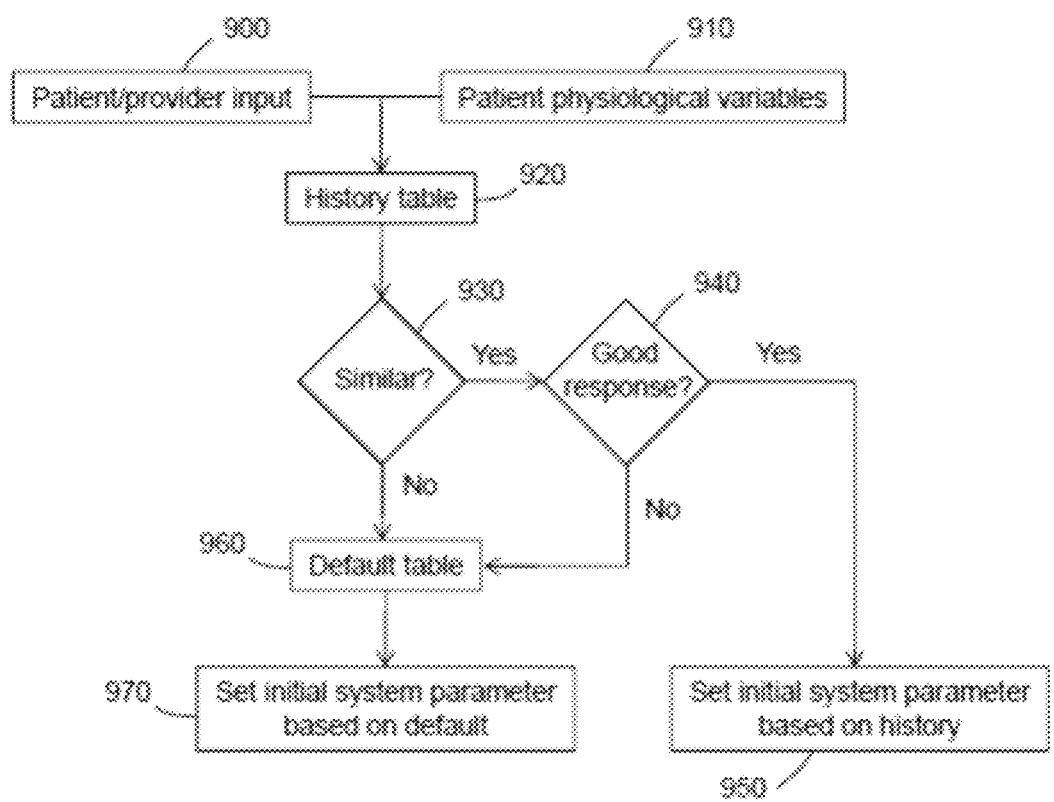
FIG. 43 is a flow diagram illustrating an embodiment of a method described herein.

In the graphical depictions of the represented monitored data presented in FIG. 43, a lower threshold value and an upper threshold value are depicted by horizontal dashed lines. If the monitored data for a patient parameter exceeds the upper threshold value or crosses below the lower threshold value, a determination may be made that the value for that parameter is "out of range."

It will be understood that the condition of a patient may deteriorate with time, which is typical of patients having chronic kidney disease. Accordingly, the targets and upper and lower thresholds may vary with time. These targets and thresholds may be modified by input from, for example, a healthcare provider from time to time based on, e.g., the patient's health or status of patient parameters. Alternatively, the system may automatically adjust target or threshold values over time based on population data or based on data of a particular patient indicative of a generally deteriorating condition. If the target or thresholds are adjusted to or near predetermined cutoff values, an alert may be issued to that effect.

Further, target and threshold values for one or more parameters may be modified on a session-by-session basis. For example, if the patient is excessively fluid overloaded prior to a given session, the target or threshold tissue fluid levels may be adjusted upward for the next or current session. The negative consequences of too much fluid removal in one session or at too fast of a rate may outweigh the negative consequences of higher fluid levels remaining in the patient. Additional or more frequent fluid removal sessions may be employed to return the patient to more desirable fluid levels.

As shown in the examples presented in FIG. 23, the patient parameters change over time. In embodiments, values of one or more patient parameters are averaged over a period of time to account for fluctuations that may occur. The averaged value may be compared to the target and thresholds for determining whether a patient is improving. By averaging values over time, the effect of an anomalous value that may deviate significantly from the target value or may be out of bounds may be diminished. Of course, thresholds may be set for single occurrences, for example if the values of those occurrences may present an imminent health concern to the patient. In embodiments, the presence a single occurrence that deviates significantly from other recent occurrences may result in activation of a subroutine or monitoring method for detecting similar subsequent deviations. In embodiments, consecutive significant deviations, a percent of significant deviations within a given number of samples, or the like, may result in activation or an alert or alarm.

In embodiments, patient parameters are measured or monitored within discrete windows of time rather than continuously. Such time sampling may be valuable for implantable systems or systems having implantable components as the power and processing requirements may be reduced relative to continuous monitoring.

The discussion with regard to FIGS. 37-42 has been primarily directed to blood fluid removal systems and processes that may occur during a blood fluid removal session for associating system parameter data and patient parameter data to enhance the blood fluid removal session or to tailor the blood fluid removal treatments to render the treatment patient-specific. It will be understood that any suitable method or process may be employed to achieve such results, and such methods or processes are contemplated for use herein. It will be further understood that similar methods or processes may be employed to enhance or tailor system parameters prior to initiating a blood fluid removal session so that patient-specific parameters may be set at the beginning of a session.

For example and with reference to FIG. 43 a flow diagram depicting a method that may be employed to determine which system parameters to select at the beginning of a blood fluid removal session is shown. The depicted method is similar in many respects to the method depicted in FIG. 41. In FIG. 43, the method includes receiving, inputting or obtaining patient or physician input 900 and patient physiological parameters 910. As discussed above with regard to FIG. 35, physician or patient input may include how long since the patient's last blood fluid removal session, how long does the patient have for the given blood fluid removal session and the like. In some embodiments, system generated input is provided based on data collected during the last session. Patient physiological parameters can be similar to those described above. A history lookup table may be consulted 920, and a determination can be made as to whether the patient has previously come to a blood fluid removal session in a similar state 930 based on the patient or physician input, the patient's physiological parameters, or other input. If a determination is made that the patient has come to previous blood fluid removal session in a similar state 930, which decision may be made generally as described above with regard to FIG. 41, a determination can be made as to whether system parameters were used in such a previous session to which the patient responded to favorably or had an "effective" response 940. If the patient is determined to have had an effective response, then the initial system parameters may be set in accordance with the parameters stored in the history table 950. If the patient is determined to not have come to a blood fluid removal session in a similar state 930 or to not have had an effective response 940, then a default table (e.g., similar to as described above with regard to FIG. 41) may be consulted 960 and the initial system parameters can be set according to the parameters in the default table 970.

Additional examples of systems and teachings useful in practicing the above embodiments can be found in, for example, U.S. Provisional Patent Application No. 61/480, 541, filed on Apr. 29, 2011, and U.S. patent application Ser.

No. 13/424,517 filed Mar. 20, 2012, both entitled BLOOD FLUID REMOVAL SYSTEM PERFORMANCE MONITORING, U.S. Provisional Patent Application No. 61/480,539, filed on Apr. 29, 2011, and U.S. patent application Ser. No. 13/424,533 filed Mar. 20, 2012, both entitled ADAPTIVE SYSTEM FOR BLOOD FLUID REMOVAL, which applications are hereby incorporated herein by reference in their entirety to the extent that they do not conflict with the present disclosure.

Working Example

Figure 44:
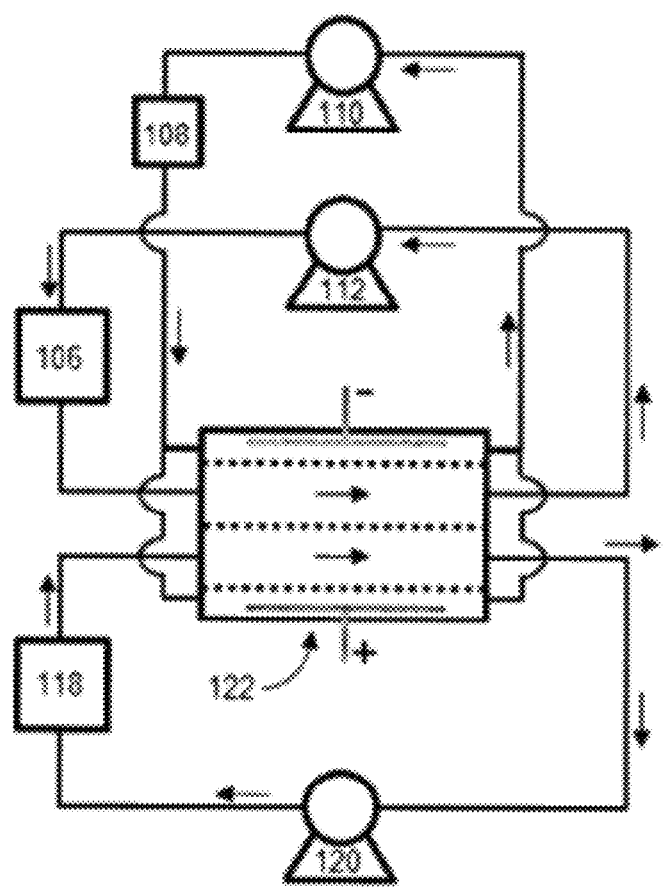
FIG. 44 shows an experimental set-up for electrolytic purification of a spent dialysate.

A lab-scale electrodialysis experiment was performed to establish the feasibility of purifying spent dialysate using an electrodialysis unit 122. The experimental set-up is shown in FIG. 44. The experiment was run in recirculation set-up with a concentrate reservoir 106, diluate reservoir 118 and electrode rinse reservoir 108. Peristaltic pumps 110, 112 and 120 were used for recirculation and the flow rates were set at 500 mL/min. The electrodialysis unit 122 used was model ED64004 (PCCell (Germany)). The unit consisted of 10 cell pairs with 11 Neosepta CMX cation exchange membranes and 9 Neosepta AMX anion exchange membranes, purchased from ASTOM Corporation (Japan). Each membrane has an active area of 64 cm$^2$ resulting in a total active area of 1280 cm$^2$. The electrodes were titanium with a platinum/iridium coating. Spent dialysate was prepared with the composition listed in Table 6, below. The spent dialysate was titrated to a pH of 6.5 with 37 wt % hydrochloric acid. The concentrate solution was prepared by mixing 0.56 volume parts of spent dialysate with 0.44 volume parts of deionized water. The electrode rinse solution consisted of 100 mM sodium sulfate titrated to a pH of 3 with sulfuric acid.

TABLE 6

Composition of Spent Dialysate

| Component | Concentration |
|---|---|
| Na+ | 140 mM |
| Ca++ | 1.5 mM |
| K+ | 3 mM |
| Mg++ | 0.375 mM |
| Cl− | 171 mM |
| Acetate | 4 mM |
| Bicarbonate | 33 mM |
| Glucose | 200 mg/dL |
| Ammonium | 65 mM |
| Phosphate | 2.6 mM |

3000 ml of spent dialysate was added to the diluate reservoir 118. The concentrate reservoir 106 contained 600 mL of concentrate solution, described above. The electrode rinse reservoir contained 2000 mL of the electrode rinse solution described above. The experiment was started by applying 8V DC across the electrodialysis unit and starting the re-circulating pumps at a flow rate of 500 mL/min. The concentrate 106 and diluate 118 reservoirs were placed on stir-plates with magnetic stir-bars to ensure good mixing. At various time points, 1 ml samples were removed from each reservoir and analyzed for sodium, potassium, calcium, magnesium, chloride, ammonium, phosphate, bicarbonate and pH using a CCX analyzer and a BioProfile 300 analyzer, both manufactured by NovaBiomedical. Also, the current was monitored using a Fluke 179 True RMS multimeter.

Figure 45:
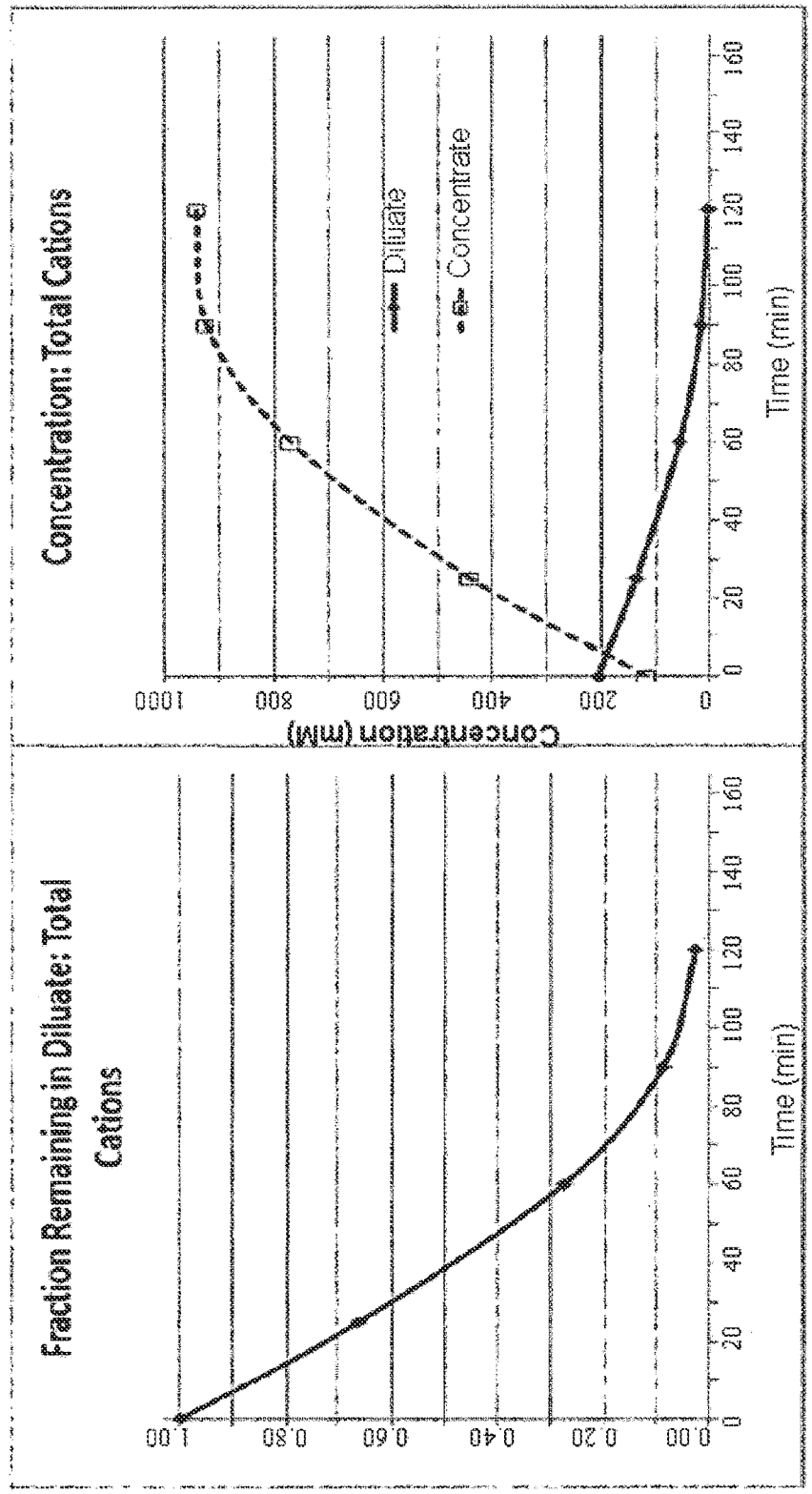
FIG. 45 shows data obtained from an experiment for the electrolytic purification of a spent dialysate.

FIG. 45 shows the fractional reduction in total cation concentration (left) and the total cation concentrations in the diluate and concentrate reservoirs (right). After 90 minutes, the total cation concentration was reduced by 90%. The current during the run decreased slowly from 1450 mA down to 220 mA after two hours.

Figure 46:
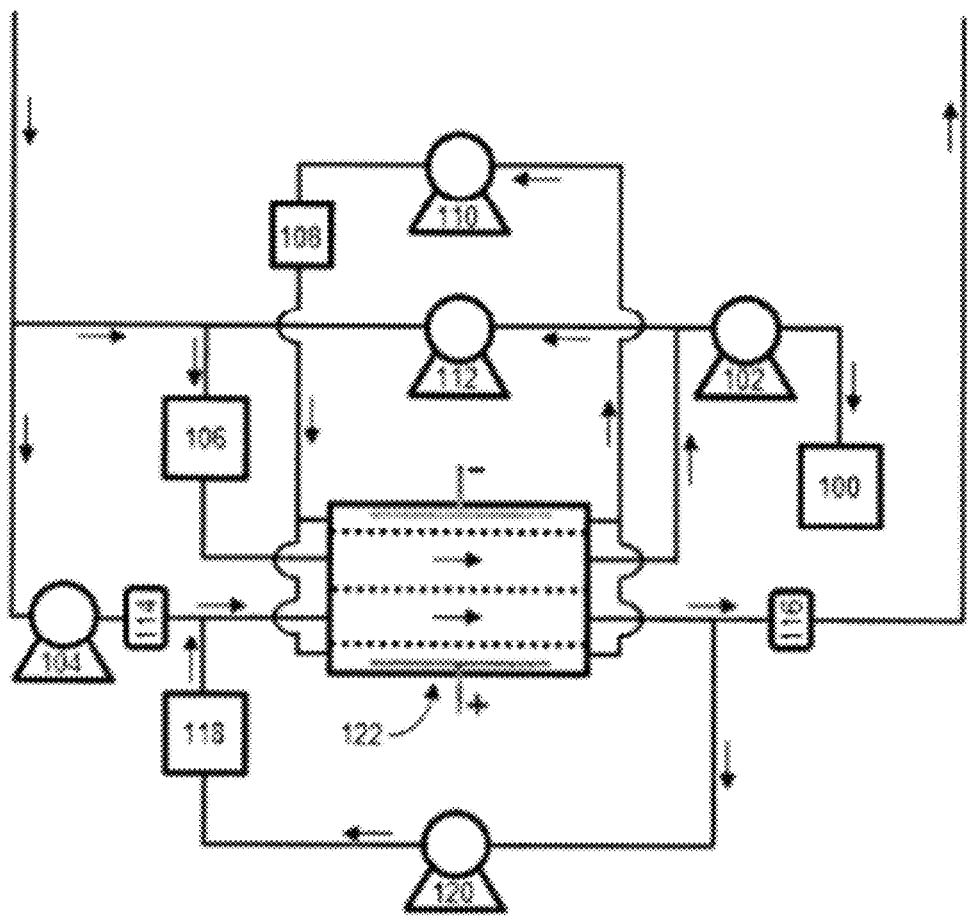
FIG. 46 shows a schematic for an embodiment of a purification module in accordance with some embodiments.

Using the experiment presented above, the operation of a scaled-up configuration shown in FIG. 46 can be demonstrated. For a portable dialysis system, the dialysate recirculation pump 104 can flow at 129 ml/min and the control pump 102 can flow at a flow rate of 14 ml/min (8 ml/min from ultrafiltration and 6 ml/min from the concentrate infusion set 35). The concentrate 112, diluate 120 and electrode rinse 110 re-circulating pumps can flow at 500 mL/min or higher. Based on the experiment above, the diluate 118, concentrate 106 and electrode rinse 108 reservoirs can have volumes of 500 mL, 2000 mL, and 2000 mL, respectively. The lab-scale experimental data indicates 90% removal of total cations in 90 minutes for the 3000 mL diluate reservoir, which is equivalent to a feedflow rate of 33.33 mL/min. Therefore, in order to remove 90% of total cations from a dialysate flow rate of 129 mL/min, the electrodialysis unit 122 can have a total active membrane area increased by a factor of 3.9 compared to the example, which would result in a total active membrane area of 0.5 m$^2$. The membrane area could be increased by adding more cell pairs to the stack or by increasing the area of each membrane, or a combination of both.

We claim:

1. A multimodal dialysis apparatus, comprising:
   a blood circuit for transporting blood extracorporeally to a hemodialysis unit;
   a dialysate circuit for transporting a fluid to contact the hemodialysis unit, wherein the fluid increases in concentration with at least one waste species during operation;
   an infusate pump for adding a potassium salt to the fluid in the dialysate circuit; and
   a composition sensor comprising a potassium-sensitive electrode for measuring a potassium ion concentration in one or more of blood in the blood circuit and fluid in the dialysate circuit,
   a purification unit comprising an electrodialysis unit having a diluate chamber and a concentrate chamber and a means for producing an electric field, wherein one or more ions are removed from the fluid in the dialysate circuit;
   a reverse osmosis unit located at an outlet of the purification unit to selectively remove solutes from the fluid;
   a conditioning unit comprising urease; wherein the conditioning unit is located at an outlet of the reverse osmosis unit; and a conduit connecting an outlet of the conditioning unit to an inlet of the electrodialysis unit for returning fluid exiting the conditioning unit to the electrodialysis unit;
   wherein the infusate pump is controlled by a controller to adjust a rate of addition of potassium ions to the fluid in the dialysate circuit based at least in part on data from the composition sensor.

2. The apparatus of claim 1, wherein the electrodialysis unit further comprises a concentrate solution circulation loop for recirculating a concentrate solution through the concentrate chamber, and the concentrate solution circulation loop has a reservoir containing a volume of concentrate solution.

3. The apparatus of claim 1, further comprising a pump for conveying at least a portion of the concentrate solution exiting the electrodialysis unit from an additional outlet to a reservoir or waste collector.

4. The apparatus of claim 1, further comprising a diluate solution recirculation loop comprising a diluate solution pump, wherein the diluate solution circulation loop connects an outlet of the diluate chamber to an inlet of the diluate chamber for recirculation of at least part of the fluid in the diluate chamber.

5. A multimodal dialysis apparatus, comprising:
   a dialysate circuit for conveying fluid to and from the peritoneal cavity of a patient;
   an infusion pump for adding a potassium salt to the fluid in the dialysate circuit; and
   a composition sensor comprising a potassium-sensitive electrode for measuring a potassium ion concentration in the fluid in the dialysate circuit,
   a purification unit comprising an electrodialysis unit having a diluate chamber and a concentrate chamber and a means for producing an electric field, wherein one or more ions are removed from the fluid in the dialysate circuit;
   a reverse osmosis unit located at an outlet of the purification unit to selectively remove solutes from the fluid;
   a conditioning unit having urease; wherein the conditioning unit is located at an outlet of the reverse osmosis unit, and a conduit connecting an outlet of the conditioning unit to an inlet of the electrodialysis unit for returning fluid exiting the conditioning unit to the electrodialysis unit;
   wherein the infusate pump is controlled by a controller to adjust a rate of addition of potassium ions to the fluid in the dialysate circuit based at least in part on data from the composition sensor.

6. The apparatus of claim 5, wherein the electrodialysis unit further comprises a concentrate solution circulation loop for recirculating a concentrate solution through the concentrate chamber, and the concentrate solution circulation loop has a reservoir containing a volume of concentrate solution.

7. The apparatus of claim 6, further comprising a pump for conveying at least a portion of the concentrate solution exiting the electrodialysis unit from an additional outlet to a reservoir or waste collector.

8. The apparatus of claim 5, further comprising a diluate solution recirculation loop comprising a diluate solution pump, wherein the diluate solution circulation loop connects an outlet of the diluate chamber to an inlet of the diluate chamber for recirculation of at least part of the fluid in the diluate chamber.

9. A method for performing dialysis, comprising:
   contacting a dialysate fluid to a patient or to a medical device such that at least one waste species is transferred from the patient to the dialysate fluid;
   measuring a potassium ion concentration of the contacted dialysate fluid;
   conveying the dialysate fluid to an electrodialysis unit, wherein one or more ions are removed from the dialysate fluid;
   conveying the dialysate fluid to a reverse osmosis unit to selectively remove solutes from the dialysate fluid;
   conveying the contacted dialysate fluid from the electrodialysis unit to a conditioning unit comprising urease; and
   conveying the contacted dialysate fluid from the conditioning unit back to the electrodialysis unit; and
   controlling a rate of addition of potassium ions to a dialysate fluid being conveyed to the patient or to the medical device based upon the measured potassium ion concentration in the contacted dialysate fluid.

10. The method of claim 9, wherein the potassium ion concentration of the contacted dialysate fluid is measured with a potassium-sensitive electrode.

11. The method of claim 9, wherein the potassium ion concentration in a dialysate fluid being conveyed to the patient or the medical device is controlled in a manner to maintain a predetermined mass transfer of potassium ions from the patient to the dialysate.

12. The method of claim 9, wherein the potassium ion concentration in a dialysate fluid being conveyed to the patient or the medical device is controlled in a manner to maintain a predetermined rate of decrease in potassium ion concentration in the blood plasma of the patient.

13. The method of claim 9, wherein the medical device is a hemodialyzer and blood from the patient is transported through the hemodialyzer.

14. The method of claim 9, wherein the dialysate fluid is contacted with the patient by being introduced to the peritoneal cavity.

15. The method of claim 9, wherein the dialysate fluid is infused with a controlled amount of a potassium salt, contacted with the patient or the medical device such that at least one waste species is transferred from the patient to the dialysate fluid and potassium ion is transported from the patient to the dialysate.

16. The method of claim 9, further comprising the step of recirculating at least a portion of the dialysate fluid from an outlet of the electrodialysis unit to an inlet of the electrodialysis unit through a diluate circulation loop; wherein the diluate circulation loop connects an outlet of a diluate chamber in the electodialysis unit to an inlet of the diluate chamber of the electrodialysis unit for recirculation.

* * * * *